(12) United States Patent
Xu et al.

(10) Patent No.: US 9,738,900 B2
(45) Date of Patent: *Aug. 22, 2017

(54) TRANSGENIC PLANTS EXPRESSING A PH-SENSITIVE NITRATE TRANSPORTER

(71) Applicants: Nanjing Agricultural University, Nanjing, Jiangsu (CN); Plant Bioscience Limited, Norwich, Norfolk (GB)

(72) Inventors: Guohua Xu, Nanjing (CN); Xiaorong Fan, Nanjing (CN); Qirong Shen, Nanjing (CN); Anthony Miller, Norwich (GB)

(73) Assignees: Plant Bioscience Limited, Norwich, Norfolk (GB); Nanjing Agricultural University, Nanjing, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,682

(22) Filed: Oct. 4, 2016

(65) Prior Publication Data

US 2017/0016014 A1    Jan. 19, 2017

Related U.S. Application Data

(63) Continuation of application No. 14/642,858, filed on Mar. 10, 2015, now abandoned, which is a continuation of application No. 14/172,294, filed on Feb. 4, 2014, now Pat. No. 9,012,721, which is a continuation-in-part of application No. PCT/CN2013/071384, filed on Feb. 5, 2013.

(51) Int. Cl.
   C12N 15/82    (2006.01)
   C12N 5/14     (2006.01)

(52) U.S. Cl.
   CPC .......... *C12N 15/8243* (2013.01); *C12N 5/14* (2013.01); *C12N 15/8241* (2013.01); *C12N 15/8261* (2013.01); *C12N 15/8271* (2013.01); *C12N 15/8279* (2013.01)

(58) Field of Classification Search
   None
   See application file for complete search history.

(56) References Cited

U.S. PATENT DOCUMENTS

| | | | | |
|---|---|---|---|---|
| 5,495,007 A * | 2/1996 | Thompson | ........... | C07K 14/415 435/320.1 |
| 9,012,721 B2 * | 4/2015 | Xu | ..................... | C12N 15/8261 435/410 |
| 2007/0044176 A1 * | 2/2007 | Allen | ................... | C07K 14/415 800/278 |
| 2008/0127365 A1 * | 5/2008 | Sanz Molinero | .... | C07K 14/415 800/278 |
| 2009/0183270 A1 | 7/2009 | Adams | | |

FOREIGN PATENT DOCUMENTS

| CN | 101392257 | 3/2009 |
|---|---|---|
| WO | 2008142036 | 11/2008 |

OTHER PUBLICATIONS

Wang and Tsay 2001 (The Plant Cell 23: p. 1945-1957).*
Wang and Tsay, The Plant Cell (2001), 23: pp. 1945-1957.
Feng, et al., 12011, Journal of Experimental Botany, 7: pp. 2319-2332.
PCT/GB2014/050327, "International Search Report" mailed Aug. 5, 2014.
Frasier, V., et al. Constitutive Expression of a Putative High-affinity Nitrate Transporter in Nicoyiana Plumbaginifolia: Evidence for Post-Transcriptional Regulation by a Reduced Nitrogen Source, The Plant Journal (2000) 23 (4) pp. 489-196.
Katayama, H. et al., "Production and Characterization of Transgenic Rice Plants Carrying a High-Affinity Nitrate Transporter Gene (OsNRT2.1)", Breeding Science (2009) vol. 59, pp. 237-243.
Feng, H. et a., "Spatial Expression and Regulation of Rice High-Afffinity Nitrate Transporters by Nitrogen and Carbon Status", Journal of Experimental Botany, vol. 62, No. 7 (Jan. 2011) pp. 2319-2332.
Guohua, X, et al. "Plant Nitrogen Assimilation and Use Efficiency", Annual Review of Plant Biology (2012) vol. 63, No. 1, pp. 153-182.
Patent Abstract of CN 101392257A, Published Mar. 15, 2009.

* cited by examiner

*Primary Examiner* — Matthew Keogh
(74) *Attorney, Agent, or Firm* — McKee, Voorhees & Sease, PLC

(57) ABSTRACT

The invention relates to transgenic plants with improved growth and nitrogen use efficiency expressing nitrate transporter gene, methods of making such plants and methods for improving growth and nitrogen use efficiency.

29 Claims, 33 Drawing Sheets

Figure 1A-C
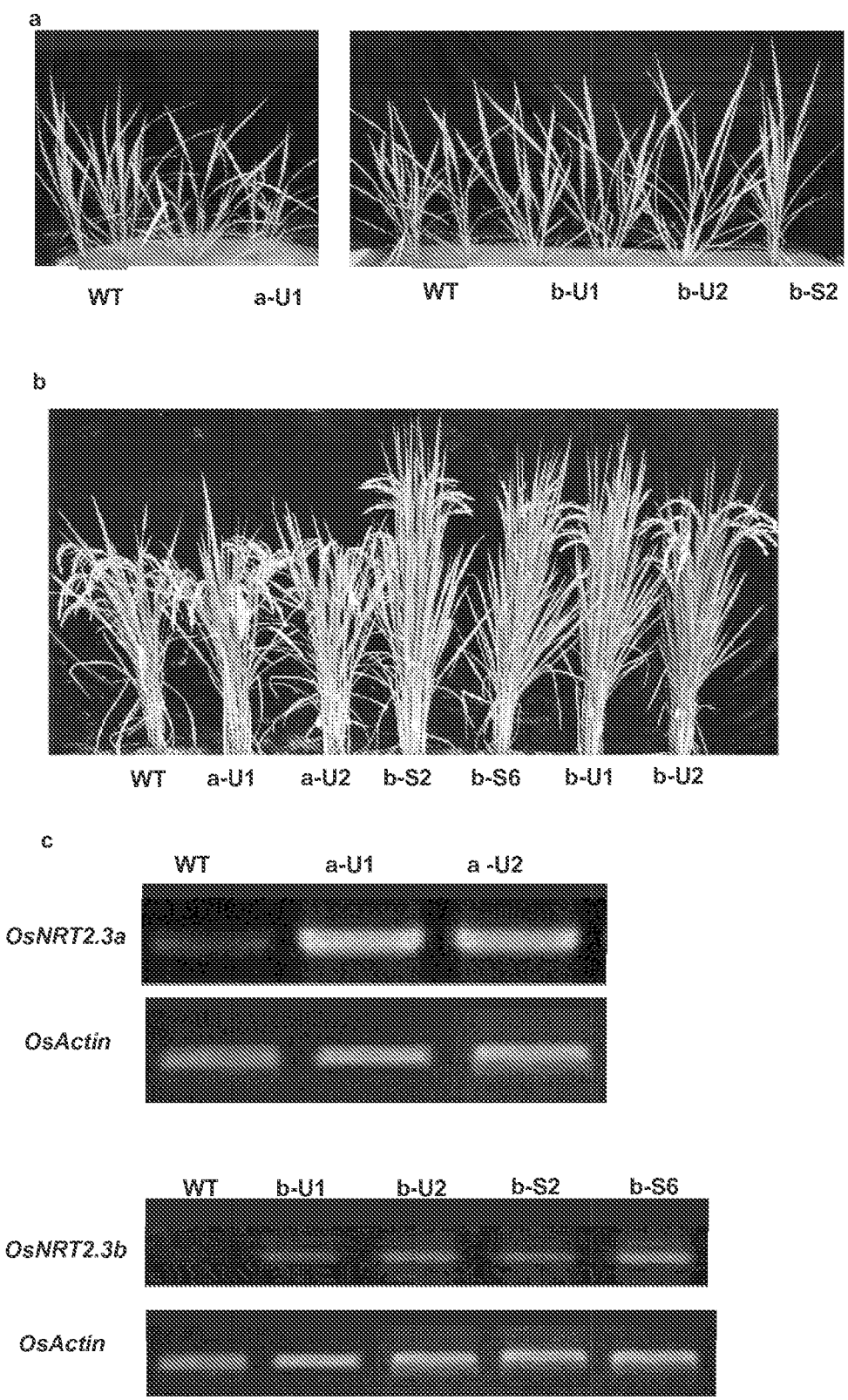

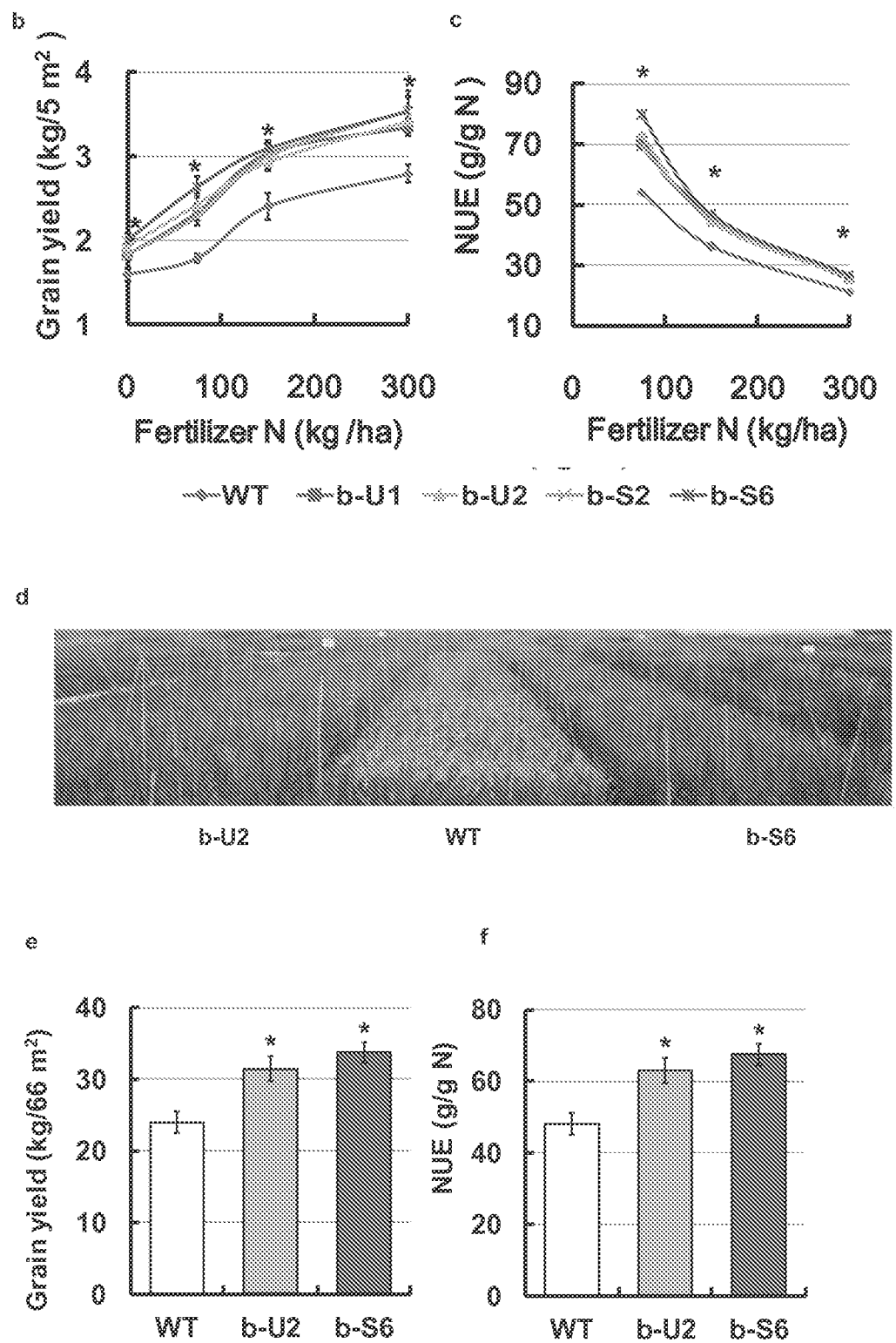
Figure 2B-F

Figure 3A-C
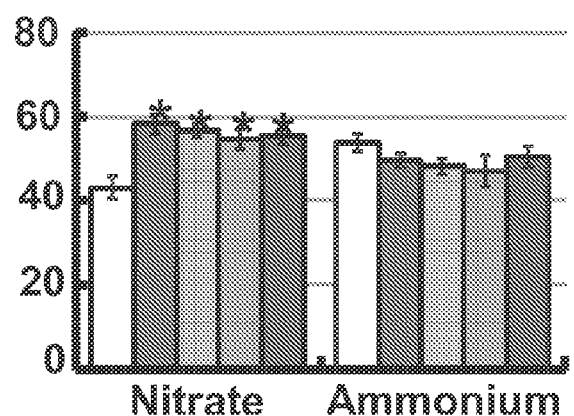
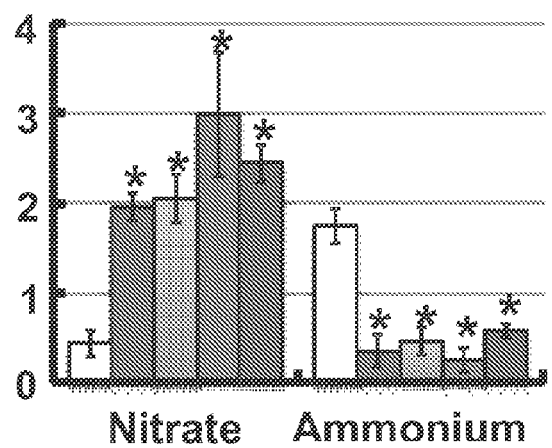
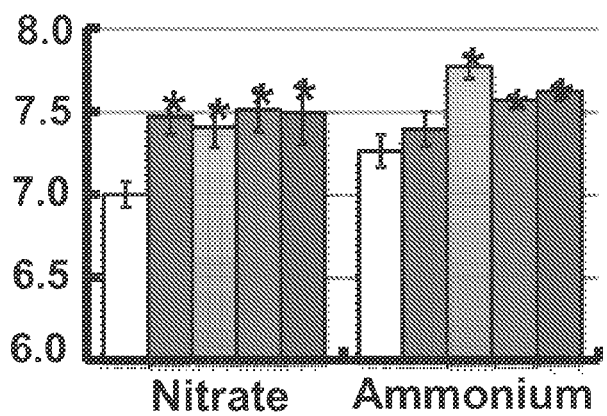
☐ WT ▨ b-U1 ☐ b-U2 ▨ b-S2 ▨ b-S6

Figure 3D-E
d
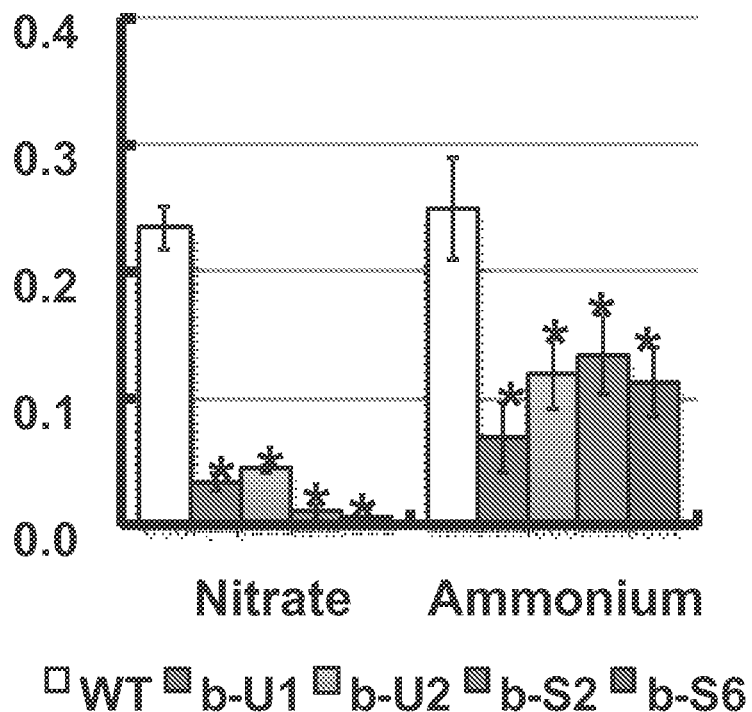
e
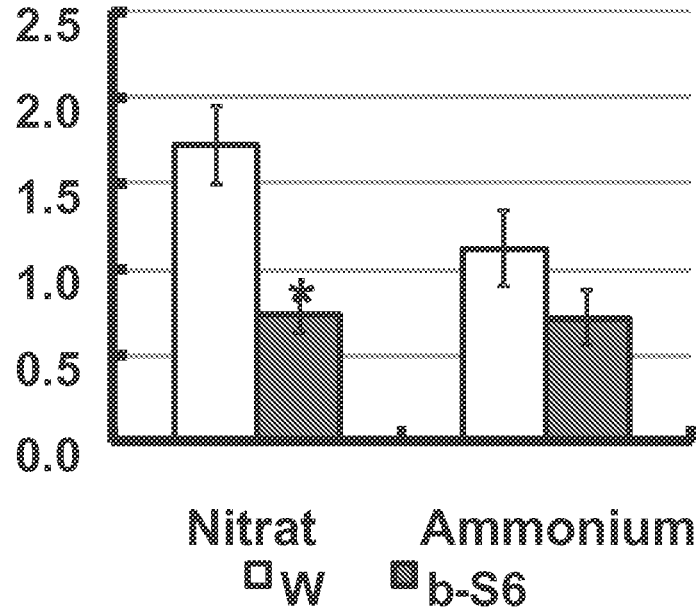

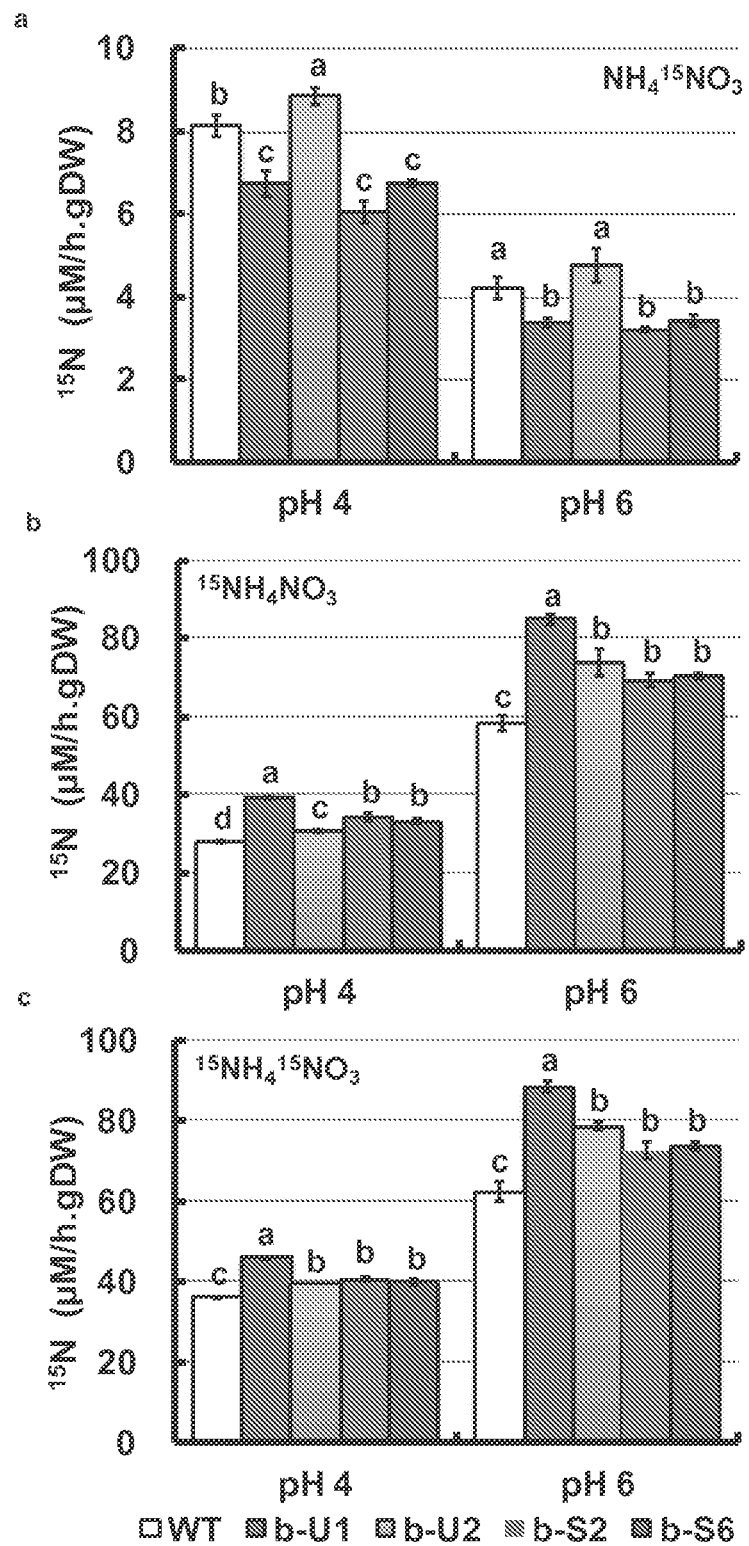
Figure 4A-C

Figure 5A-B
a
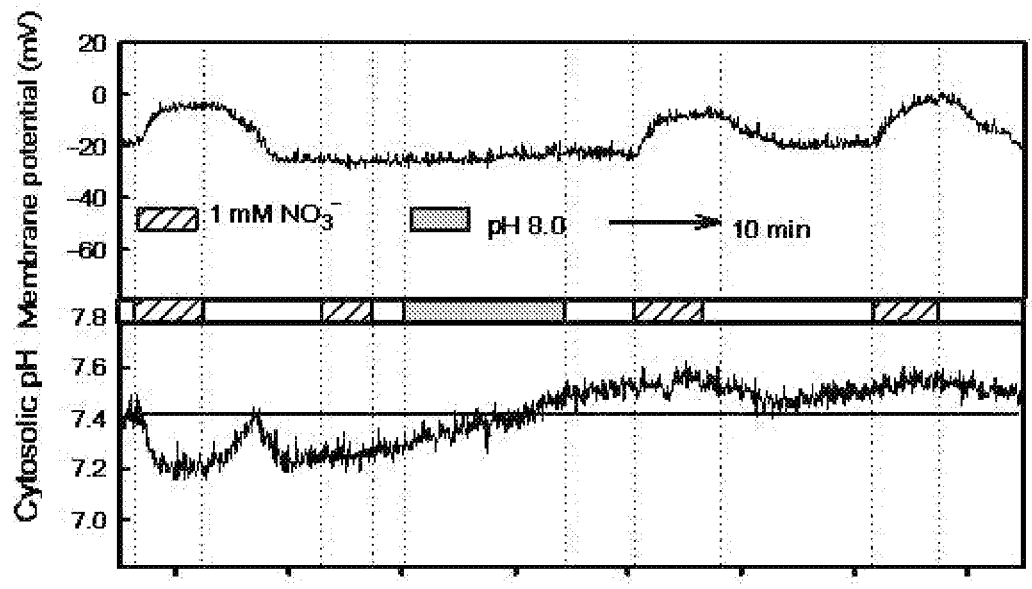
b
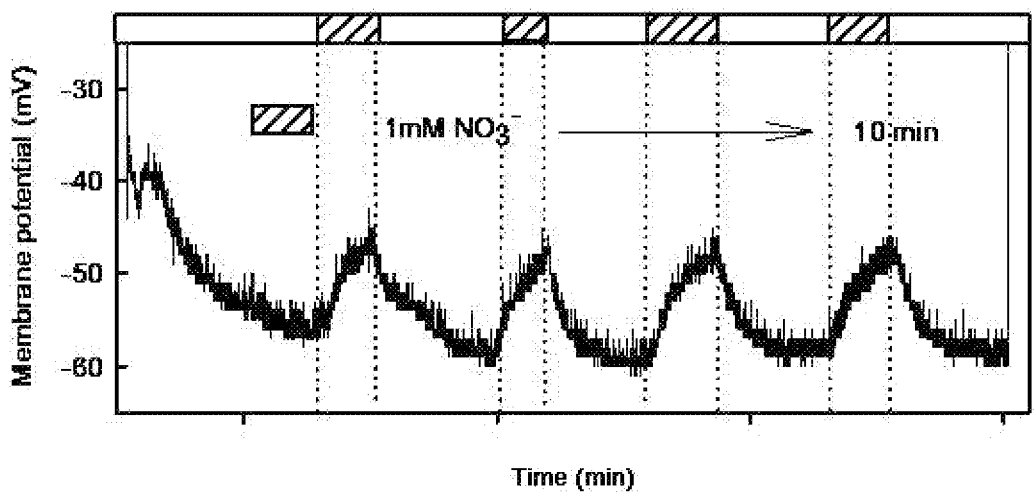

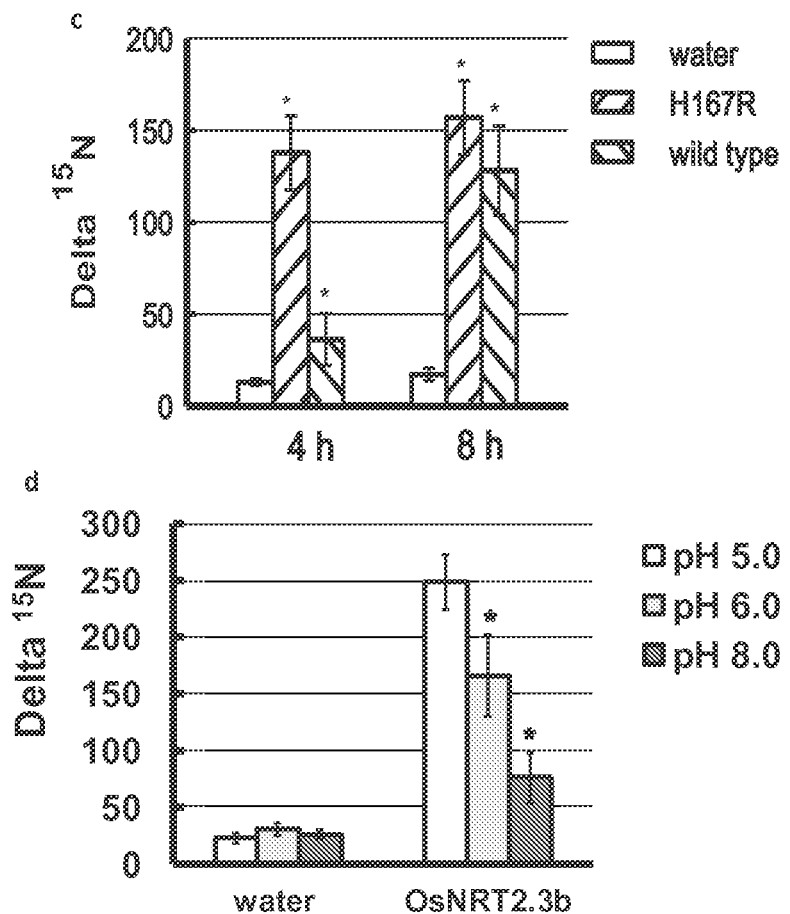

Figure 6A-B
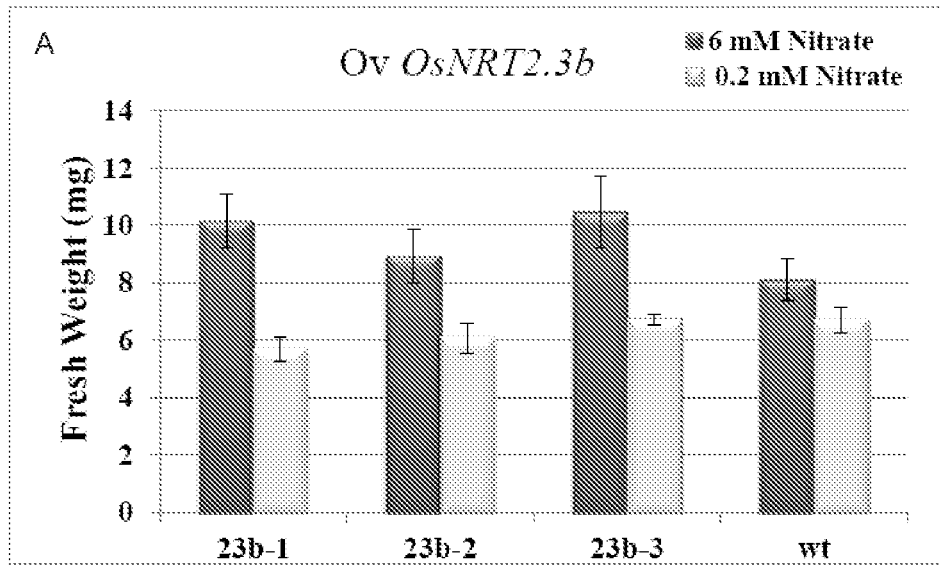
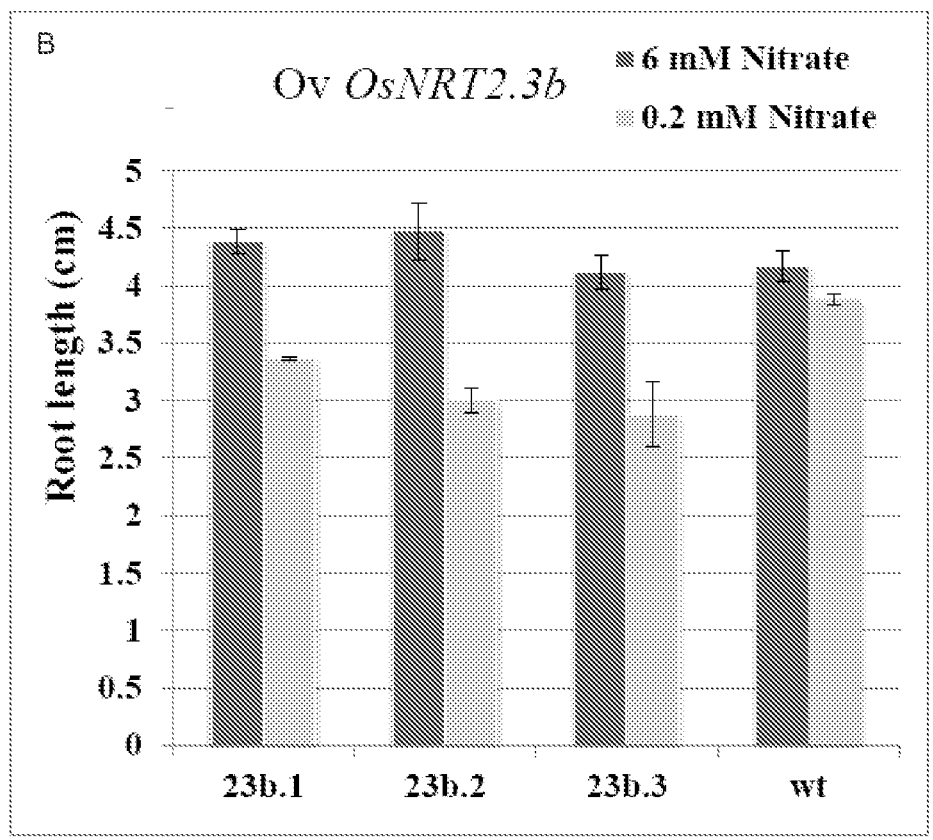

Figure 7
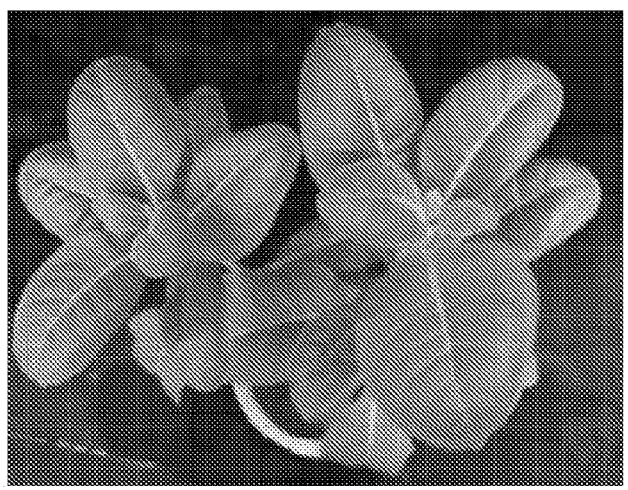

Figure 8A-B

Figure 9
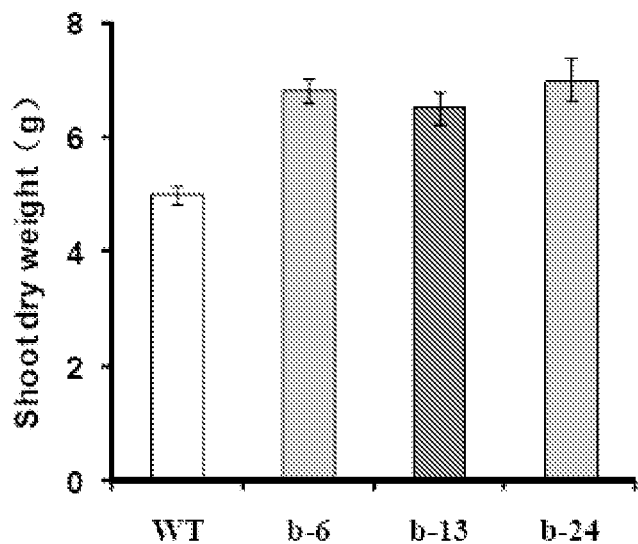
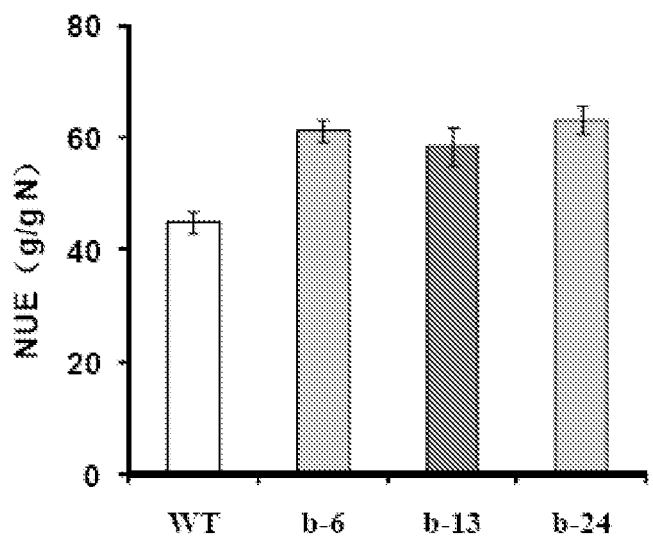

Figure 10

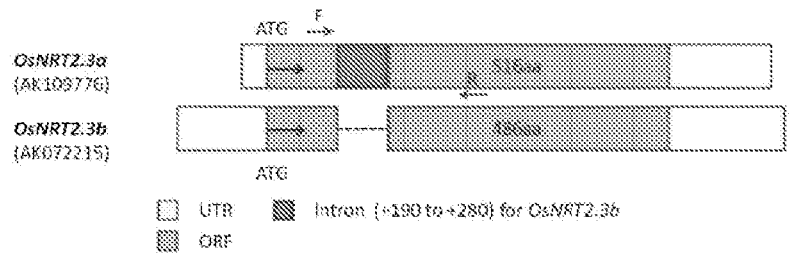

☐ UTR  ▨ Intron (+190 to +280) for OsNRT2.3b
▧ ORF

| | | |
|---|---|---|
| OsNRT2.3a | MEAKPVAMEVEGVEAAGGKPRFRMPVDSDLKATEFWLFSFARPHMASFHMAWFSFFCCFV | 60 |
| OsNRT2.3b | MEAKPVAMEVEGVEAAGGKPRFRMPVDSDLKATEFWLFSFARPHMASFHMAWFSFFCCFV | |
| Consensus | MEAKPVAMEVEGVEAAGGKPRFRMPVDSDLKATEFWLFSFARPHMASFHMAWFSFFCCFV | 60 |

| | | |
|---|---|---|
| OsNRT2.3a | STFAAPPLLPLIRDTLGLTATDIGNAGIASVSGAVFARLAMGTACDLVGPRLASASLILL | 120 |
| OsNRT2.3b | STF                              AVFARLAMGTACDLVGPRLASASLILL | |
| Consensus | STF------------------------------AVFARLAMGTACDLVGPRLASASLILL | 90 |

| | | |
|---|---|---|
| OsNRT2.3a | TTPAVYCSSIIQSPSGYLLVRFFTGISLASFVSAQFWMSSMFSAPKVGLANGVAGGWGNL | 180 |
| OsNRT2.3b | TTPAVYCSSIIQSPSGYLLVRFFTGISLASFVSAQFWMSSMFSAPKVGLANGVAGGWGNL | |
| Consensus | TTPAVYCSSIIQSPSGYLLVRFFTGISLASFVSAQFWMSSMFSAPKVGLANGVAGGWGNL | 150 |

| | | |
|---|---|---|
| OsNRT2.3a | GGGAVQLLMPLVYEAIHKIGSTPFTAWRIAFFIPGLMQTFSAIAVLAFGQDMPGGNYGKL | 240 |
| OsNRT2.3b | GGGAVQLLMPLVYEAIHKIGSTPFTAWRIAFFIPGLMQTFSAIAVLAFGQDMPGGNYGKL | |
| Consensus | GGGAVQLLMPLVYEAIHKIGSTPFTAWRIAFFIPGLMQTFSAIAVLAFGQDMPGGNYGKL | 210 |

| | | |
|---|---|---|
| OsNRT2.3a | HKTGDMHKDSFGNVLRHALTNYRGWILALTYGYSFGVELTIDNVVHQYFYDRFDVNLQTA | 300 |
| OsNRT2.3b | HKTGDMHKDSFGNVLRHALTNYRGWILALTYGYSFGVELTIDNVVHQYFYDRFDVNLQTA | |
| Consensus | HKTGDMHKDSFGNVLRHALTNYRGWILALTYGYSFGVELTIDNVVHQYFYDRFDVNLQTA | 270 |

| | | |
|---|---|---|
| OsNRT2.3a | GLIAASFGMANIISRPGGGLLSDWLSSRYGMRGRLWGLWTVQTIGGVLCVVLGIVDFSFA | 360 |
| OsNRT2.3b | GLIAASFGMANIISRPGGGLLSDWLSSRYGMRGRLWGLWTVQTIGGVLCVVLGIVDFSFA | |
| Consensus | GLIAASFGMANIISRPGGGLLSDWLSSRYGMRGRLWGLWTVQTIGGVLCVVLGIVDFSFA | 330 |

| | | |
|---|---|---|
| OsNRT2.3a | ASVAVMVLFSFFVQAACGLTFGIVPFVSRRSLGLISGMTGGGGNVGAVLTQYIFFHGTKY | 420 |
| OsNRT2.3b | ASVAVMVLFSFFVQAACGLTFGIVPFVSRRSLGLISGMTGGGGNVGAVLTQYIFFHGTKY | |
| Consensus | ASVAVMVLFSFFVQAACGLTFGIVPFVSRRSLGLISGMTGGGGNVGAVLTQYIFFHGTKY | 390 |

| | | |
|---|---|---|
| OsNRT2.3a | KTETGIKYMGLMIIACTLPVMLIYFPQWGGMLVGPRKGATAEEYYSREWSDHEREKGFNA | 480 |
| OsNRT2.3b | KTETGIKYMGLMIIACTLPVMLIYFPQWGGMLVGPRKGATAEEYYSREWSDHEREKGFNA | |
| Consensus | KTETGIKYMGLMIIACTLPVMLIYFPQWGGMLVGPRKGATAEEYYSREWSDHEREKGFNA | 450 |

| | | |
|---|---|---|
| OsNRT2.3a | ASVRFAENSVREGGRSSANGGQPRHTVPVDASPAGV | 516 |
| OsNRT2.3b | ASVRFAENSVREGGRSSANGGQPRHTVPVDASPAGV | |
| Consensus | ASVRFAENSVREGGRSSANGGQPRHTVPVDASPAGV | 486 |

Figure 11A-F
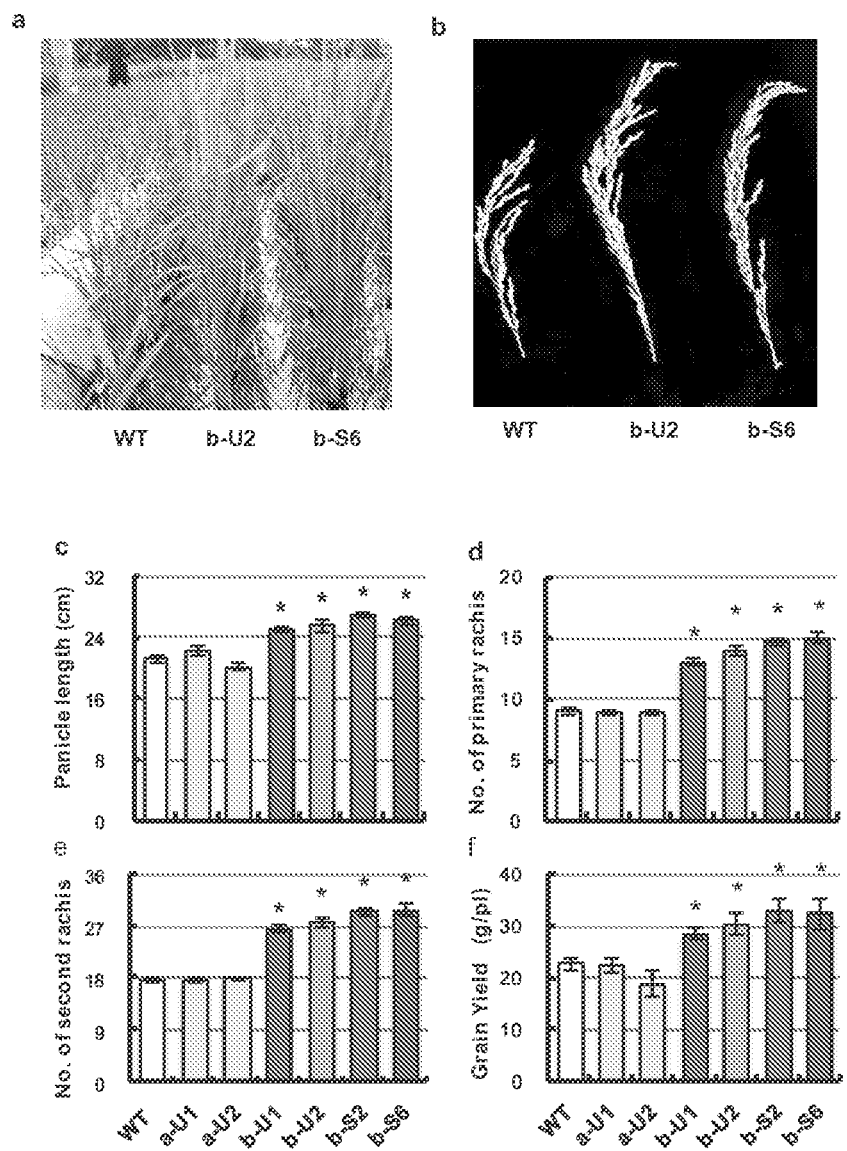

Figure 12A-D
a
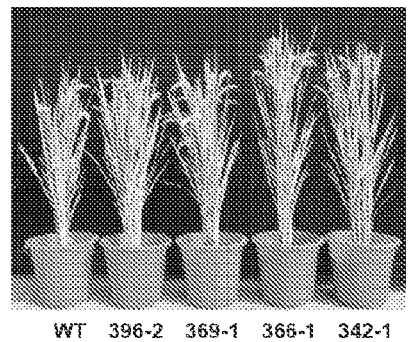
b
HindIII + BamHI
c
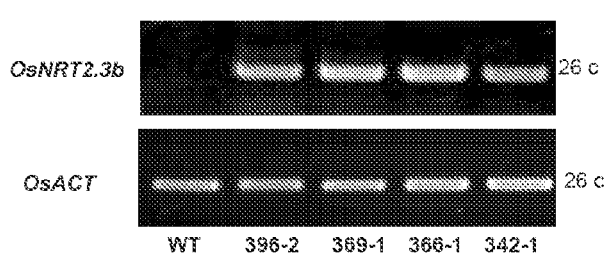
d
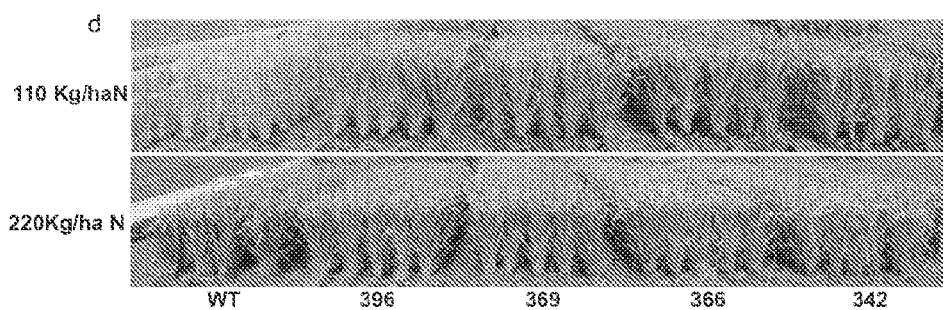

Figure 12E-F
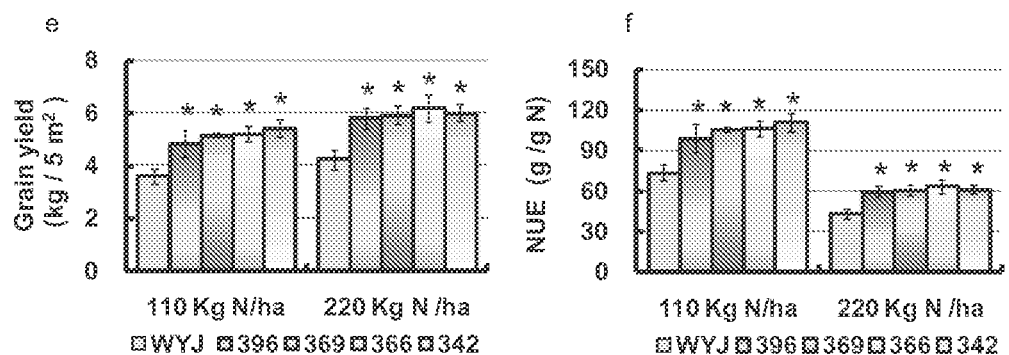
Figure 13A-B
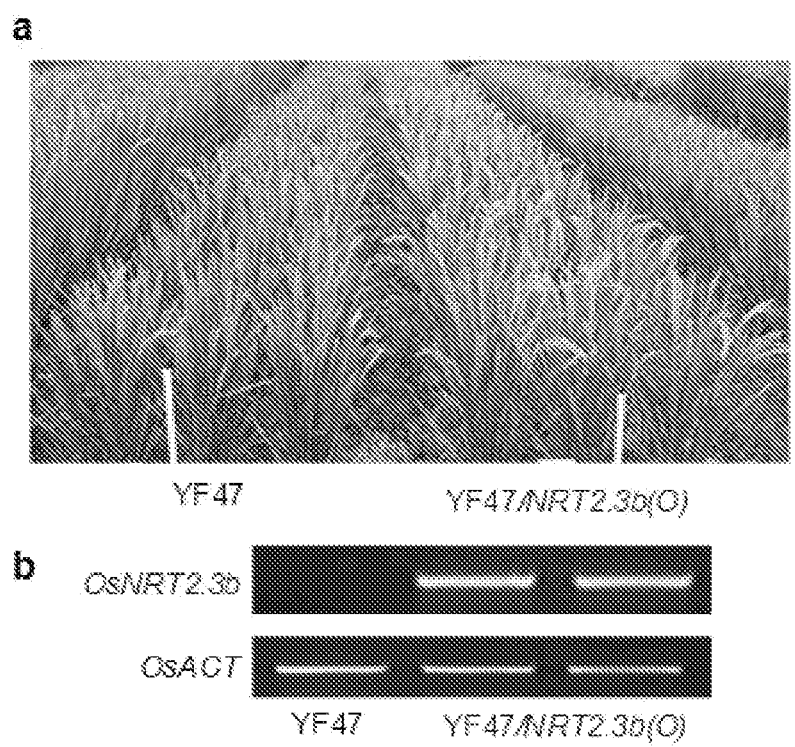

Figure 13C-D
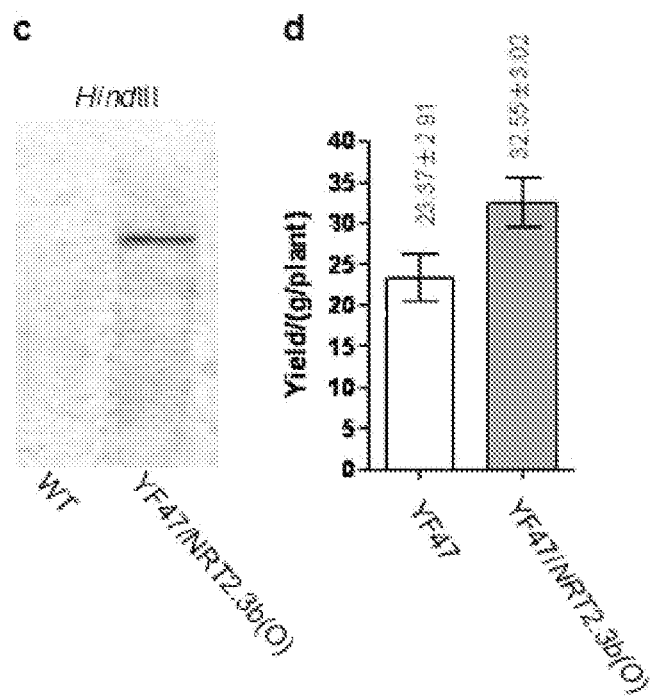
Figure 14A
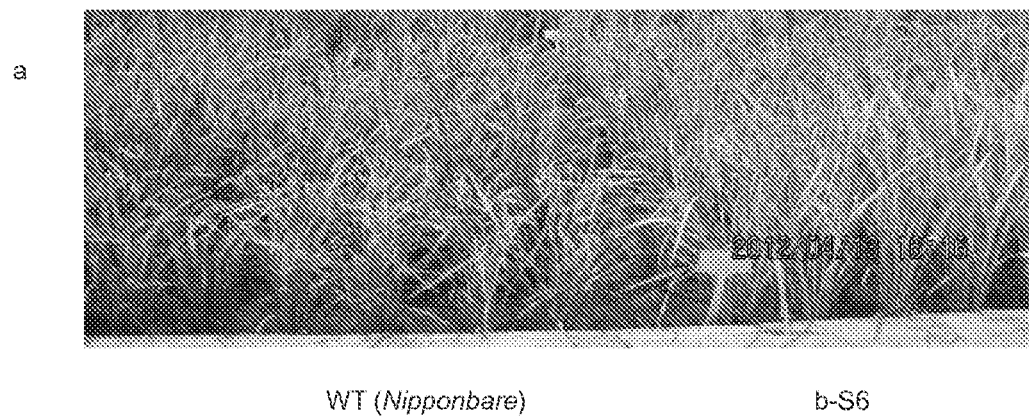
WT (Nipponbare)　　　　　　b-S6

| Genotype | aa | Aa | Aa | AA |
|---|---|---|---|---|
| Copy number | 0.05 | 0.98 | 1.22 | 1.93 |

Figure 16A-F
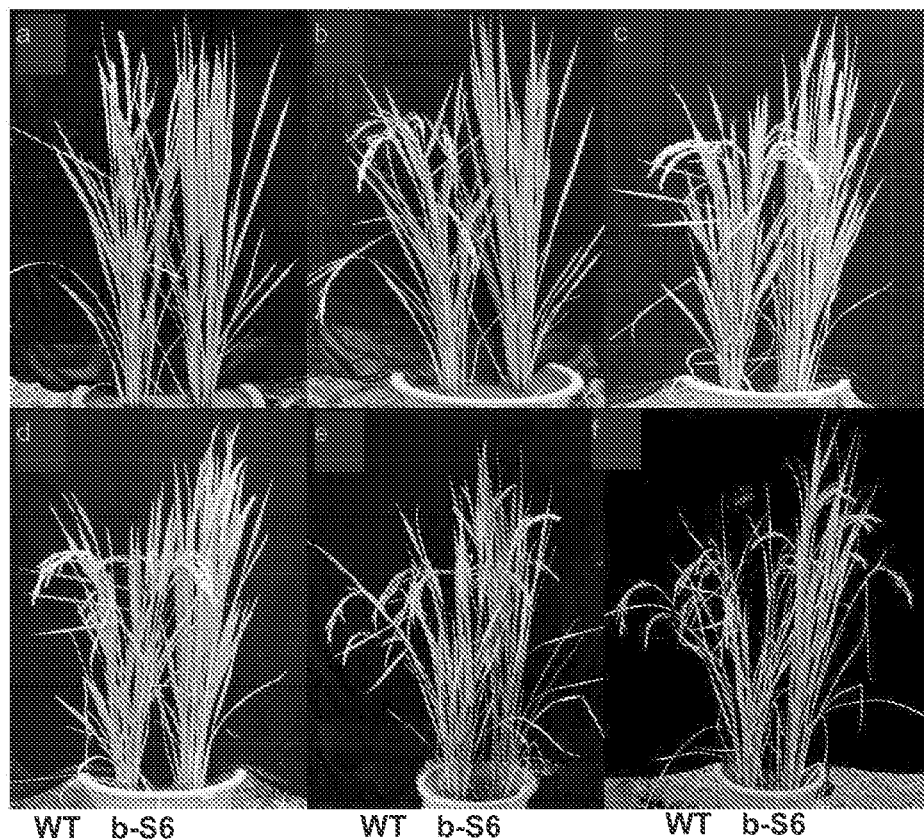

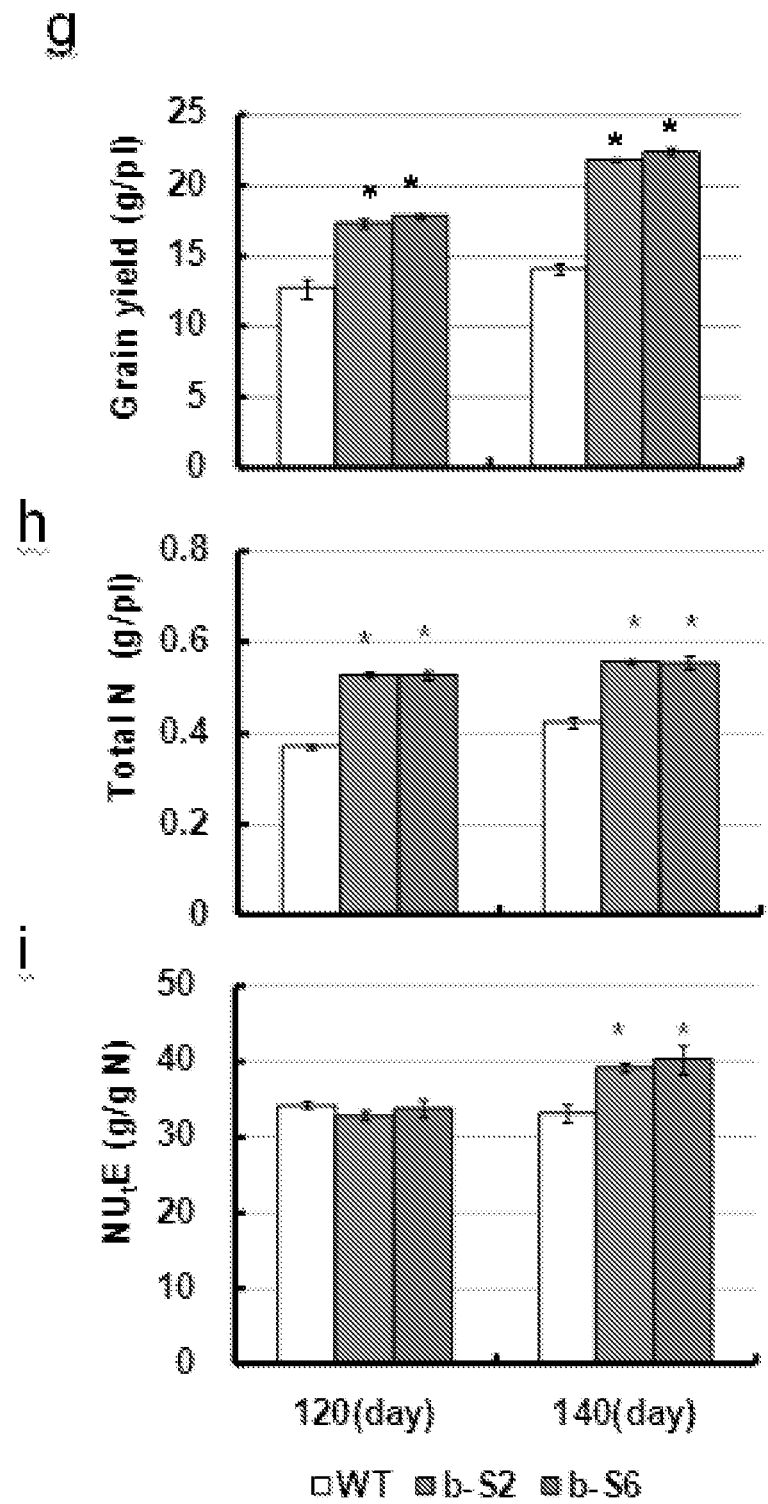
Figure 16G-I

Figure 17A-B
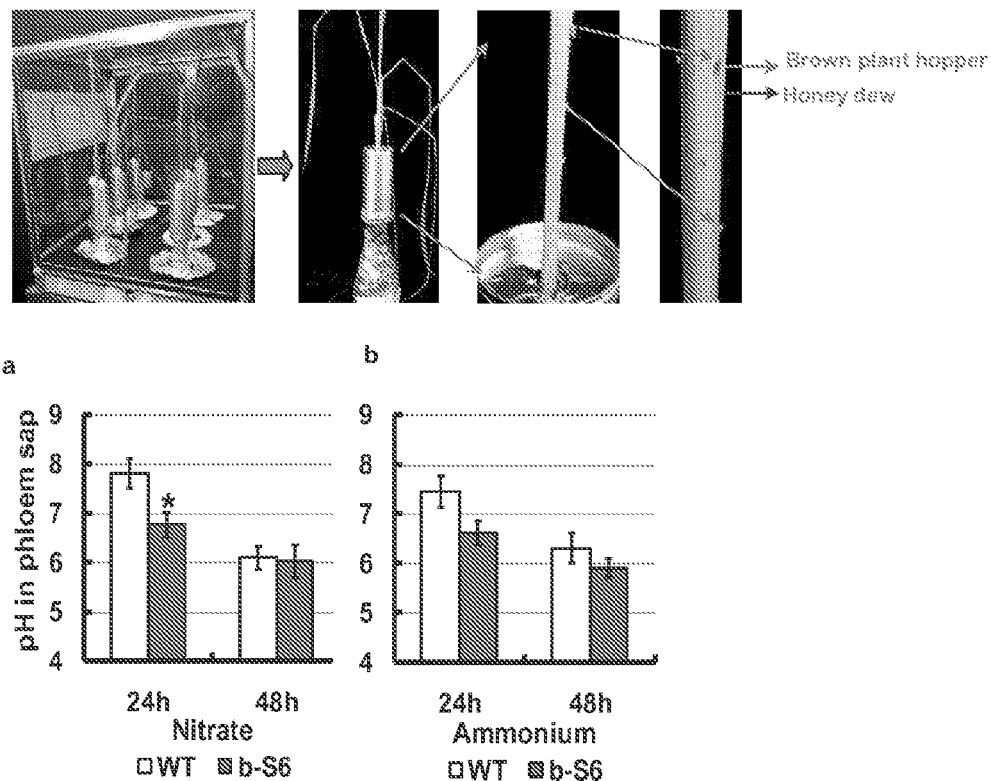
Figure 18A-B
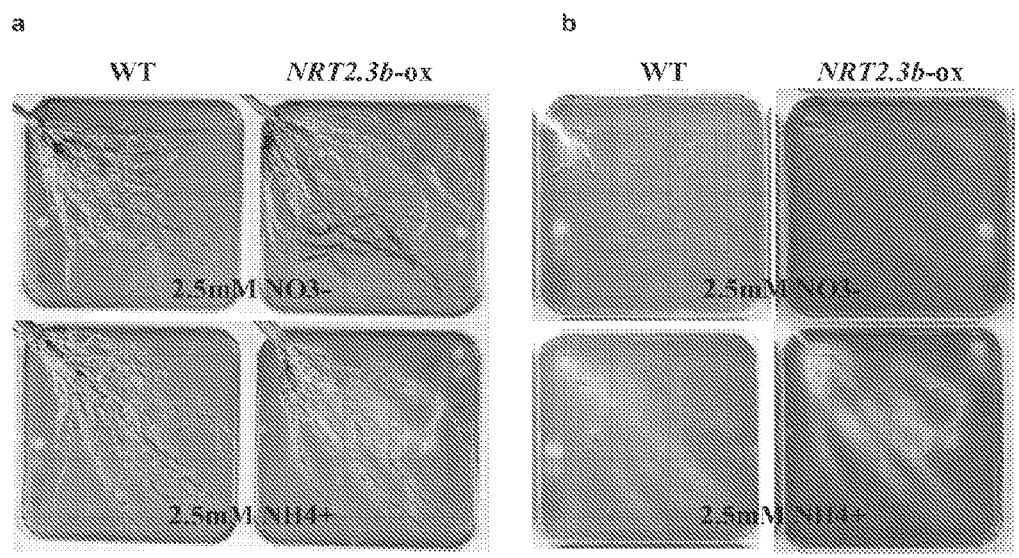

Figure 20A-C
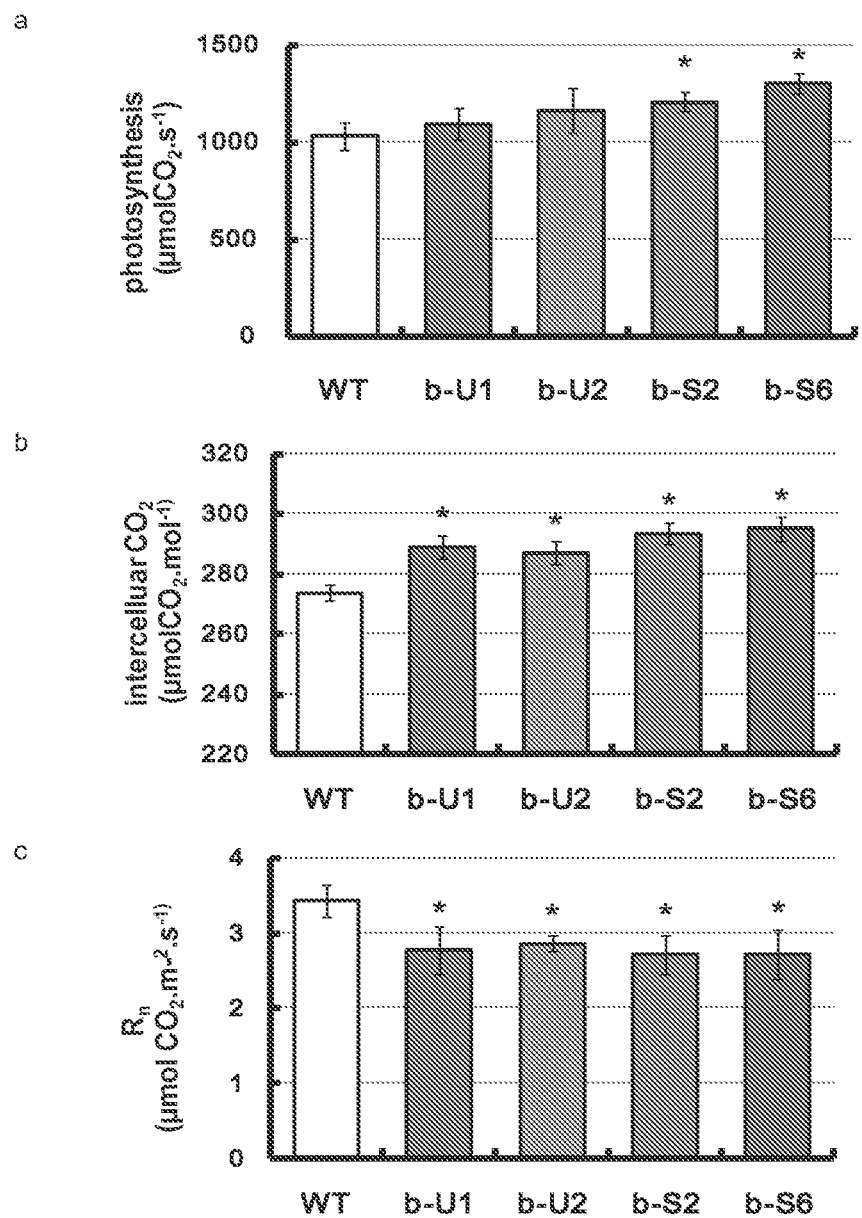

Figure 21A-B
a
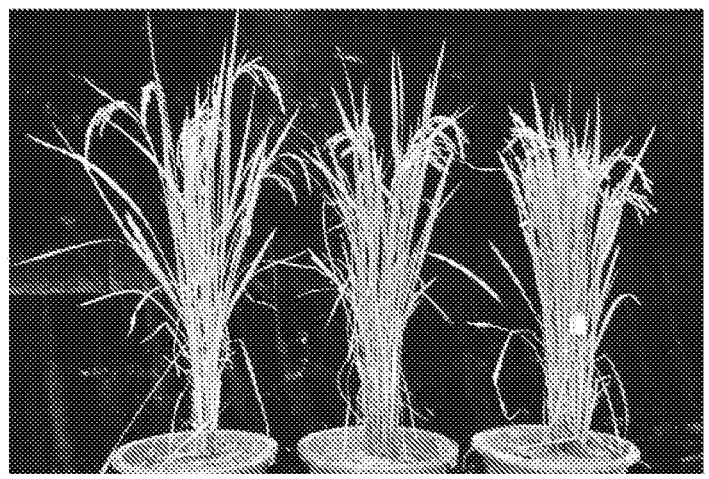
b
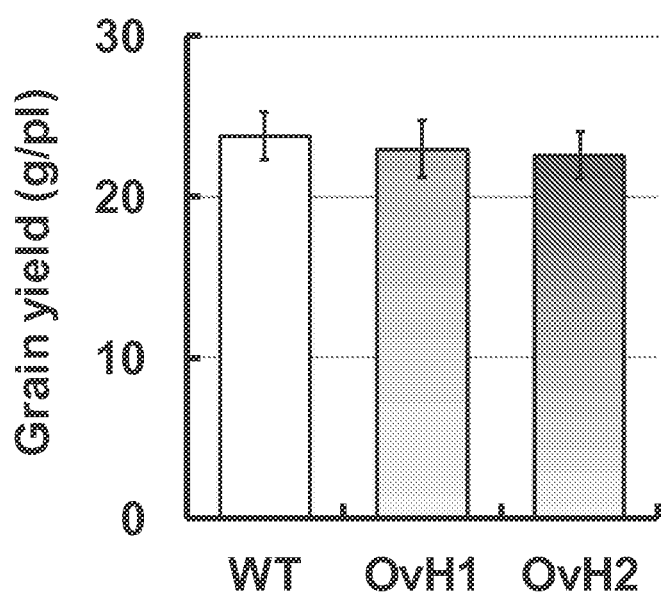

Figure 21C-D
c
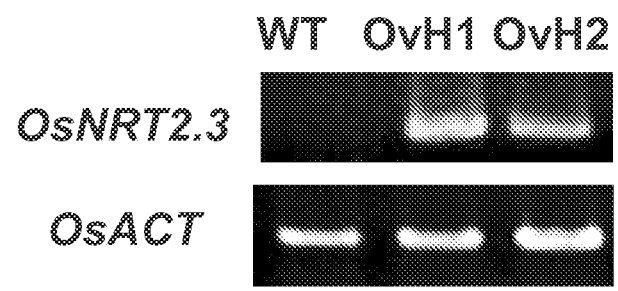
d
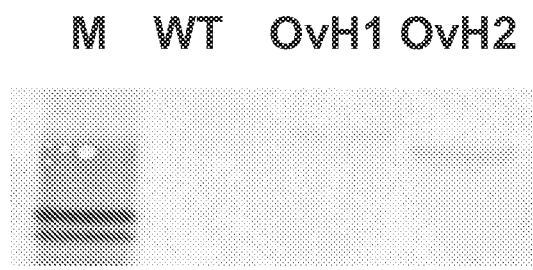
Figure 22
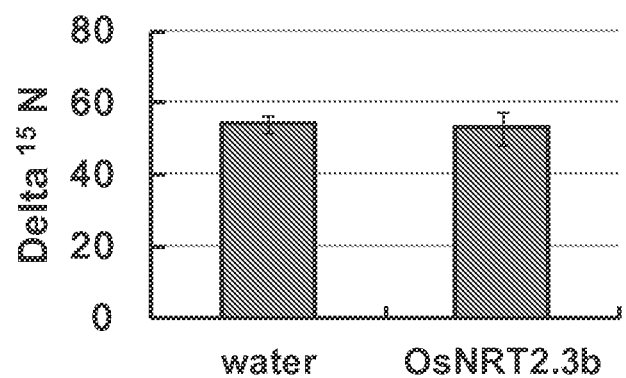

Figure 23A-D
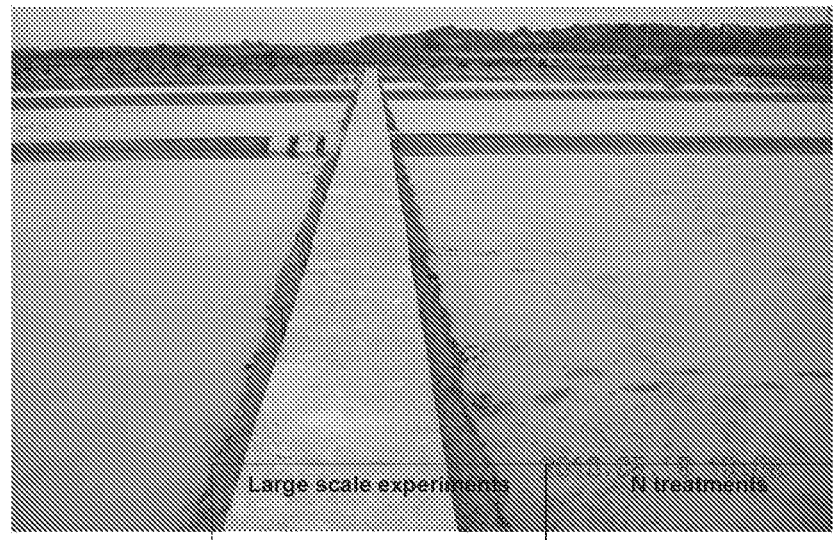

Figure 24A

| Common name | Species | Id number | Motif 1 | Location 1 | Motif 2 | Location 2 |
|---|---|---|---|---|---|---|
| Arabidopsis (AtNRT2.7) | Arabidopsis thaliana | AT5G14570 | FFVGFSLANF SEQ ID No. 41 | 136 | EILIGGLGN SEQ ID No. 42 | 259 |
| A. lyrata | Arabidopsis lyrata | 350602 | FFVGFSLANF SEQ ID No. 43 | 136 | EILIGGLGN SEQ ID No. 44 | 259 |
| Shepherd's purse | Capsella rubella | Carubv10008932m.g | FFVGFSLANF SEQ ID No. 45 | 136 | EILIGGLGN SEQ ID No. 46 | 251 |
|  |  | Carubv10011028m | FSVASPI SEQ ID No. 47 | 24 | LWIIQTAGG SEQ ID No. 48 | 355 |
| Poplar | Populus trichocarpa | Potri.009G008500 | FSVASPI SEQ ID No. 49 | 24 | LWIIQTAGG SEQ ID No. 50 | 355 |
|  |  | Potri.009G008600 | FSVASPI SEQ ID No. 51 | 20 | LWIIQTAGG SEQ ID No. 52 | 351 |
| Cucumber | Cucumis sativus | Cucsa.268720 | WRIAFFVPGF SEQ ID No. 53 | 213 | LWILQTLGGVF SEQ ID No. 54 | 344 |
| Apple | Malus domestica | MDP0000239537 | FSVASPI SEQ ID No. 55 | 24 | LWIIQTAGG SEQ ID No. 56 | 335 |
| Peach | Prunus persica | ppa004104m.g | FSVASPI SEQ ID No. 57 | 24 | LWIIQTAGG SEQ ID No. 58 | 355 |
| Soybean | Glycine max | Glyma13g39850 | WRIAFFVPGF SEQ ID No. 59 | 224 | LWILQTLGGVF SEQ ID No. 60 | 355 |
|  |  | Glyma12g30050 | WRIAFFVPGF SEQ ID No 61 | 224 | LWILQTLGGVF SEQ ID No. 62 | 355 |

| Common name | Species | Id number | Motif 1 | Location 1 | Motif 2 | Location 2 |
|---|---|---|---|---|---|---|
| Purple false brome | Brachypodium distachyon | Bradi2g47640 | FFIPGVM QTF SEQ ID No. 63 | 209 | LWVVQTIG G SEQ ID No. 64 | 336 |
| Barley | Hordeum vulgare | MLOC_75087.1* | FFIPGVM QTF SEQ ID No. 65 | 209 | LWVVQTIG G SEQ ID No. 66 | 336 |
| Maize | Zea mays | GRMZM2G455124* | | | | |
| Wheat | Triticum aestivum | contig276340* | | | | |
| | | contig14141 | | | | |
| | | contig2095384 | | | | |

SEQUENCE LISTING

```
<160> NUMBER OF SEQ ID NOS: 68

<210> SEQ ID NO 1
<211> LENGTH: 1461
<212> TYPE: DNA
<213> ORGANISM: Oryza sativa
<220> FEATURE:
<223> OTHER INFORMATION: OsNRT2.3b Accession NO: AK072215

<400> SEQUENCE: 1
atggaggcta agccggtggc gatggaggtg gaggggggtcg aggcggcggg gggcaagccg      60
cggttcagga tgccggtgga ctccgacctc aaggcgacgg agttctggct cttctccttc     120
gcgaggccac acatggcctc cttccacatg gcgtggttct ccttcttctg ctgcttcgtg     180
tccacgttcg ccgtgttcgc gcgtctggcc atgggcacgg cgtgcgacct ggtcgggccc     240
aggctggcct ccgcgtctct gatcctcctc accacaccgg cggtgtactg ctcctccatc     300
atccagtccc cgtcggggta cctcctcgtg cgcttcttca cgggcatctc gctggcgtcg     360
ttcgtgtcgg cgcagttctg gatgagctcc atgttctcgg cccccaaagt ggggctggcc     420
aacggcgtgg ccggcggctg gggcaacctc ggcggcggcg ccgtccagct gctcatgccg     480
```

| | |
|---|---|
| ctcgtgtacg aggccatcca caagatcggt agcacgccgt tcacggcgtg gcgcatcgcc | 540 |
| ttcttcatcc cgggcctgat gcagacgttc tcggccatcg ccgtgctggc gttcgggcag | 600 |
| gacatgcccg gcggcaacta cgggaagctc acaagactg gcgacatgca aaggacagc | 660 |
| ttcggcaacg tgctgcgcca cgccctcacc aactaccgcg gctggatcct ggcgctcacc | 720 |
| tacggctaca gcttcggcgt cgagctcacc atcgacaacg tcgtgcacca gtacttctac | 780 |
| gaccgcttcg acgtcaacct ccagaccgcc gggctcatcg ccgccagctt cgggatggcc | 840 |
| aacatcatct cccgccccgg cggcgggcta ctctccgact ggctctccag ccggtacggc | 900 |
| atgcgcggca ggctgtgggg gctgtggact gtgcagacca tcggcggcgt cctctgcgtg | 960 |
| gtgctcggaa tcgtcgactt ctccttcgcc gcgtccgtcg ccgtgatggt gctcttctcc | 1020 |
| ttcttcgtcc aggccgcgtg cgggctcacc ttcggcatcg tgccgttcgt gtcgcggagg | 1080 |
| tcgctggggc tcatctccgg gatgaccggc ggcggggggca acgtgggcgc cgtgctgacg | 1140 |
| cagtacatct tcttccacgg cacaaagtac aagacggaga ccgggatcaa gtacatgggg | 1200 |
| ctcatgatca tcgcgtgcac gctgcccgtc atgctcatct acttcccgca gtggggcggc | 1260 |
| atgctcgtag gcccgaggaa gggggccacg gcggaggagt actacagccg ggagtggtcg | 1320 |
| gatcacgagc gcgagaaggg tttcaacgcg ccagcgtgc ggttcgcgga aacagcgtg | 1380 |
| cgcgagggcg ggaggtcgtc ggcgaatggc ggacagccca ggcacaccgt ccccgtcgac | 1440 |
| gcgtcgccgg ccgggggtgtg a | 1461 |

<210> SEQ ID NO 2
<211> LENGTH: 1551
<212> TYPE: DNA
<213> ORGANISM: Oryza sativa
<220> FEATURE:
<223> OTHER INFORMATION: OsNRT2.3a Accession No: AK109776

<400> SEQUENCE: 2

| | |
|---|---|
| atggaggcta agccggtggc gatggaggtg gaggggtcg aggcggcggg gggcaagccg | 60 |
| cggttcagga tgccggtgga ctccgacctc aaggcgacgg agttctggct cttctccttc | 120 |
| gcgaggccac acatggcctc cttccacatg gcgtggttct ccttcttctg ctgcttcgtg | 180 |
| tccacgttcg ccgcgccgcc gctgctgccg ctcatccgcg acaccctcgg gctcacggcc | 240 |
| acggacatcg gcaacgccgg gatcgcgtcc gtgtcgggcg ccgtgttcgc gcgtctggcc | 300 |
| atgggcacgg cgtgcgacct ggtcgggccc aggctggcct ccgcgtctct gatcctcctc | 360 |
| accacaccgg cggtgtactg ctcctccatc atccagtccc cgtcggggta cctcctcgtg | 420 |
| cgcttcttca cgggcatctc gctggcgtcg ttcgtgtcgg cgcagttctg gatgagctcc | 480 |
| atgttctcgg cccccaaagt ggggctggcc aacggcgtgg ccggcggctg gggcaacctc | 540 |
| ggcggcggcg ccgtccagct gctcatgccg ctcgtgtacg aggccatcca caagatcggt | 600 |
| agcacgccgt tcacggcgtg gcgcatcgcc ttcttcatcc cgggcctgat gcagacgttc | 660 |
| tcggccatcg ccgtgctggc gttcgggcag gacatgcccg gcggcaacta cgggaagctc | 720 |
| cacaagactg gcgacatgca aaggacagc ttcggcaacg tgctgcgcca cgccctcacc | 780 |
| aactaccgcg gctggatcct ggcgctcacc tacggctaca gcttcggcgt cgagctcacc | 840 |
| atcgacaacg tcgtgcacca gtacttctac gaccgcttcg acgtcaacct ccagaccgcc | 900 |
| gggctcatcg ccgccagctt cgggatggcc aacatcatct cccgccccgg cggcgggcta | 960 |
| ctctccgact ggctctccag ccggtacggc atgcgcggca ggctgtgggg gctgtggact | 1020 |
| gtgcagacca tcggcggcgt cctctgcgtg gtgctcggaa tcgtcgactt ctccttcgcc | 1080 |

```
gcgtccgtcg ccgtgatggt gctcttctcc ttcttcgtcc aggccgcgtg cgggctcacc    1140
ttcggcatcg tgccgttcgt gtcgcggagg tcgctggggc tcatctccgg gatgaccggc    1200
ggcgggggca acgtgggcgc cgtgctgacg cagtacatct tcttccacgg cacaaagtac    1260
aagacggaga ccgggatcaa gtacatgggg ctcatgatca tcgcgtgcac gctgcccgtc    1320
atgctcatct acttcccgca gtggggcggc atgctcgtag ccccgaggaa ggggggccacg    1380 gcggaggagt actacagccg ggagtggtcg gatcacgagc gcgagaaggg tttcaacgcg    1440
gccagcgtgc ggttcgcgga aacagcgtg cgcgagggcg ggaggtcgtc ggcgaatggc    1500
ggacagccca ggcacaccgt ccccgtcgac gcgtcgccgg ccggggtgtg a             1551
```

<210> SEQ ID NO 3
<211> LENGTH: 486
<212> TYPE: PRT
<213> ORGANISM: Oryza sativa
<220> FEATURE:
<223> OTHER INFORMATION: OsNRT2.3b amino acid sequence

<400> SEQUENCE: 3

```
Met Glu Ala Lys Pro Val Ala Met Glu Val Glu Gly Val Glu Ala Ala
1               5                   10                  15

Gly Gly Lys Pro Arg Phe Arg Met Pro Val Asp Ser Asp Leu Lys Ala
            20                  25                  30

Thr Glu Phe Trp Leu Phe Ser Phe Ala Arg Pro His Met Ala Ser Phe
        35                  40                  45

His Met Ala Trp Phe Ser Phe Phe Cys Cys Phe Val Ser Thr Phe Ala
    50                  55                  60

Val Phe Ala Arg Leu Ala Met Gly Thr Ala Cys Asp Leu Val Gly Pro
65                  70                  75                  80

Arg Leu Ala Ser Ala Ser Leu Ile Leu Leu Thr Thr Pro Ala Val Tyr
                85                  90                  95

Cys Ser Ser Ile Ile Gln Ser Pro Ser Gly Tyr Leu Leu Val Arg Phe
            100                 105                 110

Phe Thr Gly Ile Ser Leu Ala Ser Phe Val Ser Ala Gln Phe Trp Met
        115                 120                 125

Ser Ser Met Phe Ser Ala Pro Lys Val Gly Leu Ala Asn Gly Val Ala
    130                 135                 140

Gly Gly Trp Gly Asn Leu Gly Gly Gly Ala Val Gln Leu Leu Met Pro
145                 150                 155                 160

Leu Val Tyr Glu Ala Ile His Lys Ile Gly Ser Thr Pro Phe Thr Ala
                165                 170                 175

Trp Arg Ile Ala Phe Phe Ile Pro Gly Leu Met Gln Thr Phe Ser Ala
            180                 185                 190

Ile Ala Val Leu Ala Phe Gly Gln Asp Met Pro Gly Gly Asn Tyr Gly
        195                 200                 205

Lys Leu His Lys Thr Gly Asp Met His Lys Asp Ser Phe Gly Asn Val
    210                 215                 220

Leu Arg His Ala Leu Thr Asn Tyr Arg Gly Trp Ile Leu Ala Leu Thr
225                 230                 235                 240

Tyr Gly Tyr Ser Phe Gly Val Glu Leu Thr Ile Asp Asn Val Val His
                245                 250                 255

Gln Tyr Phe Tyr Asp Arg Phe Asp Val Asn Leu Gln Thr Ala Gly Leu
            260                 265                 270

Ile Ala Ala Ser Phe Gly Met Ala Asn Ile Ile Ser Arg Pro Gly Gly
```

-continued

```
                275                 280                 285
Gly Leu Leu Ser Asp Trp Leu Ser Ser Arg Tyr Gly Met Arg Gly Arg
    290                 295                 300

Leu Trp Gly Leu Trp Thr Val Gln Thr Ile Gly Gly Val Leu Cys Val
305                 310                 315                 320

Val Leu Gly Ile Val Asp Phe Ser Phe Ala Ala Ser Val Ala Val Met
                    325                 330                 335

Val Leu Phe Ser Phe Phe Val Gln Ala Ala Cys Gly Leu Thr Phe Gly
                340                 345                 350

Ile Val Pro Phe Val Ser Arg Arg Ser Leu Gly Leu Ile Ser Gly Met
                355                 360                 365

Thr Gly Gly Gly Gly Asn Val Gly Ala Val Leu Thr Gln Tyr Ile Phe
    370                 375                 380

Phe His Gly Thr Lys Tyr Lys Thr Glu Thr Gly Ile Lys Tyr Met Gly
385                 390                 395                 400

Leu Met Ile Ile Ala Cys Thr Leu Pro Val Met Leu Ile Tyr Phe Pro
                    405                 410                 415

Gln Trp Gly Gly Met Leu Val Gly Pro Arg Lys Gly Ala Thr Ala Glu
                420                 425                 430

Glu Tyr Tyr Ser Arg Glu Trp Ser Asp His Glu Arg Glu Lys Gly Phe
            435                 440                 445

Asn Ala Ala Ser Val Arg Phe Ala Glu Asn Ser Val Arg Glu Gly Gly
        450                 455                 460

Arg Ser Ser Ala Asn Gly Gly Gln Pro Arg His Thr Val Pro Val Asp
465                 470                 475                 480

Ala Ser Pro Ala Gly Val
                485

<210> SEQ ID NO 4
<211> LENGTH: 516
<212> TYPE: PRT
<213> ORGANISM: Oryza sativa
<220> FEATURE:
<223> OTHER INFORMATION: OsNRT2.3a amino acid sequence

<400> SEQUENCE: 4

Met Glu Ala Lys Pro Val Ala Met Glu Val Glu Gly Val Glu Ala Ala
1               5                   10                  15

Gly Gly Lys Pro Arg Phe Arg Met Pro Val Asp Ser Asp Leu Lys Ala
                20                  25                  30

Thr Glu Phe Trp Leu Phe Ser Phe Ala Arg Pro His Met Ala Ser Phe
            35                  40                  45

His Met Ala Trp Phe Ser Phe Phe Cys Cys Phe Val Ser Thr Phe Ala
        50                  55                  60

Ala Pro Pro Leu Leu Pro Leu Ile Arg Asp Thr Leu Gly Leu Thr Ala
65                  70                  75                  80

Thr Asp Ile Gly Asn Ala Gly Ile Ala Ser Val Ser Gly Ala Val Phe
                85                  90                  95

Ala Arg Leu Ala Met Gly Thr Ala Cys Asp Leu Val Gly Pro Arg Leu
                100                 105                 110

Ala Ser Ala Ser Leu Ile Leu Leu Thr Thr Pro Ala Val Tyr Cys Ser
            115                 120                 125

Ser Ile Ile Gln Ser Pro Ser Gly Tyr Leu Leu Val Arg Phe Phe Thr
        130                 135                 140

Gly Ile Ser Leu Ala Ser Phe Val Ser Ala Gln Phe Trp Met Ser Ser
```

```
                145                 150                 155                 160
Met Phe Ser Ala Pro Lys Val Gly Leu Ala Asn Gly Val Ala Gly Gly
                    165                 170                 175

Trp Gly Asn Leu Gly Gly Gly Ala Val Gln Leu Leu Met Pro Leu Val
            180                 185                 190

Tyr Glu Ala Ile His Lys Ile Gly Ser Thr Pro Phe Thr Ala Trp Arg
        195                 200                 205

Ile Ala Phe Phe Ile Pro Gly Leu Met Gln Thr Phe Ser Ala Ile Ala
    210                 215                 220

Val Leu Ala Phe Gly Gln Asp Met Pro Gly Asn Tyr Gly Lys Leu
225                 230                 235                 240

His Lys Thr Gly Asp Met His Lys Asp Ser Phe Gly Asn Val Leu Arg
                245                 250                 255

His Ala Leu Thr Asn Tyr Arg Gly Trp Ile Leu Ala Leu Thr Tyr Gly
            260                 265                 270

Tyr Ser Phe Gly Val Glu Leu Thr Ile Asp Asn Val Val His Gln Tyr
        275                 280                 285

Phe Tyr Asp Arg Phe Asp Val Asn Leu Gln Thr Ala Gly Leu Ile Ala
    290                 295                 300

Ala Ser Phe Gly Met Ala Asn Ile Ile Ser Arg Pro Gly Gly Gly Leu
305                 310                 315                 320

Leu Ser Asp Trp Leu Ser Ser Arg Tyr Gly Met Arg Gly Arg Leu Trp
                325                 330                 335

Gly Leu Trp Thr Val Gln Thr Ile Gly Gly Val Leu Cys Val Val Leu
            340                 345                 350

Gly Ile Val Asp Phe Ser Phe Ala Ala Ser Val Ala Val Met Val Leu
        355                 360                 365

Phe Ser Phe Phe Val Gln Ala Ala Cys Gly Leu Thr Phe Gly Ile Val
    370                 375                 380

Pro Phe Val Ser Arg Arg Ser Leu Gly Leu Ile Ser Gly Met Thr Gly
385                 390                 395                 400

Gly Gly Gly Asn Val Gly Ala Val Leu Thr Gln Tyr Ile Phe Phe His
                405                 410                 415

Gly Thr Lys Tyr Lys Thr Glu Thr Gly Ile Lys Tyr Met Gly Leu Met
            420                 425                 430

Ile Ile Ala Cys Thr Leu Pro Val Met Leu Ile Tyr Phe Pro Gln Trp
        435                 440                 445

Gly Gly Met Leu Val Gly Pro Arg Lys Gly Ala Thr Ala Glu Glu Tyr
    450                 455                 460

Tyr Ser Arg Glu Trp Ser Asp His Glu Arg Glu Lys Gly Phe Asn Ala
465                 470                 475                 480

Ala Ser Val Arg Phe Ala Glu Asn Ser Val Arg Glu Gly Gly Arg Ser
                485                 490                 495

Ser Ala Asn Gly Gly Gln Pro Arg His Thr Val Pro Val Asp Ala Ser
            500                 505                 510

Pro Ala Gly Val
        515

<210> SEQ ID NO 5
<211> LENGTH: 1759
<212> TYPE: DNA
<213> ORGANISM: Oryza sativa
<220> FEATURE:
<223> OTHER INFORMATION: Phloem promoter sequence nucleotides 61 to 1819
```

<400> SEQUENCE: 5

```
caaatgtgca atgctgatta gagtttgcag atgctgtttg gtttagttta gatgtggcat      60
tttgttagtg gtttctttga tgaaaaattc ttggctatga taaagtttgc tttctgaata     120
tatgaatagt ggccatggtt caagaaactc cagttaggtg ggataattta tggtgattct     180
gggcgcaatt cggggaaatt ttttttggcg agaatcttat cattgagata agagggcaa      240
gaatatcaac agacttttaa tcttaataaa aagcactctt agcgtaagag caaagcattg     300
caatctcgtg tgacaagaac gtttcttttt ctccatcttt ttcttttta ccaaaaaatg      360
agtgttgcca actgctgcac cttcttaggc cggtttgttc ttgtttggaa cgcacggaat     420
gcccgatgca aaaaaaaaa agaaatgctg ttaacaaatc actgtcctga cacggctaat     480
taggtggtaa tttggtgcat ctgcaaagaa gcaacagatg ctttctttca ctgaaagcat     540
atttgcatga tttcttgttt ctgcttgtcc tctctctgat gctgactgta ttccactctg     600
cgctgtaatg ccatgttagt gattaatatg ttcaaaagag cataaaagaa ttgccaattg     660
gatgttagag attactgtgt tgttcaaaag agcataaaag aattaccaat ttgatggtag     720
atgttactag caccaccttg gtgttttccc atggttttct gcaattctgc ccatgatctt     780
tctgcttttc tgaaagacct atgtttcaga ggtcaagctt ctggaaggtt attaggaggg     840
atgagtcgtc attttgtctg tgggccccac tagtcagtgt caatagttgt aaagggtaga     900
aattttcttg ctgttttct tggaaacaat ttcattgcgc ctgatctgat ggtcggtctg      960
gtaatcaaat caccagatcc tgaaatccac caaatcaaac cgtgagattt ttgcagaggc    1020
aaaacaagaa aagcatctgc tttatttctc tcttgctttc ttttcatccc caaccagtcc    1080
ttttttcttc tgtttatttg tagaagtcta ccacctgcag tctattattc tacagagaaa    1140
aagattgaag cttttttttct ccaaagctga caatggtgcc ggcatatgct aataggatac    1200
tcccttcgtc taggaaaaaa ccaacccact acaatttga atatatattt attcagattt     1260
gttatgcttc ctactccttc tcaggtatgg tgagatattt catagtataa tgaatttgga    1320
catatatttg tccaaattca tcgcattatg aaatgtctcg ttcgatctat gttgttatat    1380
tatagacgga gatagtagat tcggttattt ttggacagag aaagtactcg cctgtgctag    1440
tgacatgatt agtgacacca tcagattaaa aaaacatatg ttttgattaa aaaatggg     1500
aatttggggg gagcaataat ttggggttat ccattgctgt tcatcatgt cagctgaaag     1560
gccctaccac taaaccaata tctgtactat tctaccacct atcagaattc agagcactgg    1620
ggttttgcaa ctatttattg gtccttctgg atctcggaga aaccctccat tcgtttgctc    1680
ttaattaaaa gggcaattct gcagatatcc atcacactgg cggccgctcg agcatgcatc    1740
tagaggccca attcgccca                                                  1759
```

<210> SEQ ID NO 6
<211> LENGTH: 1563
<212> TYPE: DNA
<213> ORGANISM: Zea mays
<220> FEATURE:
<223> OTHER INFORMATION: Maize nucleic acid sequence - OsNRT2.3b related gene

<400> SEQUENCE: 6

```
atggcggagg gggagttcaa gcccgcggcg atgcaggtgg aggctcctgc cgaggcggcg     60
gcggcgccgt ccaagccgcg gttcaggatg cccgtcgact ccgacaacaa ggccaccgag    120
ttctggctct ctctccttcgc gaggccgcac atgagcgcct tccacatgtc gtggttctcc    180
```

-continued

```
ttcttctgct gcttcctctc caccttcgcg gcgccgccgc tgctcccgct catccgggac     240
acgctgggc tcacggccac ggacatcggc aacgccggga tcgcctccgt gtccggcgcg     300
gtcttcgcgc gcgtggccat gggcacggcg tgcgacctgg tgggcccgcg cctggcgtcc     360
gcggccatca tactcctcac cacgcccgcc gtctactact ccgccgtcat cgactccgcc     420
tcgtcctacc tgctcgtgcg cttcttcacg ggcttctcgc tcgcgtcctt cgtgtccacg     480
cagttctgga tgagctccat gttctcgccg cccaaggtgg ggctggccaa cggcgtcgcc     540
gggggtggg gcaacctcgg cggcggcgcc gtgcagctca tcatgccgct cgtgttcgag     600
gccatccgca aggccgggc cacgccgttc acggcgtggc gcgtcgcctt cttcgtcccg     660
ggcctgctgc agacgctgtc ggccgtcgcc gtgctggcgt tcggccagga catgcccgac     720
ggcaactacc gcaagctgca caggtccggc gacatgcaca aggacagctt cggcaacgtg     780
ctccgccacg ccgtcaccaa ctaccgcgcc tggatcctgg cgctcaccta cggatactgc     840
ttcggcgtgg agctcgccgt ggacaacatc gtcgcgcagt acttctacga ccgcttcggc     900
gtcaagctca gcaccgccgg cttcatcgcc gccagcttcg gatggccaa catcgtctcc     960
cgccccggcg gcggcctcct gtcggactgg ctctccagcc gcttcggcat gcgcggcagg     1020
ctgtggggcc tgtgggtggt gcagaccatc ggggcgtcc tctgcgtcgt gctcggcgcc     1080
gtcgactact ccttcgccgc gtccgtggcc gtcatgatac tcttctccat gttcgtgcag     1140
gcggcctgcg ggctcacctt tggcatcgtc ccgttcgtct cccgaaggtc gctgggctc     1200
atctccggca tgaccggcgg cggcggcaac gtgggcgccg tgctcacgca gctcatcttc     1260
ttccacggat ccaagtacaa gacggagacg gggatcaagt acatggggtt catgatcatc     1320
gcctgcacgt tgcccatcac gctcatctac ttcccgcagt ggggcggcat gttcctgggg     1380
ccgcggcccg gggcgacggc ggaggactac tacaaccggg agtggacagc gcacgagtgc     1440
gacaagggtt tcaacaccgc gagcgtacgc tttgcggaga acagcgtgcg ggaaggggga     1500
cgctcgggca gccagtccaa gcacactact gtgcccgtcg agtcctcgcc ggccgacgtg     1560
tga                                                                   1563
```

<210> SEQ ID NO 7
<211> LENGTH: 520
<212> TYPE: PRT
<213> ORGANISM: Zea mays
<220> FEATURE:
<223> OTHER INFORMATION: Maize amino acid sequence - OsNRT2.3b related gene

<400> SEQUENCE: 7

```
Met Ala Glu Gly Glu Phe Lys Pro Ala Ala Met Gln Val Glu Ala Pro
1               5                   10                  15

Ala Glu Ala Ala Ala Ala Pro Ser Lys Pro Arg Phe Arg Met Pro Val
            20                  25                  30

Asp Ser Asp Asn Lys Ala Thr Glu Phe Trp Leu Phe Ser Phe Ala Arg
        35                  40                  45

Pro His Met Ser Ala Phe His Met Ser Trp Phe Ser Phe Cys Cys
    50                  55                  60

Phe Leu Ser Thr Phe Ala Ala Pro Pro Leu Leu Pro Leu Ile Arg Asp
65                  70                  75                  80

Thr Leu Gly Leu Thr Ala Thr Asp Ile Gly Asn Ala Gly Ile Ala Ser
                85                  90                  95

Val Ser Gly Ala Val Phe Ala Arg Val Ala Met Gly Thr Ala Cys Asp
            100                 105                 110
```

```
Leu Val Gly Pro Arg Leu Ala Ser Ala Ala Ile Ile Leu Leu Thr Thr
            115                 120                 125

Pro Ala Val Tyr Tyr Ser Ala Val Ile Asp Ser Ala Ser Ser Tyr Leu
        130                 135                 140

Leu Val Arg Phe Phe Thr Gly Phe Ser Leu Ala Ser Phe Val Ser Thr
145                 150                 155                 160

Gln Phe Trp Met Ser Ser Met Phe Ser Pro Pro Lys Val Gly Leu Ala
                165                 170                 175

Asn Gly Val Ala Gly Gly Trp Gly Asn Leu Gly Gly Gly Ala Val Gln
                180                 185                 190

Leu Ile Met Pro Leu Val Phe Glu Ala Ile Arg Lys Ala Gly Ala Thr
                195                 200                 205

Pro Phe Thr Ala Trp Arg Val Ala Phe Phe Val Pro Gly Leu Leu Gln
        210                 215                 220

Thr Leu Ser Ala Val Ala Val Leu Ala Phe Gly Gln Asp Met Pro Asp
225                 230                 235                 240

Gly Asn Tyr Arg Lys Leu His Arg Ser Gly Asp Met His Lys Asp Ser
                245                 250                 255

Phe Gly Asn Val Leu Arg His Ala Val Thr Asn Tyr Arg Ala Trp Ile
                260                 265                 270

Leu Ala Leu Thr Tyr Gly Tyr Cys Phe Gly Val Glu Leu Ala Val Asp
            275                 280                 285

Asn Ile Val Ala Gln Tyr Phe Tyr Asp Arg Phe Gly Val Lys Leu Ser
            290                 295                 300

Thr Ala Gly Phe Ile Ala Ala Ser Phe Gly Met Ala Asn Ile Val Ser
305                 310                 315                 320

Arg Pro Gly Gly Gly Leu Leu Ser Asp Trp Leu Ser Ser Arg Phe Gly
                325                 330                 335

Met Arg Gly Arg Leu Trp Gly Leu Trp Val Val Gln Thr Ile Gly Gly
                340                 345                 350

Val Leu Cys Val Val Leu Gly Ala Val Asp Tyr Ser Phe Ala Ala Ser
            355                 360                 365

Val Ala Val Met Ile Leu Phe Ser Met Phe Val Gln Ala Ala Cys Gly
            370                 375                 380

Leu Thr Phe Gly Ile Val Pro Phe Val Ser Arg Arg Ser Leu Gly Leu
385                 390                 395                 400

Ile Ser Gly Met Thr Gly Gly Gly Asn Val Gly Ala Val Leu Thr
                405                 410                 415

Gln Leu Ile Phe Phe His Gly Ser Lys Tyr Lys Thr Glu Thr Gly Ile
                420                 425                 430

Lys Tyr Met Gly Phe Met Ile Ile Ala Cys Thr Leu Pro Ile Thr Leu
                435                 440                 445

Ile Tyr Phe Pro Gln Trp Gly Gly Met Phe Leu Gly Pro Arg Pro Gly
        450                 455                 460

Ala Thr Ala Glu Asp Tyr Tyr Asn Arg Glu Trp Thr Ala His Glu Cys
465                 470                 475                 480

Asp Lys Gly Phe Asn Thr Ala Ser Val Arg Phe Ala Glu Asn Ser Val
                485                 490                 495

Arg Glu Gly Gly Arg Ser Gly Ser Gln Ser Lys His Thr Thr Val Pro
                500                 505                 510

Val Glu Ser Ser Pro Ala Asp Val
                515                 520
```

<210> SEQ ID NO 8
<211> LENGTH: 1890
<212> TYPE: DNA
<213> ORGANISM: Glycine max
<220> FEATURE:
<223> OTHER INFORMATION: Soybean nucleic acid sequence - OsNRT2.3b related gene

<400> SEQUENCE: 8

| | | | | | |
|---|---|---|---|---|---|
| tcacactttc | ttccttaatt | ttctagctct | tgctacgtac | ttgaattcaa | ttagttatta | 60 |
| atggctgaga | ttgagggttc | tcccggaagc | tccatgcatg | gagtaacagg | aagagaacaa | 120 |
| acatttgtag | cctcagttgc | ttctccaatt | gtccctacag | acaccacagc | caaatttgct | 180 |
| ctcccagtgg | attcagaaca | caaggccaag | gttttcaaac | tcttctccct | ggccaatccc | 240 |
| cacatgagaa | ccttccacct | ttcttggatc | tccttcttca | cctgcttcgt | ctcgacattc | 300 |
| gcagcagcac | ctcttgtgcc | catcatccgc | gacaacctta | acctcaccaa | aagcgacatt | 360 |
| ggaaacgccg | gggttgcttc | tgtctccgga | agcatcttct | caaggctcgc | aatgggtgca | 420 |
| gtctgtgaca | tgttgggtcc | acgctatggc | tgcgccttcc | tcatcatgct | ttcggcccct | 480 |
| acggtgttct | gcatgtcctt | tgtgaaagat | gctgcggggt | acatagcggt | tcggttcttg | 540 |
| attgggttct | cgttggcgac | gtttgtgtcg | tgccagtact | ggatgagcac | gatgttcaac | 600 |
| agtaagatta | tagggcttgc | gaatgggact | gctgcggggt | gggggaacat | gggtggtgga | 660 |
| gccactcagc | tcataatgcc | tttggtgtat | gagcttatca | aagagctgg | ggctactccc | 720 |
| ttcactgctt | ggaggattgc | cttctttgtt | ccgggtttca | tgcatgtcat | catgggatt | 780 |
| cttgtcctca | ctctaggcca | ggacttgcct | gatggaaacc | tcgggccctt | gcggaagaag | 840 |
| ggtgatgtag | ctaaagacaa | gttttccaag | gtgctatggt | atgccataac | aaattacagg | 900 |
| acatggattt | ttgctctcct | ctatgggtac | tccatgggag | ttgaattaac | aactgacaat | 960 |
| gtcattgctg | agtatttcta | tgacagattt | aatctcaagc | tacacactgc | tggaatcatt | 1020 |
| gctgcttcat | ttggaatggc | aaacttagtt | gctcgacctt | ttggtggata | tgcttcagat | 1080 |
| gttgcagcca | ggctgtttgg | catgaggga | agactctgga | ccctttggat | cctccaaacc | 1140 |
| ttaggagggg | ttttctgtat | ttggcttggc | cgtgccaatt | ctcttcctat | tgctgtattg | 1200 |
| gccatgatcc | tgttctctat | aggagctcaa | gctgcatgtg | gtgcaacttt | tggcatcatt | 1260 |
| cctttcatct | caagaaggtc | tttggggatc | atatcaggtc | taactggtgc | aggtggaaac | 1320 |
| tttgggtctg | gcctcaccca | attggtcttc | ttttcaacct | ccaaattctc | tactgccaca | 1380 |
| ggtctctcct | tgatgggtgt | aatgatagtg | gcttgcactc | taccagtgag | tgttgttcac | 1440 |
| ttcccacagt | ggggtagcat | gtttctacca | ccctcaaaag | atgtcagcaa | atccactgaa | 1500 |
| gaattctatt | acacctctga | atggaatgag | gaagagaagc | agaagggttt | gcaccagcaa | 1560 |
| agtctcaaat | ttgctgagaa | tagccgatct | gagagaggaa | agcgagtggc | ttcagcacca | 1620 |
| acacctccaa | atgcaactcc | cactcatgtc | tagccatagc | acttcaatca | agaagatca | 1680 |
| tgaaacataa | ttactgagca | gtattgggaa | tgaagaacca | tgagttgaag | aattttctaa | 1740 |
| taagaaatct | tgtaacatgt | agacatagaa | tgttctggtt | ctggtttgcg | tgtggtgtaa | 1800 |
| gagttgtcta | cttgtggtaa | gtcataagta | tcataatcag | tatgtcaatg | cagatcttga | 1860 |
| tgctgagtat | caatagtatc | aaaaaaaaaa | | | | 1890 |

<210> SEQ ID NO 9
<211> LENGTH: 530
<212> TYPE: PRT

<213> ORGANISM: Glycine max
<220> FEATURE:
<223> OTHER INFORMATION: Soybean amino acid sequence - OsNRT2.3b related gene

<400> SEQUENCE: 9

```
Met Ala Glu Ile Glu Gly Ser Pro Gly Ser Ser Met His Gly Val Thr
1               5                   10                  15

Gly Arg Glu Gln Thr Phe Val Ala Ser Val Ala Ser Pro Ile Val Pro
            20                  25                  30

Thr Asp Thr Ala Lys Phe Ala Leu Pro Val Asp Ser Glu His Lys
        35                  40                  45

Ala Lys Val Phe Lys Leu Phe Ser Leu Ala Asn Pro His Met Arg Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
            100                 105                 110

Phe Ser Arg Leu Ala Met Gly Ala Val Cys Asp Met Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Lys Asp Ala Ala Gly Tyr Ile Ala Val Arg Phe Leu
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Ala Asn Gly Thr Ala Ala
            180                 185                 190

Gly Trp Gly Asn Met Gly Gly Gly Ala Thr Gln Leu Ile Met Pro Leu
        195                 200                 205

Val Tyr Glu Leu Ile Arg Arg Ala Gly Ala Thr Pro Phe Thr Ala Trp
    210                 215                 220

Arg Ile Ala Phe Phe Val Pro Gly Phe Met His Val Ile Met Gly Ile
225                 230                 235                 240

Leu Val Leu Thr Leu Gly Gln Asp Leu Pro Asp Gly Asn Leu Gly Ala
                245                 250                 255

Leu Arg Lys Lys Gly Asp Val Ala Lys Asp Lys Phe Ser Lys Val Leu
            260                 265                 270

Trp Tyr Ala Ile Thr Asn Tyr Arg Thr Trp Ile Phe Ala Leu Leu Tyr
        275                 280                 285

Gly Tyr Ser Met Gly Val Glu Leu Thr Thr Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Ser Phe Gly Met Ala Asn Leu Val Ala Arg Pro Phe Gly Gly
                325                 330                 335

Tyr Ala Ser Asp Val Ala Ala Arg Leu Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Leu Ala Met Ile Leu
    370                 375                 380
```

```
Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Leu Thr Gly
            405                 410                 415

Ala Gly Gly Asn Phe Gly Ser Gly Leu Thr Gln Leu Val Phe Phe Ser
        420                 425                 430

Thr Ser Lys Phe Ser Thr Ala Thr Gly Leu Ser Leu Met Gly Val Met
        435                 440                 445

Ile Val Ala Cys Thr Leu Pro Val Ser Val Val His Phe Pro Gln Trp
    450                 455                 460

Gly Ser Met Phe Leu Pro Pro Ser Lys Asp Val Ser Lys Ser Thr Glu
465                 470                 475                 480

Glu Phe Tyr Tyr Thr Ser Glu Trp Asn Glu Glu Lys Gln Lys Gly
                485                 490                 495

Leu His Gln Gln Ser Leu Lys Phe Ala Glu Asn Ser Arg Ser Glu Arg
                500                 505                 510

Gly Lys Arg Val Ala Ser Ala Pro Thr Pro Asn Ala Thr Pro Thr
            515                 520                 525

His Val
    530

<210> SEQ ID NO 10
<211> LENGTH: 1590
<212> TYPE: DNA
<213> ORGANISM: Glycine max
<220> FEATURE:
<223> OTHER INFORMATION: Soybean nucleic acid sequence - OsNRT2.3b
      related gene

<400> SEQUENCE: 10
atggctgaga ttgagggttc tcctggaagc tccatgcatg gagtaacagg aagagaacaa      60
acattcgtag cctcaattgc ttctccaatt gtccccacag acaccacagc caaatttgct     120
ctcccagtag actcagagca caaggccaag attttcaaac tcttctccat ggccaatccc     180
cacatgagaa cctccacact tcttggatc tccttcttca cctgcttcgt ctcgaccttc      240
gcagcagccc ctcttgtccc catcatccgc gacaacctta acctcaccaa agcgacatt      300 ggaaacgccg gggttgcttc tgtctccgga agcatcttct ctaggcttgc aatgggtgcg     360
gtctgtgacc tattaggtcc acgttatggc tgtgccttcc tcatcatgct ctcggcccca     420
accgtgttct gcatgtcctt tgtgaaagat gctgcggggt acataatggt tcggttcttg     480
atagggttct ccttggcaac gttcgtgtca tgccagtact ggatgagcac gatgttcaac     540
agtaagatta tagggcttgc gaatggaact gctgcggggt ggggaacat gggtggtgga      600 gccactcagc tcataatgcc tttggtgtat gagcttatca gaaagctgg ggctactccc      660 ttcactgctt ggaggatagc cttctttgta ccgggtttca tgcatgtcat catggggatc     720
cttgtcctaa ctctaggcca ggacttgcct gatggaaacc ttgcggcctt gcagaagaag     780
ggtgatgtag caaaagacaa gttttccaag gtgctatggt atgccataac aaattacagg     840
acatggattt tgccctcct ctatgggtac tcaatgggag ttgaattgac aactgacaat     900
gtcattgctg agtatttcta tgacaggttt aatctgaagc tgcacactgc tggaatcatt     960
gctgcttcat ttggaatggc aaacttagtt gctcgaccct tggtggata tgcttctgat    1020 gttgcagcca gattgtttgg catgagggga agactctgga cccttggat cctccaaaca    1080 ttaggagggg ttttctgtat ttggcttggc cgagccaatt ctcttcctat tgctattttg    1140
```

```
gctatgatcc tgttctcttt aggagctcaa gctgcatgtg gtgcaacttt tggcatcatt    1200
cccttcatct caagaaggtc attggggatc atatcaggtc tcactggtgc aggtgggaac    1260
tttgggtctg gcctcaccca attggtcttc ttttcaacat ccaaattctc cactgccaca    1320
ggtctctcct tgatgggtgt gatgatagtg gcttgcactc ttcctgtgag tgttgttcat    1380
tttccacagt ggggtagcat gttcctacca ccatcaaaag atgtcaacaa atccactgaa    1440
gaattctatt acacctctga atggaatgag gaagagaggc agaaaggctt gcatcagcaa    1500
agtctcaagt ttgctgagaa tagccgatcc gagagaggaa agcgagtggc ttcagcacca    1560
acacctccga atgcaactcc cactcatgtc                                     1590
```

<210> SEQ ID NO 11
<211> LENGTH: 530
<212> TYPE: PRT
<213> ORGANISM: Glycine max
<220> FEATURE:
<223> OTHER INFORMATION: Soybean amino acid sequence - OsNRT2.3b related gene

<400> SEQUENCE: 11

```
Met Ala Glu Ile Glu Gly Ser Pro Gly Ser Ser Met His Gly Val Thr
1               5                   10                  15

Gly Arg Glu Gln Thr Phe Val Ala Ser Ile Ala Ser Pro Ile Val Pro
                20                  25                  30

Thr Asp Thr Thr Ala Lys Phe Ala Leu Pro Val Asp Ser Glu His Lys
            35                  40                  45

Ala Lys Ile Phe Lys Leu Phe Ser Met Ala Asn Pro His Met Arg Thr
        50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
                100                 105                 110

Phe Ser Arg Leu Ala Met Gly Ala Val Cys Asp Leu Leu Gly Pro Arg
            115                 120                 125

Tyr Gly Cys Ala Phe Leu Ile Met Leu Ser Ala Pro Thr Val Phe Cys
        130                 135                 140

Met Ser Phe Val Lys Asp Ala Ala Gly Tyr Ile Met Val Arg Phe Leu
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Ala Asn Gly Thr Ala Ala
                180                 185                 190

Gly Trp Gly Asn Met Gly Gly Ala Thr Gln Leu Ile Met Pro Leu
            195                 200                 205

Val Tyr Glu Leu Ile Arg Arg Ala Gly Ala Thr Pro Phe Thr Ala Trp
        210                 215                 220

Arg Ile Ala Phe Phe Val Pro Gly Phe Met His Val Ile Met Gly Ile
225                 230                 235                 240

Leu Val Leu Thr Leu Gly Gln Asp Leu Pro Asp Gly Asn Leu Ala Ala
                245                 250                 255

Leu Gln Lys Lys Gly Asp Val Ala Lys Asp Lys Phe Ser Lys Val Leu
            260                 265                 270

Trp Tyr Ala Ile Thr Asn Tyr Arg Thr Trp Ile Phe Ala Leu Leu Tyr
```

```
                275                 280                 285
Gly Tyr Ser Met Gly Val Glu Leu Thr Thr Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Ser Phe Gly Met Ala Asn Leu Val Ala Arg Pro Phe Gly Gly
                325                 330                 335

Tyr Ala Ser Asp Val Ala Ala Arg Leu Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Ile Leu Ala Met Ile Leu
    370                 375                 380

Phe Ser Leu Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Lys Phe Ser Thr Ala Thr Gly Leu Ser Leu Met Gly Val Met
        435                 440                 445

Ile Val Ala Cys Thr Leu Pro Val Ser Val His Phe Pro Gln Trp
    450                 455                 460

Gly Ser Met Phe Leu Pro Pro Ser Lys Asp Val Asn Lys Ser Thr Glu
465                 470                 475                 480

Glu Phe Tyr Tyr Thr Ser Glu Trp Asn Glu Glu Arg Gln Lys Gly
                485                 490                 495

Leu His Gln Gln Ser Leu Lys Phe Ala Glu Asn Ser Arg Ser Glu Arg
            500                 505                 510

Gly Lys Arg Val Ala Ser Ala Pro Thr Pro Pro Asn Ala Thr Pro Thr
        515                 520                 525

His Val
    530

<210> SEQ ID NO 12
<211> LENGTH: 1875
<212> TYPE: DNA
<213> ORGANISM: Hordeum vulgare
<220> FEATURE:
<223> OTHER INFORMATION: Barley nucleic acid sequence - OsNRT2.3b
      related gene

<400> SEQUENCE: 12
ccacgcgtcc gctcattgca tacgaggttg ccaacactac acaggtgtag cagcagccaa      60
ggcagctggt gagatggagg gggagtccaa gccggcggcg atggggggtgc aggcggcgcc     120 caagggcaag ttcaggatac cggtggactc ggacaacaag gccaccgagt ctggctttt      180 ctcgttcgtg aggccgcaca tgagcgcctt ccacctctcg tggttctcct tcttctgctg     240
cttcgtctcc accttcgccg cgccgcccct cctgccgctc atccgggaca acctcggcct     300
cacgggcaag gacatcggca acgccggcat cgcgtccgtg tccggcgccg tgttcgcgcg     360
tctcgccatg ggcacgggcct gcgacctggt cgggccccgc ctggcgtccg cggccatcat     420
actgctcacc accccgcgg tgtactgctc cgccatcatc gagtccgcct cgtcgttcct     480
gctcgtgcgc ttcttcacgg gcttctcgct cgcctccttc gtgtcgacgc agttctggat     540
```

```
gagctccatg ttctcttcgc ccaaggtggg gctggccaat ggcgtcgccg gcggctgggg      600
caacctgggc gggggcgccg tgcagctcct catgccgctc gtgttcgagg ccgtccgcaa      660
gatcggcagc acggatttca tcgcgtggcg cgtcgccttc ttcatcccgg gcgtcatgca      720
gacgttctcg gccatcgccg tgctggcgtt cgggcaggac atgccggacg caactaccg       780 taagctgcac aagagcgggg agatgcacaa ggacagcttc ggcaacgtgc tgcgccacgc      840
ggtcacgaac taccgcgcct ggatcctggc gctcacctac ggctactcct cggcgtgga      900 gctcgccgtg gacaacatcg tcgcgcagta cttctacgac cgcttcgacg tcaacctcca      960
cacggccggg ctcatcgccg ccagcttcgg gatggccaac atcatctccc gcccgggcgg     1020
cgggctcatg tccgactggc tctccgaccg gttcggcatg cgcggcaggc tgtgggggct     1080
gtgggtcgtg cagaccatcg gcggcatcct ctgcatcgtg ctcggcatcg tcgactactc     1140
gttcggcgcg tcggtggccg tcatgatcct cttctccttc ttcgtgcagg cggcgtgcgg     1200
gctcacgttc ggcatcgtgc cgttcgtgtc gcggaggtcg ctggggctca tctccggaat     1260
gaccggcggc ggcggcaacg tgggggccgt gctgacgcag gtcatcttct ccgcggcac      1320 caagtacaag acggagacgg ggatcatgta catgggctg atgatcctgg catgcacgct      1380
gcccatcacg ctcatctact cccgcagtg gggcggcatg ttcgtcgggc gcggaaagg      1440 ggcgacggcg gaggagtact acagcaagga gtggaccgag gaggagcgtg ccaaggggta     1500
cagcgccgcg accgagcgtt cgcggagaa cagcgtgcgc gagggcgggc ggagggcggc     1560
gtcgggcagc cagtcaaggc acaccgtccc cgtcgacggc tcgccggccg acgtgtgagg     1620
tccgaagagc tccccgtact acgtggtcca cgggtgcaat gggggaatac gatcgcgtcg     1680
cacggccgcc cgggtttggg ccgtcttccg tgcacatacg tagtactacg aacgcacgca     1740
cgcacgccgc ctttgtgctg cttctagtac tgtacgtacg tttgggtttg gtgtgctcgc     1800
ttaccttaat actgctccgc atgttgatgt ttatatgctc ccttgtgaaa tacagtttta     1860
aaaaaaaaaa aaaaa                                                      1875
```

<210> SEQ ID NO 13
<211> LENGTH: 514
<212> TYPE: PRT
<213> ORGANISM: Hordeum vulgare
<220> FEATURE:
<223> OTHER INFORMATION: Barley amino acid sequence - OsNRT2.3b related
      gene

<400> SEQUENCE: 13

Met Glu Gly Glu Ser Lys Pro Ala Ala Met Gly Val Gln Ala Ala Pro
1               5                   10                  15

Lys Gly Lys Phe Arg Ile Pro Val Asp Ser Asp Asn Lys Ala Thr Glu
            20                  25                  30

Phe Trp Leu Phe Ser Phe Val Arg Pro His Met Ser Ala Phe His Leu
        35                  40                  45

Ser Trp Phe Ser Phe Phe Cys Cys Phe Val Ser Thr Phe Ala Ala Pro
    50                  55                  60

Pro Leu Leu Pro Leu Ile Arg Asp Asn Leu Gly Leu Thr Gly Lys Asp
65                  70                  75                  80

Ile Gly Asn Ala Gly Ile Ala Ser Val Ser Gly Ala Val Phe Ala Arg
                85                  90                  95

Leu Ala Met Gly Thr Ala Cys Asp Leu Val Gly Pro Arg Leu Ala Ser
            100                 105                 110

Ala Ala Ile Ile Leu Leu Thr Thr Pro Ala Val Tyr Cys Ser Ala Ile

-continued

```
            115                 120                 125
Ile Glu Ser Ala Ser Ser Phe Leu Leu Val Arg Phe Phe Thr Gly Phe
130                 135                 140
Ser Leu Ala Ser Phe Val Ser Thr Gln Phe Trp Met Ser Ser Met Phe
145                 150                 155                 160
Ser Ser Pro Lys Val Gly Leu Ala Asn Gly Val Ala Gly Gly Trp Gly
            165                 170                 175
Asn Leu Gly Gly Gly Ala Val Gln Leu Leu Met Pro Leu Val Phe Glu
        180                 185                 190
Ala Val Arg Lys Ile Gly Ser Thr Asp Phe Ile Ala Trp Arg Val Ala
    195                 200                 205
Phe Phe Ile Pro Gly Val Met Gln Thr Phe Ser Ala Ile Ala Val Leu
210                 215                 220
Ala Phe Gly Gln Asp Met Pro Asp Gly Asn Tyr Arg Lys Leu His Lys
225                 230                 235                 240
Ser Gly Glu Met His Lys Asp Ser Phe Gly Asn Val Leu Arg His Ala
            245                 250                 255
Val Thr Asn Tyr Arg Ala Trp Ile Leu Ala Leu Thr Tyr Gly Tyr Ser
            260                 265                 270
Phe Gly Val Glu Leu Ala Val Asp Asn Ile Val Ala Gln Tyr Phe Tyr
        275                 280                 285
Asp Arg Phe Asp Val Asn Leu His Thr Ala Gly Leu Ile Ala Ala Ser
    290                 295                 300
Phe Gly Met Ala Asn Ile Ile Ser Arg Pro Gly Gly Gly Leu Met Ser
305                 310                 315                 320
Asp Trp Leu Ser Asp Arg Phe Gly Met Arg Gly Arg Leu Trp Gly Leu
            325                 330                 335
Trp Val Val Gln Thr Ile Gly Gly Ile Leu Cys Ile Val Leu Gly Ile
            340                 345                 350
Val Asp Tyr Ser Phe Gly Ala Ser Val Ala Val Met Ile Leu Phe Ser
        355                 360                 365
Phe Phe Val Gln Ala Ala Cys Gly Leu Thr Phe Gly Ile Val Pro Phe
    370                 375                 380
Val Ser Arg Arg Ser Leu Gly Leu Ile Ser Gly Met Thr Gly Gly Gly
385                 390                 395                 400
Gly Asn Val Gly Ala Val Leu Thr Gln Val Ile Phe Phe Arg Gly Thr
            405                 410                 415
Lys Tyr Lys Thr Glu Thr Gly Ile Met Tyr Met Gly Leu Met Ile Leu
            420                 425                 430
Ala Cys Thr Leu Pro Ile Thr Leu Ile Tyr Phe Pro Gln Trp Gly Gly
        435                 440                 445
Met Phe Val Gly Pro Arg Lys Gly Ala Thr Ala Glu Glu Tyr Tyr Ser
    450                 455                 460
Lys Glu Trp Thr Glu Glu Glu Arg Ala Lys Gly Tyr Ser Ala Ala Thr
465                 470                 475                 480
Glu Arg Phe Ala Glu Asn Ser Val Arg Glu Gly Gly Arg Arg Ala Ala
            485                 490                 495
Ser Gly Ser Gln Ser Arg His Thr Val Pro Val Asp Gly Ser Pro Ala
            500                 505                 510
Asp Val

<210> SEQ ID NO 14
<211> LENGTH: 1900
```

<212> TYPE: DNA
<213> ORGANISM: Brachypodium distachyon
<220> FEATURE:
<223> OTHER INFORMATION: Purple false brome nucleic acid sequence - OsNRT2.3b related gene

<400> SEQUENCE: 14

| | | | | | |
|---|---|---|---|---|---|
| atgggggggg | agtcgaagcc | ggcggcgatg | gatgtggagg | cgccgtccaa | ggccaagttc | 60 |
| aggatccccg | tggactccga | caacaaggcg | acggagttct | ggctcttctc | cttcgcgcgg | 120 |
| ccgcacatga | gcgcgttcca | cctgtcgtgg | ttctccttct | tctgctgctt | cgtgtccacc | 180 |
| ttcgcggcgc | cgccgctgct | gccgctcatc | cgggacaatc | tggggctcac | ggccaaggac | 240 |
| atcggcaacg | ccgggatcgc | gtcggtgtcg | ggcgccgtgt | tcgcgcgtct | cgccatgggc | 300 |
| acggcctgcg | acctggtcgg | ccccgcctg | gcgtccgcgg | ccatcatact | gctcaccacc | 360 |
| ccggcggtgt | actgctcggc | catcatcgac | tcggcgtcgt | cgttcctgct | cgtgcgcttc | 420 |
| ttcacgggct | tctccctggc | ctccttcgtg | tccacgcagt | tctggatgag | ctccatgttc | 480 |
| tcctcgccca | aggtgggtct | ggccaacggc | gtggccgggg | gctggggcaa | cctcggcggc | 540 |
| ggcgccgtgc | agctgatcat | gccgctggtg | ttcgaggtcg | tgcgcaagat | cgggagcacg | 600 |
| cggttcacgg | cgtggcgcgt | ggccttcttc | atcccgggcg | tcatgcagac | gttctcggcc | 660 |
| atcgccgtgc | tggcgttcgg | gcaggacatg | ccggacggca | actaccacaa | gctgcacaag | 720 |
| accggggaga | tgcacaggga | cagcttccgc | aacgtgctgc | ccacgcggt | caccaactac | 780 |
| cgcgcctgga | tcctggcgct | cacctacggc | tactgcttcg | gcgtggagct | cgccgtggac | 840 |
| aacatcgtgg | cgcagtactt | ctacgaccgc | ttcggcgtca | acctccacac | ggcggggctc | 900 |
| atcgccgcca | gcttcgggat | ggccaacatc | gtctcgcgcc | cgggcggcgg | gctcatgtcc | 960 |
| gactggctct | cggcccggtt | cggcatgcgc | ggcaggctgt | ggggcctgtg | ggtcgtgcag | 1020 |
| accatcggcg | gcgtcctctg | cgtggtgctc | ggcgtggtgg | actactcctt | cggcgcgtcc | 1080 |
| gtggcagtca | tgatactctt | ctccctgttc | gtgcaggccg | cgtgcgggct | caccttcggc | 1140 |
| atcgtgccgt | tcgtgtcgcg | gaggtcgctg | gggctcatct | ctggcatgac | cggcggcggg | 1200 |
| ggaaatgtgg | cgccgtgct | gacgcaggtc | atcttcttcc | acgggtccag | gtacaagacg | 1260 |
| gagacgggga | tcatgtacat | gggggtcatg | atcatcgcgt | gcacgctgcc | catcacgctc | 1320 |
| atctacttcc | gcagtgggg | cggcatgttc | accgggccgc | ggccggggc | cacggcggag | 1380 |
| gagtattaca | gctcggagtg | gaccgaggag | gagcggaaga | agggtacaa | cgccgcgaca | 1440 |
| gagcgtttcg | cggagaacag | cctgcgcgag | ggagggcgga | gggccgcgtc | gggcagccag | 1500 |
| tccaagcata | ccgtccccgt | ggacggatca | ccgccggccg | acgtgtgaag | aaaatcccat | 1560 |
| agaccatagt | gtacgtttcg | tatgtctcgc | gtctataacg | agtcatacgg | tcgccacggt | 1620 |
| cgccggtctg | gttacgtgcg | ttggctttt | tatgtgttgt | accttttggc | ttttggtgct | 1680 |
| cctttgtctt | gttgctgtaa | aaggttgtca | aatactccac | ttttctttc | cgcagacgtg | 1740 |
| aaatacttct | gtaggtgtac | gtcactgaaa | ggaaactgtt | catatggcat | ccacatacaa | 1800 |
| aaccatgttt | tcttatattg | ctagtatatt | cgttttttctt | atttcgacga | aactagcatt | 1860 |
| ccgcgtctat | tattattcgt | aagatacttc | cgatcgaaaa | | | 1900 |

<210> SEQ ID NO 15
<211> LENGTH: 515
<212> TYPE: PRT
<213> ORGANISM: Brachypodium distachyon
<220> FEATURE:
<223> OTHER INFORMATION: Purple false brome amino acid sequence -

OsNRT2.3b related gene

<400> SEQUENCE: 15

```
Met Gly Gly Glu Ser Lys Pro Ala Ala Met Asp Val Glu Ala Pro Ser
1               5                   10                  15

Lys Ala Lys Phe Arg Ile Pro Val Asp Ser Asp Asn Lys Ala Thr Glu
            20                  25                  30

Phe Trp Leu Phe Ser Phe Ala Arg Pro His Met Ser Ala Phe His Leu
            35                  40                  45

Ser Trp Phe Ser Phe Phe Cys Cys Phe Val Ser Thr Phe Ala Ala Pro
        50                  55                  60

Pro Leu Leu Pro Leu Ile Arg Asp Asn Leu Gly Leu Thr Ala Lys Asp
65                  70                  75                  80

Ile Gly Asn Ala Gly Ile Ala Ser Val Ser Gly Ala Val Phe Ala Arg
                85                  90                  95

Leu Ala Met Gly Thr Ala Cys Asp Leu Val Gly Pro Arg Leu Ala Ser
            100                 105                 110

Ala Ala Ile Ile Leu Leu Thr Thr Pro Ala Val Tyr Cys Ser Ala Ile
            115                 120                 125

Ile Asp Ser Ala Ser Ser Phe Leu Leu Val Arg Phe Phe Thr Gly Phe
130                 135                 140

Ser Leu Ala Ser Phe Val Ser Thr Gln Phe Trp Met Ser Ser Met Phe
145                 150                 155                 160

Ser Ser Pro Lys Val Gly Leu Ala Asn Gly Val Ala Gly Gly Trp Gly
                165                 170                 175

Asn Leu Gly Gly Gly Ala Val Gln Leu Ile Met Pro Leu Val Phe Glu
            180                 185                 190

Val Val Arg Lys Ile Gly Ser Thr Arg Phe Thr Ala Trp Arg Val Ala
            195                 200                 205

Phe Phe Ile Pro Gly Val Met Gln Thr Phe Ser Ala Ile Ala Val Leu
        210                 215                 220

Ala Phe Gly Gln Asp Met Pro Asp Gly Asn Tyr His Lys Leu His Lys
225                 230                 235                 240

Thr Gly Glu Met His Arg Asp Ser Phe Arg Asn Val Leu Arg His Ala
                245                 250                 255

Val Thr Asn Tyr Arg Ala Trp Ile Leu Ala Leu Thr Tyr Gly Tyr Cys
            260                 265                 270

Phe Gly Val Glu Leu Ala Val Asp Asn Ile Val Ala Gln Tyr Phe Tyr
            275                 280                 285

Asp Arg Phe Gly Val Asn Leu His Thr Ala Gly Leu Ile Ala Ala Ser
        290                 295                 300

Phe Gly Met Ala Asn Ile Val Ser Arg Pro Gly Gly Gly Leu Met Ser
305                 310                 315                 320

Asp Trp Leu Ser Ala Arg Phe Gly Met Arg Gly Arg Leu Trp Gly Leu
                325                 330                 335

Trp Val Val Gln Thr Ile Gly Gly Val Leu Cys Val Val Leu Gly Val
            340                 345                 350

Val Asp Tyr Ser Phe Gly Ala Ser Val Ala Val Met Ile Leu Phe Ser
            355                 360                 365

Leu Phe Val Gln Ala Ala Cys Gly Leu Thr Phe Gly Ile Val Pro Phe
        370                 375                 380

Val Ser Arg Arg Ser Leu Gly Leu Ile Ser Gly Met Thr Gly Gly Gly
385                 390                 395                 400
```

Gly Asn Val Gly Ala Val Leu Thr Gln Val Ile Phe Phe His Gly Ser
            405                 410                 415

Arg Tyr Lys Thr Glu Thr Gly Ile Met Tyr Met Gly Val Met Ile Ile
        420                 425                 430

Ala Cys Thr Leu Pro Ile Thr Leu Ile Tyr Phe Pro Gln Trp Gly Gly
            435                 440                 445

Met Phe Thr Gly Pro Arg Pro Gly Ala Thr Ala Glu Glu Tyr Tyr Ser
450                 455                 460

Ser Glu Trp Thr Glu Glu Arg Lys Lys Gly Tyr Asn Ala Ala Thr
465                 470                 475                 480

Glu Arg Phe Ala Glu Asn Ser Leu Arg Glu Gly Gly Arg Arg Ala Ala
            485                 490                 495

Ser Gly Ser Gln Ser Lys His Thr Val Pro Val Asp Gly Ser Pro Pro
        500                 505                 510

Ala Asp Val
        515

<210> SEQ ID NO 16
<211> LENGTH: 8
<212> TYPE: PRT
<213> ORGANISM: Oryza sativa
<220> FEATURE:
<223> OTHER INFORMATION: pH Sensing Motif

<400> SEQUENCE: 16

Val Tyr Glu Ala Ile His Lys Ile
1               5

<210> SEQ ID NO 17
<211> LENGTH: 22
<212> TYPE: DNA
<213> ORGANISM: Artificial
<220> FEATURE:
<223> OTHER INFORMATION: Forward Primer

<400> SEQUENCE: 17
ggaattctca cacccgggcc gg                                              22

<210> SEQ ID NO 18
<211> LENGTH: 26
<212> TYPE: DNA
<213> ORGANISM: Artificial
<220> FEATURE:
<223> OTHER INFORMATION: Reverse Primer

<400> SEQUENCE: 18
cgggatccat gtgggcggc atgctc                                           26

<210> SEQ ID NO 19
<211> LENGTH: 21
<212> TYPE: DNA
<213> ORGANISM: Artificial
<220> FEATURE:
<223> OTHER INFORMATION: RNA in situ hybridization probe - sense
      sequence

<400> SEQUENCE: 19
cgatggttgg gtgcggcgag a                                               21

<210> SEQ ID NO 20
<211> LENGTH: 21
<212> TYPE: DNA
<213> ORGANISM: Artificial

```
<220> FEATURE:
<223> OTHER INFORMATION: RNA in situ hybridization probe - nonsense
      sequence

<400> SEQUENCE: 20
gctaccaacc cacgccgctc t                                          21

<210> SEQ ID NO 21
<211> LENGTH: 13
<212> TYPE: DNA
<213> ORGANISM: Artificial
<220> FEATURE:
<223> OTHER INFORMATION: RT-PCR Forward primer - OsNRT2.3b (AK072215)

<400> SEQUENCE: 21
cgttcgccgt gtt                                                   13

<210> SEQ ID NO 22
<211> LENGTH: 18
<212> TYPE: DNA
<213> ORGANISM: Artificial
<220> FEATURE:
<223> OTHER INFORMATION: RT-PCR Reverse primer - OsNRT2.3b (AK072215)

<400> SEQUENCE: 22
tcgaagcggt cgtagaag                                              18

<210> SEQ ID NO 23
<211> LENGTH: 19
<212> TYPE: DNA
<213> ORGANISM: Artificial
<220> FEATURE:
<223> OTHER INFORMATION: RT-PCR Forward primer - Actin

<400> SEQUENCE: 23
ttatggttgg gatgggaca                                             19

<210> SEQ ID NO 24
<211> LENGTH: 18
<212> TYPE: DNA
<213> ORGANISM: Artificial
<220> FEATURE:
<223> OTHER INFORMATION: RT-PCR Reverse primer - Actin

<400> SEQUENCE: 24
agcacggctt gaatagcg                                              18

<210> SEQ ID NO 25
<211> LENGTH: 30
<212> TYPE: DNA
<213> ORGANISM: Artificial
<220> FEATURE:
<223> OTHER INFORMATION: Forward primer used for over-expression
      constructs (Vector: pCAMBIA1302)

<400> SEQUENCE: 25
atccatggag atctcagggc acagcggatg                                 30

<210> SEQ ID NO 26
<211> LENGTH: 27
<212> TYPE: DNA
<213> ORGANISM: Artificial
<220> FEATURE:
<223> OTHER INFORMATION: Reverse primer used for over-expression
      constructs (Vector: pCAMBIA1302)

<400> SEQUENCE: 26
```

```
atccatggag atctacaccc cggccgg                                          27
```

<210> SEQ ID NO 27
<211> LENGTH: 28
<212> TYPE: DNA
<213> ORGANISM: Artificial
<220> FEATURE:
<223> OTHER INFORMATION: Forward primer for over-expression construct
      (Vector: pTCK303)

<400> SEQUENCE: 27

```
caactagtgc taccacgtgt tggagatg                                         28
```

<210> SEQ ID NO 28
<211> LENGTH: 27
<212> TYPE: DNA
<213> ORGANISM: Artificial
<220> FEATURE:
<223> OTHER INFORMATION: Reverse primer for over-expression construct
      (Vector: pTCK303)

<400> SEQUENCE: 28

```
gaactagtga gcaaaccacc aacaagc                                          27
```

<210> SEQ ID NO 29
<211> LENGTH: 25
<212> TYPE: DNA
<213> ORGANISM: Artificial
<220> FEATURE:
<223> OTHER INFORMATION: Forward subcloning primer

<400> SEQUENCE: 29

```
aatcagatct ttggagctcc accgc                                            25
```

<210> SEQ ID NO 30
<211> LENGTH: 24
<212> TYPE: DNA
<213> ORGANISM: Artificial
<220> FEATURE:
<223> OTHER INFORMATION: Reverse subcloning primer

<400> SEQUENCE: 30

```
cagaactagt cccccctcg aagg                                              24
```

<210> SEQ ID NO 31
<211> LENGTH: 25
<212> TYPE: DNA
<213> ORGANISM: Artificial
<220> FEATURE:
<223> OTHER INFORMATION: Mutagenic primer for mutation H167R-F

<400> SEQUENCE: 31

```
gccattcgaa agatcggtag cacgc                                            25
```

<210> SEQ ID NO 32
<211> LENGTH: 25
<212> TYPE: DNA
<213> ORGANISM: Artificial
<220> FEATURE:
<223> OTHER INFORMATION: Original sequence

<400> SEQUENCE: 32

```
gccatccaca agatcggtag cacgc                                            25
```

<210> SEQ ID NO 33

```
<211> LENGTH: 30
<212> TYPE: DNA
<213> ORGANISM: Artificial
<220> FEATURE:
<223> OTHER INFORMATION: Mutagenic primer for mutation H167R-R

<400> SEQUENCE: 33
gcattctaga ttcgaatggc ctcgtacacg                                          30

<210> SEQ ID NO 34
<211> LENGTH: 30
<212> TYPE: DNA
<213> ORGANISM: Artificial
<220> FEATURE:
<223> OTHER INFORMATION: Mutagenic primer for mutation 67RB-R

<400> SEQUENCE: 34
gcattctaga ttcgaatggc ctcgtacacg                                          30

<210> SEQ ID NO 35
<211> LENGTH: 18
<212> TYPE: DNA
<213> ORGANISM: Artificial
<220> FEATURE:
<223> OTHER INFORMATION: Forward RT-PCR Primer for OsNRT2.3a (AK072215)

<400> SEQUENCE: 35
gctcatccgc gacaccct                                                       18

<210> SEQ ID NO 36
<211> LENGTH: 18
<212> TYPE: DNA
<213> ORGANISM: Artificial
<220> FEATURE:
<223> OTHER INFORMATION: Reverse RT-PCR Primer for OsNRT2.3a (AK072215)

<400> SEQUENCE: 36
gtcgaagcgg tcgtagaa                                                       18

<210> SEQ ID NO 37
<211> LENGTH: 13
<212> TYPE: DNA
<213> ORGANISM: Artificial
<220> FEATURE:
<223> OTHER INFORMATION: Forward RT-PCR primer for OsNRT2.3b (AK072215)

<400> SEQUENCE: 37
cgttcgccgt gtt                                                            13

<210> SEQ ID NO 38
<211> LENGTH: 18
<212> TYPE: DNA
<213> ORGANISM: Artificial
<220> FEATURE:
<223> OTHER INFORMATION: Forward RT-PCR Primer for OsNRT2.3b (AK072215)

<400> SEQUENCE: 38
tcgaagcggt cgtagaag                                                       18

<210> SEQ ID NO 39
<211> LENGTH: 19
<212> TYPE: DNA
<213> ORGANISM: Artificial
<220> FEATURE:
<223> OTHER INFORMATION: Forward RT-PCR primer for OsActin (NM_197297)

<400> SEQUENCE: 39
```

```
ttatggttgg gatgggaca                                              19

<210> SEQ ID NO 40
<211> LENGTH: 18
<212> TYPE: DNA
<213> ORGANISM: Artificial
<220> FEATURE:
<223> OTHER INFORMATION: Reverse RT-PCR primer for OsActin (NM_197297)

<400> SEQUENCE: 40
agcacggctt gaatagcg                                               18

<210> SEQ ID NO 41
<211> LENGTH: 10
<212> TYPE: PRT
<213> ORGANISM: Arabidopsis thaliana

<400> SEQUENCE: 41

Phe Phe Val Gly Phe Ser Leu Ala Asn Phe
1               5                   10

<210> SEQ ID NO 42
<211> LENGTH: 9
<212> TYPE: PRT
<213> ORGANISM: Arabidopsis thaliana

<400> SEQUENCE: 42

Glu Ile Leu Ile Gly Gly Leu Gly Asn
1               5

<210> SEQ ID NO 43
<211> LENGTH: 10
<212> TYPE: PRT
<213> ORGANISM: Arabidopsis lyrata

<400> SEQUENCE: 43

Phe Phe Val Gly Phe Ser Leu Ala Asn Phe
1               5                   10

<210> SEQ ID NO 44
<211> LENGTH: 9
<212> TYPE: PRT
<213> ORGANISM: Arabidopsis lyrata

<400> SEQUENCE: 44

Glu Ile Leu Ile Gly Gly Leu Gly Asn
1               5

<210> SEQ ID NO 45
<211> LENGTH: 10
<212> TYPE: PRT
<213> ORGANISM: Capsella rubella

<400> SEQUENCE: 45

Phe Phe Val Gly Phe Ser Leu Ala Asn Phe
1               5                   10

<210> SEQ ID NO 46
<211> LENGTH: 9
<212> TYPE: PRT
<213> ORGANISM: Capsella rubella

<400> SEQUENCE: 46

Glu Ile Leu Ile Gly Gly Leu Gly Asn
```

```
<210> SEQ ID NO 47
<211> LENGTH: 7
<212> TYPE: PRT
<213> ORGANISM: Capsella rubella

<400> SEQUENCE: 47

Phe Ser Val Ala Ser Pro Ile
1               5

<210> SEQ ID NO 48
<211> LENGTH: 9
<212> TYPE: PRT
<213> ORGANISM: Capsella rubella

<400> SEQUENCE: 48

Leu Trp Ile Ile Gln Thr Ala Gly Gly
1               5

<210> SEQ ID NO 49
<211> LENGTH: 7
<212> TYPE: PRT
<213> ORGANISM: Populus trichocarpa
<220> FEATURE:
<221> NAME/KEY: MiscFeature
<222> LOCATION: (1)..(7)
<223> OTHER INFORMATION: Potri.009G008500

<400> SEQUENCE: 49

Phe Ser Val Ala Ser Pro Ile
1               5

<210> SEQ ID NO 50
<211> LENGTH: 9
<212> TYPE: PRT
<213> ORGANISM: Populus trichocarpa
<220> FEATURE:
<221> NAME/KEY: MiscFeature
<222> LOCATION: (1)..(9)
<223> OTHER INFORMATION: Potri.009G008500

<400> SEQUENCE: 50

Leu Trp Ile Ile Gln Thr Ala Gly Gly
1               5

<210> SEQ ID NO 51
<211> LENGTH: 7
<212> TYPE: PRT
<213> ORGANISM: Populus trichocarpa
<220> FEATURE:
<221> NAME/KEY: MiscFeature
<222> LOCATION: (1)..(7)
<223> OTHER INFORMATION: Potri.009G008600

<400> SEQUENCE: 51

Phe Ser Val Ala Ser Pro Ile
1               5

<210> SEQ ID NO 52
<211> LENGTH: 9
<212> TYPE: PRT
<213> ORGANISM: Populus trichocarpa
<220> FEATURE:
<221> NAME/KEY: MiscFeature
<222> LOCATION: (1)..(9)
<223> OTHER INFORMATION: Potri.009G008600
```

```
<400> SEQUENCE: 52

Leu Trp Ile Ile Gln Thr Ala Gly Gly
1               5

<210> SEQ ID NO 53
<211> LENGTH: 10
<212> TYPE: PRT
<213> ORGANISM: Cucumis sativus

<400> SEQUENCE: 53

Trp Arg Ile Ala Phe Phe Val Pro Gly Phe
1               5                   10

<210> SEQ ID NO 54
<211> LENGTH: 11
<212> TYPE: PRT
<213> ORGANISM: Cucumis sativus

<400> SEQUENCE: 54

Leu Trp Ile Leu Gln Thr Leu Gly Gly Val Phe
1               5                   10

<210> SEQ ID NO 55
<211> LENGTH: 7
<212> TYPE: PRT
<213> ORGANISM: Malus domestica

<400> SEQUENCE: 55

Phe Ser Val Ala Ser Pro Ile
1               5

<210> SEQ ID NO 56
<211> LENGTH: 9
<212> TYPE: PRT
<213> ORGANISM: Malus domestica

<400> SEQUENCE: 56

Leu Trp Ile Ile Gln Thr Ala Gly Gly
1               5

<210> SEQ ID NO 57
<211> LENGTH: 7
<212> TYPE: PRT
<213> ORGANISM: Prunus persica

<400> SEQUENCE: 57

Phe Ser Val Ala Ser Pro Ile
1               5

<210> SEQ ID NO 58
<211> LENGTH: 9
<212> TYPE: PRT
<213> ORGANISM: Prunus persica

<400> SEQUENCE: 58

Leu Trp Ile Ile Gln Thr Ala Gly Gly
1               5

<210> SEQ ID NO 59
<211> LENGTH: 10
<212> TYPE: PRT
<213> ORGANISM: Glycine max
<220> FEATURE:
<221> NAME/KEY: MiscFeature
<222> LOCATION: (1)..(10)
```

```
<223> OTHER INFORMATION: Glyma13g39850

<400> SEQUENCE: 59

Trp Arg Ile Ala Phe Phe Val Pro Gly Phe
1               5                   10

<210> SEQ ID NO 60
<211> LENGTH: 11
<212> TYPE: PRT
<213> ORGANISM: Glycine max
<220> FEATURE:
<221> NAME/KEY: MiscFeature
<222> LOCATION: (1)..(11)
<223> OTHER INFORMATION: Glyma13g39850

<400> SEQUENCE: 60

Leu Trp Ile Leu Gln Thr Leu Gly Gly Val Phe
1               5                   10

<210> SEQ ID NO 61
<211> LENGTH: 10
<212> TYPE: PRT
<213> ORGANISM: Glycine max
<220> FEATURE:
<221> NAME/KEY: MiscFeature
<222> LOCATION: (1)..(10)
<223> OTHER INFORMATION: Glyma12g30050

<400> SEQUENCE: 61

Trp Arg Ile Ala Phe Phe Val Pro Gly Phe
1               5                   10

<210> SEQ ID NO 62
<211> LENGTH: 11
<212> TYPE: PRT
<213> ORGANISM: Glycine max
<220> FEATURE:
<221> NAME/KEY: MiscFeature
<222> LOCATION: (1)..(11)
<223> OTHER INFORMATION: Glyma12g30050

<400> SEQUENCE: 62

Leu Trp Ile Leu Gln Thr Leu Gly Gly Val Phe
1               5                   10

<210> SEQ ID NO 63
<211> LENGTH: 10
<212> TYPE: PRT
<213> ORGANISM: Brachypodium distachyon

<400> SEQUENCE: 63

Phe Phe Ile Pro Gly Val Met Gln Thr Phe
1               5                   10

<210> SEQ ID NO 64
<211> LENGTH: 9
<212> TYPE: PRT
<213> ORGANISM: Brachypodium distachyon

<400> SEQUENCE: 64

Leu Trp Val Val Gln Thr Ile Gly Gly
1               5

<210> SEQ ID NO 65
<211> LENGTH: 10
<212> TYPE: PRT
<213> ORGANISM: Hordeum vulgare
```

<400> SEQUENCE: 65

Phe Phe Ile Pro Gly Val Met Gln Thr Phe
1               5                   10

<210> SEQ ID NO 66
<211> LENGTH: 9
<212> TYPE: PRT
<213> ORGANISM: Hordeum vulgare

<400> SEQUENCE: 66

Leu Trp Val Val Gln Thr Ile Gly Gly
1               5

<210> SEQ ID NO 67
<211> LENGTH: 2000
<212> TYPE: DNA
<213> ORGANISM: Oryza sativa

<400> SEQUENCE: 67

| | | | | | |
|---|---|---|---|---|---|
| gagcgccggc | ctcccaccgg | tcgcgtaaga | tcacgcccga | aatctttatt | cattttctct | 60 |
| ccaccggttg | ccctctcgcc | gcacccaacc | atcgcgccac | gccgcgccgc | gctgccggag | 120 |
| ccgcgctttc | cgctatgcta | aagagctga | cgcgcagggc | acagcggatg | tacgtacaca | 180 |
| cagtcactag | ctaagctgct | agccttgcta | ccacgtgttg | gagatggagg | ctaagccggt | 240 |
| ggcgatggag | gtggagggg | tcgaggcggc | gggggcaag | ccgcggttca | ggatgccggt | 300 |
| ggactccgac | ctcaaggcga | cggagttctg | gctcttctcc | ttcgcgaggc | cacacatggc | 360 |
| ctccttccac | atggcgtggt | tctccttctt | ctgctgcttc | gtgtccacgt | tcgccgtgtt | 420 |
| cgcgcgtctg | gccatgggca | cggcgtgcga | cctggtcggg | cccaggctgg | cctccgcgtc | 480 |
| tctgatcctc | ctcaccacac | cggcggtgta | ctgctcctcc | atcatccagt | ccccgtcggg | 540 |
| gtacctcctc | gtgcgcttct | tcacgggcat | ctcgctggcg | tcgttcgtgt | cggcgcagtt | 600 |
| ctggatgagc | tccatgttct | cggcccccaa | agtggggctg | ccaacggcg | tggccggcgg | 660 |
| ctggggcaac | ctcggcggcg | cgccgtcca | gctgctcatg | ccgctcgtgt | acgaggccat | 720 |
| ccacaagatc | ggtagcacgc | cgttcacggc | gtggcgcatc | gccttcttca | tcccgggcct | 780 |
| gatgcagacg | ttctcggcca | tcgccgtgct | ggcgttcggg | caggacatgc | ccggcggcaa | 840 |
| ctacgggaag | ctccacaaga | ctggcgacat | gcacaaggac | agcttcggca | acgtgctgcg | 900 |
| ccacgccctc | accaactacc | gcggctggat | cctggcgctc | acctacggct | acagcttcgg | 960 |
| cgtcgagctc | accatcgaca | acgtcgtgca | ccagtacttc | tacgaccgct | cgacgtcaa | 1020 |
| cctccagacc | gccgggctca | tcgccgccag | cttcgggatg | ccaacatca | tctcccgccc | 1080 |
| cggcggcggg | ctactctccg | actggctctc | cagccggtac | ggcatgcgcg | caggctgtg | 1140 |
| ggggctgtgg | actgtgcaga | ccatcggcgg | cgtcctctgc | gtggtgctcg | gaatcgtcga | 1200 |
| cttctccttc | gccgcgtccg | tcgccgtgat | ggtgctcttc | tccttcttcg | tccaggccgc | 1260 |
| gtgcgggctc | accttcggca | tcgtgccgtt | cgtgtcgcgg | aggtcgctgg | ggctcatctc | 1320 |
| cgggatgacc | ggcggcgggg | gcaacgtggg | cgccgtgctg | acgcagtaca | tcttcttcca | 1380 |
| cggcacaaag | tacaagacgg | agaccgggat | caagtacatg | gggctcatga | tcatcgcgtg | 1440 |
| cacgctgccc | gtcatgctca | tctacttccc | gcagtggggc | ggcatgctcg | taggcccgag | 1500 |
| gaaggggcc | acggcggagg | agtactacag | ccgggagtgg | tcggatcacg | agcgcgagaa | 1560 |
| gggtttcaac | gcggccagcg | tgcggttcgc | ggagaacagc | gtgcgcgagg | gcgggaggtc | 1620 |

| | |
|---|---:|
| gtcggcgaat ggcggacagc ccaggcacac cgtccccgtc gacgcgtcgc cggccggggt | 1680 |
| gtgaagaatg ccacggacaa taaggtcgcg gttgtagtac aactgtacaa attgatggta | 1740 |
| cgtgtcgttt gaccgcgcgc gcgcacagtg tgggtcgtgg cctcgtgggc ttagtggagt | 1800 |
| acagtgaggg gtgtacgtgt gtcgtggcgc gcgcggtcac ctcggtggcc ttgggattgg | 1860 |
| gggggcacta tacgctagta ctccagatat atacgggttt gatttacttc tgtggatcgg | 1920 |
| cgcttgttgg tggtttgctc cctgtggttt ttgtgatggt aatcatactc atactcaaac | 1980 |
| agtcaaaact ttttgatgcg | 2000 |

<210> SEQ ID NO 68
<211> LENGTH: 1893
<212> TYPE: DNA
<213> ORGANISM: Oryza sativa

<400> SEQUENCE: 68

| | |
|---|---:|
| agtcactagc taagctgcta gccttgctac cacgtgttgg agatggaggc taagccggtg | 60 |
| gcgatggagg tggagggggt cgaggcggcg gggggcaagc cgcggttcag gatgccggtg | 120 |
| gactccgacc tcaaggcgac ggagttctgg ctcttctcct tcgcgaggcc acacatggcc | 180 |
| tccttccaca tggcgtggtt ctccttcttc tgctgcttcg tgtccacgtt cgccgcgccg | 240 |
| ccgctgctgc cgctcatccg cgacaccctc gggctcacgg ccacggacat cggcaacgcc | 300 |
| gggatcgcgt ccgtgtcggg cgccgtgttc gcgcgtctgg ccatgggcac ggcgtgcgac | 360 |
| ctggtcgggc ccaggctggc ctccgcgtct ctgatcctcc tcaccacacc ggcggtgtac | 420 |
| tgctcctcca tcatccagtc cccgtcgggg tacctcctcg tgcgcttctt cacgggcatc | 480 |
| tcgctggcgt cgttcgtgtc ggcgcagttc tggatgagct ccatgttctc ggcccccaaa | 540 |
| gtggggctgg ccaacggcgt ggccggcggc tggggcaacc tcggcggcgg cgccgtccag | 600 |
| ctgctcatgc cgctcgtgta cgaggccatc cacaagatcg gtagcacgcc gttcacggcg | 660 |
| tggcgcatcg ccttcttcat cccggggctg atgcagacgt tctcggccat cgccgtgctg | 720 |
| gcgttcgggc aggacatgcc cggcggcaac tacgggaagc tccacaagac tggcgacatg | 780 |
| cacaaggaca gcttcggcaa cgtgctgcgc acgccctca ccaactaccg cggctggatc | 840 |
| ctggcgctca cctacggcta cagcttcggc gtcgagctca ccatcgacaa cgtcgtgcac | 900 |
| cagtacttct acgaccgctt cgacgtcaac ctccagaccg ccgggctcat cgccgccagc | 960 |
| ttcgggatgg ccaacatcat ctcccgcccc ggcggcgggc tactctccga ctggctctcc | 1020 |
| agccggtacg gcatgcgcgg caggctgtgg gggctgtgga ctgtgcagac catcggcggc | 1080 |
| gtcctctgcg tggtgctcgg aatcgtcgac ttctccttcg ccgcgtccgt cgccgtgatg | 1140 |
| gtgctcttct ccttcttcgt ccaggccgcg tgcgggctca ccttcggcat cgtgccgttc | 1200 |
| gtgtcgcgga ggtcgctggg gctcatctcc gggatgaccg gcggcggggg caacgtgggc | 1260 |
| gccgtgctga cgcagtacat cttcttccac ggcacaaagt acaagacgga gaccgggatc | 1320 |
| aagtacatgg ggctcatgat catcgcgtgc acgctgcccg tcatgctcat ctacttcccg | 1380 |
| cagtggggcg gcatgctcgt aggcccgagg aagggggcca cggcggagga gtactacagc | 1440 |
| cgggagtggt cggatcacga gcgcgagaag ggtttcaacg cggccagcgt gcggttcgcg | 1500 |
| gagaacagcg tgcgcgaggg cgggaggtcg tcggcgaatg gcggacagcc caggcacacc | 1560 |
| gtccccgtcg acgcgtcgcc ggccggggtg tgaagaatgc cacggacaat aaggtcgcgg | 1620 |
| ttgtagtaca actgtacaaa ttgatggtac gtgtcgtttg accgcgcgcg cgcacagtgt | 1680 |
| gggtcgtggc ctcgtgggct tagtggagta cagtgagggg tgtacgtgtg tcgtggcgcg | 1740 |

```
cgcggtcacc tcggtggcct tgggattggg ggggcactat acgctagtac tccagatata    1800
tacgggtttg atttacttct gtggatcggc gcttgttggt ggtttgctcc ctgtggtttt    1860
tgtgatggta atcatactca tactcaaaca gtc                                 1893
```

TRANSGENIC PLANTS EXPRESSING A PH-SENSITIVE NITRATE TRANSPORTER

RELATED APPLICATIONS AND INCORPORATION BY REFERENCE

This application is a continuation of U.S. application Ser. No. 14/642,858, filed Mar. 3, 2015, which is a continuation of U.S. application Ser. No. 14/172,294, filed Feb. 4, 2014, now U.S. Pat. No. 9,012,721, Issued Apr. 21, 2015, which is a continuation-in-part application of international patent application Serial No. PCT/CN2013/071384 filed Feb. 5, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to transgenic plants with improved traits, for example growth and nitrogen use efficiency expressing a nitrate transporter gene, methods of making such plants and methods for improving growth and nitrogen use efficiency.

INTRODUCTION

Global crop productivity has increased markedly during the past five decades mainly due to improved crop varieties and massive inputs of chemical fertilizers, especially nitrogen (N)[1,2]. However, fertilizer N use efficiency is only about 30-50% for many crops[2-4] with large proportions being lost to the environment, resulting in various detrimental impacts such as the degradation of air and water quality and losses of biodiversity[5,6]. It has been estimated that excess N in the environment is currently costing the European Union between € 70 billion and € 320 billion per year[7]. In China, the increase in grain production during the past 30 years has been accompanied by a dramatic decrease in the N use efficiency (NUE) from 55 to 20 kg grain per kg fertilizer N applied[3]. In Asia, rice provides more than 70% of the daily caloric intake of the population, but with the land available for agriculture diminishing, increasing demand can only be managed by increasing productivity.

It is therefore of major importance to identify the critical steps controlling plant NUE. NUE can be defined as being the yield of grain per unit of available N in the soil (including the residual N present in the soil and the fertilizer). Thus NUE can be divided into two processes: uptake efficiency (NupE; the ability of the plant to remove N from the soil as nitrate and ammonium ions) and the utilization efficiency (NutE; the ability to use N to produce grain yield). This challenge is particularly relevant to cereals for which large amounts of N fertilizers are required to attain maximum yield and for which NUE is estimated to be far less than 50% (Hirel et al).

Nitrogen (N) is fundamental to crop development as it forms the basic component of many organic molecules, nucleic acids and proteins. N nutrition affects all levels of plant function, from metabolism to resource allocation, growth, and development. The most abundant source for N acquisition by plant roots is nitrate ($NO_3^-$) in natural aerobic soils, due to intensive nitrification of applied organic and fertilizer N. By contrast, ammonium ($NH_4^+$) is the main form of available N in flooded paddy soils due to the anaerobic soil conditions (Sasakawa and Yamamoto, 1978).

Thus, soil inorganic nitrogen (N) is predominantly available for plants as nitrate in aerobic uplands and well-drained soils and as ammonium in poorly drained soils and flooded anaerobic paddy fields. In many plants the nitrate acquired by roots is transported to the shoots before being assimilated (Smirnoff and Stewart, 1985). By contrast, ammonium derived from nitrate reduction or directly from ammonium uptake is preferentially assimilated in the root and then transported in an organic form to the shoot (Xu et al., 2012). To cope with varied concentrations of nitrate in soils, plant roots have developed at least three nitrate uptake systems, two high-affinity transport systems (HATS) and one low-64 affinity transport system (LATS), responsible for the acquisition of nitrate (Crawford and Glass, 1998). The constitutive HATS (cHATS) and nitrate-inducible HATS (iHATS) operate to take up nitrate at low nitrate concentration in external medium with saturation in a range of 0.2-0.5 mM. In contrast, LATS functions in nitrate acquisition at higher external nitrate 68 concentration. The uptake by LATS and HATS is mediated by nitrate transporters belonging to the families of NRT1 and NRT2, respectively (Forde, 2000; Miller et al., 2007). Uptake by roots is regulated by negative feedback, linking the expression and activity of nitrate uptake to the N status of the plant (Miller et al., 2007). Several different N metabolites have been proposed to be cellular sensors of N status, including glutamine (Fan et al., 2006; Miller et al., 2008) and one model has root vacuolar nitrate as the feedback signal as these pools increase with plant N status.

Although higher plants have the capacity to utilize organic N, the major sources for N acquisition by roots are considered to be $NO_3^-$ and $NH_4$. Plants vary substantially in their relative adaptations to these two sources of N. Although $NH_4$ should be the preferred N source, since its metabolism requires less energy than that of $NO_3^-$, only a few species actually perform well when $NH_4$ is provided as the only N source. Among the latter are boreal conifers, ericaceous species, some vegetable crops, and rice (*Oryza sativa* L.). In contrast to these species, most agricultural species develop at times severe toxicity symptoms on $NH_4$ thus, superior growth in these species is seen on $NO_3^-$. However, when both N sources are provided simultaneously, growth and yield are often enhanced significantly compared with growth on either $NH_4$ or $NO_3^-$ alone (Kronzucker et al., 1999).

Rice, a major crop feeding almost 50% of the world's population therefore differs from other crop plants in that it is capable of growing exclusively on $NH_4$ as the only N source. Rice has been traditionally cultivated under flooded anaerobic soil conditions where ammonium is the main N source. However, the specialized aerenchyma cells in rice roots can transfer oxygen from the shoots to the roots and release it to the rhizosphere, where bacterial conversion of ammonium to nitrate (nitrification) can take place[8]. Nitrification in the waterlogged paddy rhizosphere can result in 25-40% of the total crop N being taken up in the form of nitrate, mainly through a high affinity transport system (HATS)[9]. The uptake of nitrate is mediated by cotransport with protons (H$^+$) that can be extruded from the cell by plasma membrane H$^+$-ATPases[10]. The molecular mechanisms of nitrate uptake and translocation in rice are not fully understood. Since the nitrate concentration in the rhizosphere of paddy fields is estimated to be less than 10 μM (Kirk and Kronzucker, 2005), NRT2 family members play a major role in nitrate uptake in rice (Araki and Hasegawa, 2006; Yan et al., 2011). In addition, rice roots have abundant aerenchyma for the transportation of oxygen into the rhizosphere, resulting in ammonium nitrification by bacteria on the root surface (Kirk, 2003; Li et al., 2008). Therefore, up to 40% of the total N taken up by rice roots grown under wetland conditions might be in the form of nitrate and the rates of uptake could be comparable with those of ammonium (Kronzucker et al., 2000; Kirk and Kronzucker, 2005).

Both electrophysiological and molecular studies have shown that nitrate uptake through both HATS and LATS is an active process mediated by proton/nitrate co-transporters (Zhou et al., 2000; Miller et al., 2007). In the *Arabidopsis* genome, there are at least 53 and 7 members belonging to NRT1 and NRT2 families, respectively (Miller et al., 2007; Tsay et al., 2007). Several *Arabidopsis* NRT1 and NRT2 family members have been characterized for their functions in nitrate uptake and long distance transport. AtNRT1.1 (CHL1) is described as a transceptor playing multiple roles as a dual affinity nitrate transporter and a sensor of external nitrate supply concentration (Liu and Tsay, 2003; Ho et al., 2009; Gojon et al., 2011), and auxin transport at low nitrate concentrations (Krouk et al., 2010). In contrast, AtNRT1.2 (NTL1) is a constitutively expressed low affinity nitrate transporter (Huang et al., 1999). AtNRT1.4 is a leaf petiole expressed nitrate transporter and plays a critical role in regulating leaf nitrate homeostasis and leaf development (Chiu et al., 2004). AtNRT1.5 is expressed in the root pericycle cells close to the xylem and is responsible for loading of nitrate into the xylem for root-to-shoot nitrate transport (Lin et al., 2008). AtNRT1.6 is expressed only in reproductive tissues and is involved in delivering nitrate from maternal tissue to the early developing embryo (Almagro et al., 2008). AtNRT1.7 functions in phloem loading of nitrate to allow transport out of older leaves and into younger leaves, indicating that source-to-sink remobilization of nitrate is mediated by the phloem (Fan et al., 2009). AtNRT1.8 is expressed predominantly in xylem parenchyma cells within the vasculature and plays the role in retrieval of nitrate from the xylem sap (Li et al., 2010). AtNRT1.9 facilitates loading of nitrate into the root phloem, enhancing downward transport in roots, and its knockout increases root to shoot xylem transport of nitrate (Wang and Tsay, 2011).

Among the 7 NRT2 family members in *Arabidopsis*, both AtNRT2.1 and AtNRT2.2 have been characterized as contributors to iHATS (Filleur et al., 2001). In addition, NRT2.1 transport activity requires a second accessory protein NAR2.1 (or NRT3.1) in *Arabidopsis* (Okamoto et al., 2006; Orsel et al., 2006; Yong et al., 2010). Knockout of AtNAR2.1 (atnar2.1 mutant) had more severe effects on both nitrate uptake at low nitrate concentrations and growth than knockout of its partner AtNRT2.1 (atnrt2.1 mutant) suggesting other functions for AtNAR2.1 (Orsel et al., 2006). Interestingly, AtNRT2.7 is expressed specifically in the vacuolar membrane of reproductive organs and controls nitrate content in seeds (Chopin et al., 2007). Recently, AtNRT2.4 has been found to be a high affinity plasma membrane nitrate transporter expressed in the epidermis of lateral roots and in or close to the shoot phloem (Kiba et al., 2012). AtNRT2.4 is involved in the uptake of NO$_3^-$ by the root at very low external concentration and in shoot NO$_3^-$ loading into the phloem and is important under N starvation (Kiba et al., 2012).

In the rice genome, five NRT2 genes have been identified (Araki and Hasegawa, 2006; Cai et al., 2008; Feng et al., 2011). OsNRT2.1 and OsNRT2.2 share an identical coding region sequence with different 5'- and 3'-untranscribed regions (UTRs) and have high similarity to the NRT2 genes of other monocotyledons, while OsNRT2.3 and OsNRT2.4 are more closely related to *Arabidopsis* NRT2 genes. OsNRT2.3 mRNA is actually spliced into two gene products, OsNRT2.3a (AK109776) and OsNRT2.3b (AK072215), with 94.2% similarity in their putative amino acid sequences (Feng et al., 2011, Yan et al., 2011). OsNRT2.3a is expressed mainly in roots and this pattern is enhanced by nitrate supply, while OsNRT2.3b is expressed weakly in roots and relatively abundantly in shoots with no effect of the N form and concentration on the amount of transcript (Feng et al., 2011, Feng 2012).

CN101392257 shows an expression analysis of OsNRT2.3a and b in rice and *Xenopus* oocytes and mentions overexpression of the OsNRT2.3 gene in plants. CN101392257 does not disclose separate expression of OsNRT2.3a and OsNRT2.3b in rice nor does it show that expressing OsNRT2.3b in plants other than rice which significantly differ in the use of N sources can have beneficial effects.

Citation or identification of any document in this application is not an admission that such document is available as prior art to the present invention.

SUMMARY OF THE INVENTION

There is a need to provide more nutrient efficient genotypes for crop plants to ensure sustainable crop production for global food security and to reduce the costs and negative environmental effects of mineral fertiliser input, such as of air and water quality and losses of biodiversity. The present invention is aimed at addressing this need.

The rice transporter OsNRT2.3 has two spliced forms. Some nitrate transporters require two genes for function; the second much smaller component (OsNAR21) is required for the correct targeting of the transporter protein to the plasma membrane. One of the two spliced forms, OsNRT2.3a, requires this second component for function, while the other form, OsNRT2.3b, does not. Applicants have demonstrated for the first time that expression of both nitrate transporters in *Xenopus* oocytes showed that only OsNRT2.3b had a pH-sensitive regulatory site on the cytoplasmic face of the protein. This pH sensing site was confirmed by site-directed mutagenesis of a histidine amino acid residue (H167R) in the pH sensing motif. In rice, OsNRT2.3b was more specifically localised in the vascular tissue, particularly the phloem. Applicants therefore suggest that the protein is specifically involved in long distance transport within the plant and that the phloem is important in whole plant pH regulation.

Applicants have over-expressed, independently, both OsNRT2.3a/b genes and the H167R mutated form of OsNRT2.3b using strong non-specific constitutive promoters (35S and ubiquitin) in several different Chinese cultivars of rice. Applicants have shown that only OsNRT2.3b overexpressing plants showed much improved growth and nitrogen use efficiency and the phenotype was surprising as both nitrate and ammonium uptake was increased in these OsNRT2.3b over-expressing plants. The OsNRT2.3b over-expressing plants showed less photorespiration and generally had better pH regulation (iron and phosphate contents) relative to controls or OsNRT2.3a over-expressing plants. The pH sensing motif of OsNRT2.3b is important for these effects in rice by linking the plant's pH status to nitrate supply.

Applicants have also surprisingly shown that OsNRT2.3b is functional when transgenically expressed in plants other than rice although these plants, such as *Arabidopsis*, wheat and tobacco, differ fundamentally in their use of nitrogen sources.

As can be seen from the following disclosure, the invention has several aspects. In some aspects, the invention relates to methods, uses and plants where rice is specifically disclaimed. In other aspects, the invention relates to methods, uses and plants where the expression of the OsNRT2.3b nucleic acid is regulated by a phloem specific promoter. In other aspects, the invention relates to methods, uses and plants that do not transgenically express a nucleic acid sequence which may comprise SEQ ID No. 2 or a functional variant thereof.

Thus, in a first aspect, the invention relates to methods for increasing one or more of growth, yield, nitrogen transport, NUE, nitrogen acquisition, decreasing photorespiration, increasing intercellular $CO_2$ levels, increasing photosynthetic efficiency, pathogen resistance, survival and maintaining/improving pH homeostasis which may comprise introducing and expressing a nucleic acid construct which may comprise SEQ ID No. 1, a functional variant, part or homolog thereof operably linked to a regulatory sequence in a plant.

In a second aspect, the invention relates to a method for increasing one or more of growth, yield, nitrogen use efficiency, nitrogen transport, nitrogen stress tolerance, pathogen resistance, survival and/or nitrogen acquisition of a plant which may comprise introducing and expressing a nucleic acid construct which may comprise a nucleic acid sequence as defined in SEQ ID No. 1, a functional variant, part or homolog thereof operably linked to a regulatory sequence in a plant wherein if the nucleic acid sequence is as defined in SEQ ID No. 1, a functional variant, part or homolog thereof said plant is not rice.

In a third aspect, the invention relates to a transgenic plant expressing a nucleic acid construct which may comprise a nucleic acid sequence as defined in SEQ ID No. 1, a functional variant, part or homolog thereof operably linked to a regulatory sequence into a plant wherein if the nucleic acid sequence is as defined in SEQ ID No. 1 said plant is not rice.

In another aspect, the invention relates to a method for regulating pH homeostasis which may comprise introducing and expressing a nucleic acid construct which may comprise a nucleic acid sequence which may comprise SEQ ID No. 1, a functional variant, part or homolog thereof operably linked to a regulatory sequence in a plant.

In another aspect, the invention relates to a method for reducing acidification in a plant which may comprise introducing and expressing a nucleic acid construct which may comprise a nucleic acid sequence which may comprise SEQ ID No. 1, a functional variant, part or homolog thereof operably linked to a regulatory sequence in a plant.

In another aspect, the invention relates to a method for altering nitrate transport and pH homeostasis in a plant which may comprise introducing and expressing a nucleic acid construct which may comprise a nucleic acid sequence which may comprise SEQ ID No. 1, a functional variant, part or homolog thereof operably linked to a regulatory sequence in a plant wherein said nucleic acid comprises a mutation in the pH sensing motif VYEAIHKI (SEQ ID No. 16).

In another aspect, the invention relates to a use of a nucleic acid which may comprise SEQ ID No. 1, a functional variant, part or homolog thereof which may comprise the pH sensing motif VYEAIHKI (SEQ ID No. 16) in regulating pH, altering nitrate transport and pH homeostasis in a plant.

In a further aspect, the invention relates to a method for increasing one or more of growth, yield, nitrogen use efficiency, nitrogen transport, nitrogen stress tolerance, pathogen resistance and/or nitrogen acquisition of a plant which may comprise introducing and expressing a nucleic acid construct which may comprise a nucleic acid sequence as defined in SEQ ID No. 1, a functional variant, part or homolog thereof operably linked to a regulatory sequence into a plant wherein said regulatory sequence is a constitutive promoter or a phloem specific promoter and wherein said plant does not overexpress a nucleic acid sequence which may comprise SEQ ID No. 2.

In another aspect, the invention relates to a method for making a transgenic plant having increased growth, yield, nitrogen transport, nitrogen acquisition, nitrogen stress tolerance and/or nitrogen use efficiency which may comprise a) introducing and expressing in a plant or plant cell a nucleic acid construct which may comprise a nucleic acid sequence as defined in SEQ ID No. 1, a functional variant, part or homolog thereof operably linked to a regulatory sequence wherein said regulatory sequence is a constitutive promoter or a phloem specific promoter and wherein said plant does not overexpress a nucleic acid sequence which may comprise SEQ ID No. 2.

In another aspect, the invention relates to a transgenic plant expressing a nucleic acid construct which may comprise a nucleic acid sequence as defined in SEQ ID No. 1, a functional variant, part or homolog thereof operably linked to a regulatory sequence into a plant wherein said regulatory sequence is a constitutive promoter or a phloem specific promoter and wherein said plant does not overexpress a nucleic acid sequence SEQ ID No. 2.

In another aspect, the invention relates to a transgenic plant expressing a nucleic acid construct which may comprise a nucleic acid sequence as defined in SEQ ID No. 1, a functional variant, part or homolog thereof operably linked to a phloem specific promoter and related methods.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

The invention is further described in the following non-limiting figures.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-E. The Nipponbare phenotype of OsNRT2.3a and OsNRT2.3b over-expression plants. (a) The T2 rice plants in paddy soil at vegetative (60 days). (b) Reproductive stages (120 days). (c) RT-PCR with the specific primers. (d) Western blot with mono-antibody to identify protein expression. (e) The RNA in situ hybridization in WT and b-S6 with negative probe control, p: phloem; x: xylem; e, epidermal cells; m; mesophyll cells. Cross sections are the 5-6 cm leaf section from the tip of first leaf of plants in (a). Scale bar=10 μm.

FIG. 2A-F. The field experiments of T2 OsNRT2.3b over-expression lines. (a) The growth of OsNRT2.3b over-expression lines b-U1, b-U2, b-S2 and b-S6 at different N fertilizer application rates (May-October 2010, the photographs were taken on 16 Sep. 2010) at Changxing experiment station, Zhejiang University. The N application was shown in the left corner of each picture with the Chinese label given in the middle of the field. (b) The plant grain yield for "a" conditions. (c) The NUE at "a" conditions. (d) Large scale experiment, 1280 seedlings of each type transferred into paddy soil. (e) Grain yield at "d" condition. (f) The NUE for "d" conditions. NUE: nitrogen use efficiency=g-grain yield/g-applied fertilizer N. Values are mean±S.E (n=3). * was above bars indicating significant level (*p<0.05) between the transgenic lines and WT at the same N fertilizer application rate estimated by ANOVA.

FIG. 3A-E. The effects of OsNRT2.3b over-expression on the influx of $^{15}NO_3^-$ and $^{15}NH_4^+$ by root, xylem $NO_3^-$ and $NH_4^+$, xylem pH, phloem pH acidification at 2.5 mM $NO_3^-$ or $NH_4^+$ condition. (a) The $^{15}N$ influx rate at nitrate or ammonium. (b) xylem $NO_3^-$ and $NH_4^+$ at nitrate or ammonium for 24 h. (c) xylem sap pH at nitrate or ammonium. (d) phloem pH acidification in nitrate or ammonium, phloem sap was collected by EDTA-$Na_2^{16}$. (e) Phloem pH acidification in nitrate or ammonium, phloem sap was collected by insects. Values are mean ±S.E (n=5). * was above bars indicating significant level (*p<0.05) between the transgenic lines and WT at the same treatment estimated by ANOVA. Bars from left to right in a-d: WT, b-U1, b-U2, b-S2, b-S6

FIG. 4A-C. The effects of OsNRT2.3b over-expression on the influx of different forms of N at pH 4 and 6. Bars from left to right: WT, b-U1, b-U2, b-S2, b-S6. (a) The $^{15}N$ influx in $NH_4^{15}NO_3$ supply. (b) The $^{15}N$ influx in $^{15}NH_4NO_3$ supply. (c) The $^{15}N$ influx in $^{15}NH_4^{15}NO_3$ supply. Values are mean±S.E (n=5). a, b, c letters were above bars indicating significant difference (p<0.05) between the transgenic lines and WT at the same treatment estimated by ANOVA.

FIG. 5A-D. The functional analysis of OsNRT2.3b in Xenopus ooctyes. (a) A double barreled pH electrode recording of cytosolic pH from an OsNRT2.3b injection oocyte, treated with 1 mM nitrate (shaded bar) and pH 8.0 saline (grey bar) washing. (b) The membrane potential to 1 mM nitrate (shaded bar) for an oocyte expressing H167R mutant of OsNRT2.3b. (c)$^{15}N$-nitrate uptake by oocytes injected with water, OsNRT2.3b mRNAs and its H167R mutant. (d)$^{15}N$-nitrate uptake by oocytes injected with water and OsNRT2.3b mRNAs at different external pH for over-night. Values are mean±S.E (n=15). Cells were tested by electrophysiology to be alive after incubation experiment. * was above bars indicating significant level (*p<0.05) estimated by ANOVA.

FIG. 6A-C. Plant fresh weight (A) and root length (B) tissue nitrate accumulation (C) data for three Arabidopsis lines over-expressing OsNRT2.3b compared with wild type (wt). Bars from left to right in (C): 23b.1, 23b.2, 23b.3, WT FIG. 7. Comparison of tobacco plants overexpressing OsNRT2.3b and WT plants: phenotype analysis. Growth differences of T1 OsNRT2.3b over-expression lines in sand-filled pots. WT: Nicotiana tabacum cultivar 89, T1 generation grown for 2 months in a complete Hoagland nutrient solution with 10 mM nitrate supply.

FIG. 8A-B. Comparison of tobacco plants overexpressing OsNRT2.3b and WT plants: expression analysis. A) Southern blot of OsNRT2.3b overexpression lines Kpn I, HindIII digested tobacco DNA of T1 generation and Hyb probe was used for hybridization Ld: marker, P: positive control, b-20 is a negative control. B) RT-PCR of OsNRT2.3b over-expression lines cDNA of T1 generation and OsNRT2.3b specific primer was used for the PCR.

FIG. 9. Biomass and NUE of tobacco overexpressing OsNRT2.3b lines grown in sand-filled pots WT: Nicotiana tabacum cultivar 89, T1 generation grown for 2 months in a complete Hoagland nutrient solution with 10 mM nitrate supply. NUE=biomass/total N application).

FIG. 10. The gene structure of OsNRT2.3a/b (SEQ ID No. 2 and 1, peptide OsNRT2.3a/b are SEQ ID No. 3 and 4). Analysis of the OsNRT2.3 genomic DNA sequence predicts an intron for OsNRT2.3b located between +190 bp to +280 bp from the ATG for translation initiation. For OsNRT2.3a the 5'-UTR is 42 bp and 249 bp 3'-UTR and for OsNRT2.3b the 5'-UTR is 223 bp and 316 bp 3'-UTR. F means the specific forward primer for OsNRT2.3b and R is the reward primer for OsNRT2.3b.

FIG. 11A-F. T2 OsNRT2.3b over-expression plants in the Nipponbare cultivar background in Hainan. a: The T2 Nipponbare transgenic plants were grown in Ledong Experimental Station of Nanjing Agricultural University, Hainan Province (December 2009-April 2010). The soil nutrient status before fertilizer addition was total nitrogen (N) 1.0±0.2 mg/g, total phosphorus (P) 0.4±0.1 mg/g, total potassium (K) 39.5±2.3 mg/g, 0.5 mM NaHCO3 extractable P (Olsen P) 23.1±4.1 mg/kg, soil pH 4.4±0.5 (sampling number was 6). The date for this picture was 28 Feb. 2010 and plants were grown for 75 days from germination at 75 kg N/ha N condition. All the planting and fertilizing information was described as FIG. SF7; b: plant panicle; c: panicle length; d, e: numbers of primary and second rachis; f: grain yield. Values are mean±S.E (n=10), * indicates significance of difference between WT and over-expression plants at 5% levels with One-way ANOVA analysis. Bars from left to right: WT, a-U1, a-U2, b-U-1, b-U2, b-S2, b-S6.

FIG. 12A-F. The phenotype of OsNRT2.3b over-expression lines in the WYJ7 cultivar background. a: Pot experiment done in Nanjing 2010. The T1 lines of 396-2, 369-1, 366-1 and 342-1 were over-expressed with OsNRT2.3b in comparison to its wild type (WT: WYJ7). Seeds were germinated at 20th May and the picture was taken on 20th October before harvest; b: Southern blot of T1 seedlings. Then the 396-2, 369-1, 366-1 and 342-1 lines were renamed as 396, 369, 366 and 342 for the T2 field experiments; c: RT-PCR with primers, 26 cycles were set for this PCR. d: T2 field experiments at the Experimental Station of Zhejiang University (May 2011-October 2011) with two application levels as 110 and 220 kg N/ha. Seeds were put to germinate on 5 May 2011, then 100 seedlings were transferred to the paddy field as 5 rows ×20 plants on 5th June and arranged randomly. Fertilizers were applied as in FIG. 2. The picture was taken on 10th October before harvest. The soil nutrient status before fertilizer addition was: total nitrogen (N) 1.68±0.21 mg/g, total phosphorus (P) 0.48±0.18 mg/g, total potassium (K) 46.47±2.85 mg/g, 0.5 mM NaHCO3-extractable P 38±2.1 mg/kg, soil pH 6.43±0.28 (n=6); e and f: The grain yield and NUE. Values are mean±S.E (n=3), * indicates significance of difference between WT and overexpression plants at 5% levels with One-way ANOVA analysis. Bars from left to right: WYT, 396, 369, 366, 342

FIG. 13A-D. The effect of OsNRT2.3b over-expression in the YF47 cultivar background. a: Plant growth performance of YF47 (wild type) and the transgenic plant with over-expression of NRT2.3b (YF/NRT2.3b(O)) in field trails at Hainan Experiment Station of Zhejiang University (December 2011-April 2012). Seeds were put to germinate on $10^{th}$ December and the photograph was taken on $1^{st}$ April, 15 days before the harvest; b: RT-PCR analysis of the transcript levels of NRT2.3b in YF47 (wild type) and the transgenic plants. c: Southern blot analysis of the transgenic plant; d: The grain yield per plant of YF47 and the transgenic plants. Values are mean±5.E (n=50). The soil nutrient status before fertilizer addition was: total nitrogen (N) 1.5±0.2 mg/g, total phosphorus (P) 0.3±0.1 mg/g, total potassium (K) 3.5±0.3 mg/g, 0.5 mM $NaHCO_3$-extractable P 24.1±4.7 mg/kg, soil pH 6.45±0.47 (n=9).

FIG. 14A-B. The T5 phenotype of OsNRT2.3b over-expression lines in the Nipponbare cultivar background. a: The T5 Nipponbare transgenic plants b-S2 and b-S6 were grown in Ledong Experimental Station of Nanjing Agricultural University, Hainan Province (December 2011-April 2012), 300 seeds were put to germinate on $10^{th}$ Dec. 200 seedlings were transferred to the paddy field on $5^{th}$ January. The picture was taken on the $13^{th}$ April before harvest. The experimental plot size was 20 m×25 m, 60 kg P/ha and 110 kg K/ha fertilizer was applied to the paddy before transferring the rice seedlings. Two N fertilizer levels were used 110 and 220 kg N/ha to the paddy. The first N fertilizer was applied as 20% of total N treatment before transplanting on $28^{th}$ December Second application at 40% of total was made at $12^{th}$ January. The final application was made at the $20^{th}$ January b: grain yield.

FIG. 16A-I. The phenotype difference between OsNRT2.3b over-expression plants and WT in pot experiments at late growth stage. This pot experiment was conducted as described in Table 1 and the growth was recorded at 76 days (a); 84 days (b); 88 days (c); 98 days (d); 120 days (e) and 140 days after transplant (f). The grain yield (g) total N (h) and $NU_tE$=grain weight/total N (i) of WT, b-S2 and b-S6 were measured at 120 and 140 days, separately. Values are mean±S.E (n=10), * indicates significance of difference between WT and over-expression plants at 5% levels with One-way ANOVA analysis. The pictures were taken only with WT and b-S6 because two plants were easily distinguished compared with all three plants in picture. Therefore black cloth was used as background and separated WT and b-S6 from b-S2, which was behind of the cloth in pot.

FIG. 17A-B. The method for phloem sap sampling from the Brown Plant Hopper (*Nilapavata lugens*). Rice seedlings were grown hydroponically in 1.25 mM $NH_4NO_3$ for 8 weeks and then transferred to N treatments (N: 2.5 mM $NO_3^-$; A: 2.5 mM $NH_4^+$). Each plant was placed in a 250 ml flask of IRRI nutrient solution with six plants kept in the insect cage at 26° C. and a 16 h light period. Seven to ten brown plant hopper adults were transferred on to each plant at the beginning of the N treatments. Rice phloem honey dew secreted by the insects was collected at 24 h, 48 h of the N treatments. Phloem sap pH was measured using a pH selective microelectrode[22]; a: phloem pH in nitrate; b: phloem pH in ammonium. Values are mean±S.E (n =10), * indicates significance of difference between WT and b-S6 at 5% levels with One-way ANOVA analysis.

FIG. 18A-C. The root apoplastic pH in the line b-S6 of OsNRT2.3b over-expression and WT after 72 h N treatment. Rice seedlings were grown in full nutrient solution containing 1.25 mM $NH_4NO_3$ for 4 weeks and then transferred to N treatments (N: 2.5 mM $NO_3^-$; A: 2.5 mM $NH_4^+$) for 72 h. a: the apoplastic pH of rice roots. After 72 h N treatment, the plant root was washed by dipping into 0.2 mM $CaSO_4$ for one minute before placement on the agar[17]. An intact plant was placed on agar (0.9 g/l, containing the pH indicator (0.03 g/L bromocresol purple[17]). The initial pH was 5.2-5.3 from 11:00-11:30 am, and roots were kept in darkness covered with a moist paper tissue and under a 0.5×12×12 $cm^3$ Plexiglas plate and picture was taken after 2-4 h in contact with the pH indicator agar; b: Agar profile showing apoplastic pH after removing the roots; c: the longer term pH change of the hydroponic growth medium during the N treatments.

FIG. 20A-C. The total photosynthesis, intercellular $CO_2$ concentration and photorespiration in plants over-expressing OsNRT2.3b compared with WT. The net photosynthesis, intercellular $CO_2$ concentration and photorespiration were measured using a Li-Cor 6400 infrared gas analyzer as described before[41]. a: total photosynthesis was calculated by net photosynthesis times the measured leaf area; b: intercellular $CO_2$ concentration; c: The net dark respiration ($R_n$) was reached during $CO_2$ PIB recording at stable recording stage from 100 to 200 seconds after shutting off lights, according to Supplemental FIG. 4 of Kebeish et al., 2007[22]. Values are mean±S.E (n=4), * indicates significance of difference between WT and over-expression plants at 5% levels with One-way ANOVA analysis.

FIG. 21A-D. The over-expression of OsNRT2.3b H167R mutant in Nipponbare. a: F1 generation plants of over-expression of OsNRT2.3b H167R mutant lines OvH1, OvH2 and WT in pot experiment (May.2012-September 2012) all the planting systems were the same as in Table 1. The photograph was taken on $10^{th}$ September; b: grain weight.

Values are mean±S.E (n=60); c: RT-PCR with the same primers for OsNRT2.3b, which covers the mutated site; d: southern blot.

FIG. 22. $^{15}$N—NH$_4^+$ uptake by oocytes injected with water or OsNRT2.3b mRNA. 0.5 mM $^{15}$N—NH$_4$Cl (atom % $^{15}$N 98%) was added into ND96 solution and the oocytes were incubated overnight (16 h). Values are mean±S.E (n=15).

FIG. 23A-D. The field design for the experiments shown in FIG. 2a and FIG. 2d. T2 field experiments were conducted in Changxing experiment station of Zhejiang University. For FIG. 2a the plants were transferred to the right blocks with four N application levels: no nitrogen, 75 kg N/ha, 150 kg N/ha and 300 kg N/ha; For FIG. 2d, plants were transferred to the left blocks with 75 kg N/ha supply. Each experimental block size was 20 m×30 m and 60 kg P/ha and 110 kg K/ha fertilizer was applied to the paddy before transferring the rice seedlings; b: the N treatments in each block; c: the plant arrangement in FIG. 2a with the same row and plant spaces as d; d: the plant arrangement in FIG. 2d. All field experiments were conducted with three replications randomly arranged.

Figures 24B, 25:
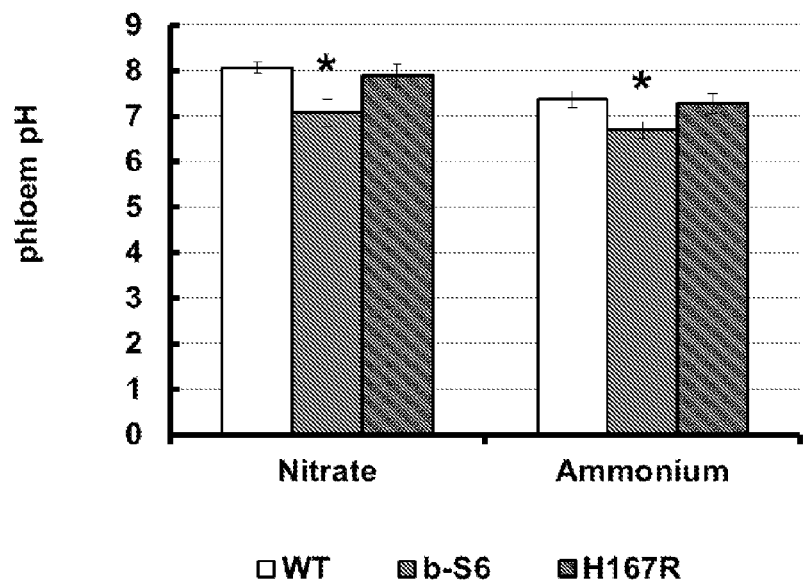

FIG. 24A-B. Table showing putative NRT2 nitrate transporters which have the pH-sensing motif that was identified in OsNRT2.3b.
  *best candidate for OsNRT2.3 orthologs
  Databases for searches: Blast sequence searches from phytozome 9 http://www.phytozome.net/
  Wheat database:
  http://www.cerealsdb.uk.net/CerealsDB/Documents/DOC_search_reads.php
  Barley database: http://webblast.ipk-gatersleben.de/barley/
  Membrane protein anion exchanger motifs (containing pH sensor) identified using
  http://www.bioinf.manchester.ac.uk/cgi-bin/dbbrowser/fingerPRINTScan/FPScan_fam.cgi FIG. 25. Overexpression OsNRT2.3b will enhance the phloem pH balancing. WT, wild type rice plant; b-S6, OsNRT2.3b over expression line; H167R, OsNRT2.3b H167R over expression line. The phloem pH was measured by pH selective electrode. Phloem sap was harvested by the Brown Plant Hopper (*Nilapavata lugens*) method. Rice seedlings were grown hydroponically in 1.25 mM NH$_4$NO$_3$ for 8 weeks and then transferred to N treatments (N: 2.5 mM NO$_3^-$; A: 2.5 mM NH$_4^+$). Each plant was placed in a 250 ml flask of IRRI nutrient solution with six plants kept in the insect cage at 26 C and a 16 h light period. Seven to ten brown plant hopper adults were transferred on to each plant at the beginning of the N treatments. Rice phloem honey dew secreted by the insects was collected at 24 h after the N treatments began. The results showed that WT and H167R line of phloem pH were same pattern at different N form however b-S6 was more near to 7 at nitrate treatment, more near neutral in both N conditions.

Figure 26:
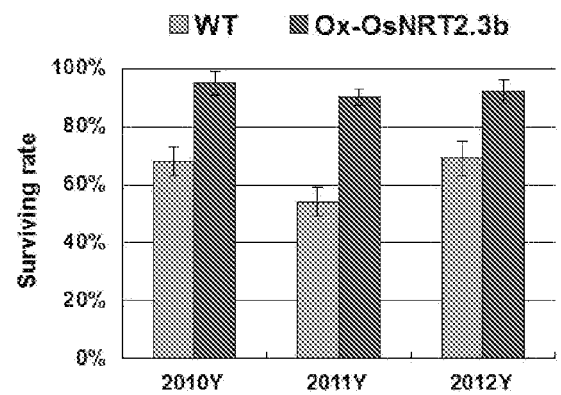

FIG. 26. Survival data for transgenic rice.

Figure 27:
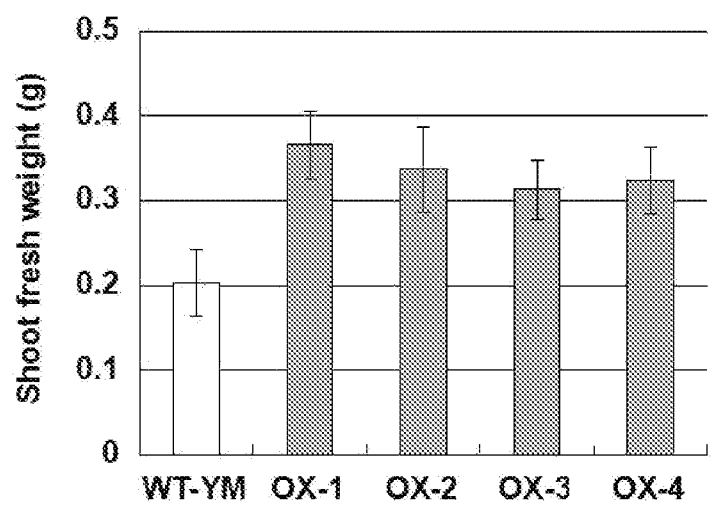

FIG. 27. The biomass of wheat OsNRT2.3b transgenic lines.

Figure 28:
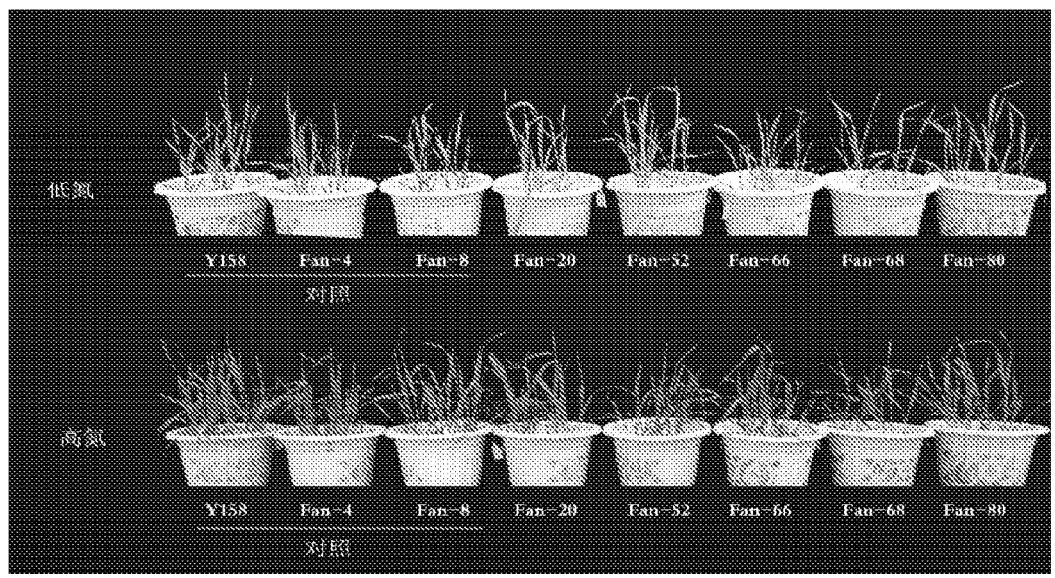

FIG. 28. The growth of wheat OsNRT2.3b transgenic lines in low and high N application.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

For the purposes of the invention, "transgenic", "transgene" or "recombinant" means with regard to, for example, a nucleic acid sequence, an expression cassette, gene construct or a vector which may comprise the nucleic acid sequence or an organism transformed with the nucleic acid sequences, expression cassettes or vectors according to the invention, all those constructions brought about by recombinant methods in which either
  (a) the nucleic acid sequences encoding proteins useful in the methods of the invention, or
  (b) genetic control sequence(s) which is operably linked with the nucleic acid sequence according to the invention, for example a promoter, or
  (c) a) and b)
are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 both incorporated by reference.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the different embodiments of the invention are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place.

The aspects of the invention involve recombination DNA technology and exclude embodiments that are solely based on generating plants by traditional breeding methods.

The OsNRT2.3b peptide expressed according to the aspects of the invention is shown in SEQ ID No. 3. According to the aspects of the invention, nucleic acid sequence SEQ ID No. 1 (OsNRT2.3b) encodes polypeptide SEQ ID No. 3 (OsNRT2.3b). Nucleic acid sequence SEQ ID No. 2 (OsNRT2.3a) encodes polypeptide SEQ ID No. 4 (OsNRT2.3a). Constructs that may comprise SEQ ID No. 67 which corresponds to accession No. AK072215 of OsNRT2.3b according to all embodiments and aspects of the invention. When referring to a nucleic acid encoding to OsNRT2.3a, this also refers to accession No. AK0109776 of OsNRT2.3a as shown in SEQ ID No. 68 according to all embodiments and aspects of the invention.

The inventors have demonstrated that over-expressing OsNRT2.3b in different rice cultivars increased grain yield by up to 40% and improved NUE under both low and high N inputs in extensive field trials. Photorespiratory gene expression was decreased in rice over-expressing OsNRT2.3b showing that improved photosynthetic efficiency is a component of the enhanced yield phenotype. Interestingly, the OsNRT2.3b over-expression lines, which were confirmed at both transcript and protein levels (FIG. 1c, d), showed more growth compared with wild type (WT) (FIG. 1a, b, FIG. 11). The biomass and panicle size of over-expression lines was greater than WT (FIG. 11, Table 2-3). The primary and second rachis size was increased, therefore the total number of seeds per panicle was greater than WT (FIG. 11, Table 2). By contrast, the OsNRT2.3a over-expression plants did not show visible difference from WT even though OsNRT2.3a mRNA and protein was increased in the transformed lines (FIG. 1c, d, FIG. 11).

Over-expressing OsNRT2.3b also improved pH homeostasis that resulted in increased total N uptake, shoot P and Fe accumulation. These results demonstrate that linking N uptake to pH homeostasis and photosynthesis is a key consideration for improving NUE and yield.

Thus, the inventors have demonstrated that OsNRT2.3b, but not OsNRT2.3a, can be used to improve growth, yield and nitrogen use efficiency and other traits when expressed in a plant. Accordingly, in some aspects, the invention relates to methods, uses and plants expressing a nucleic acid sequence which may comprise a nucleic acid as defined as defined in SEQ ID No. 1 (OsNRT2.3b), a functional variant, part or homolog thereof, but wherein said plant does not expressing a nucleic acid sequence which may comprise a nucleic acid as defined as defined in SEQ ID No. 2 (OsNRT2.3a). In particular, the invention therefore relates to methods for increasing growth, yield, nitrogen transport, pathogen resistance, NUE and/or nitrogen acquisition which may comprise introducing and expressing a nucleic acid construct which may comprise a nucleic acid sequence as defined in SEQ ID No. 1 (OsNRT2.3b) operably linked to a regulatory sequence into a plant wherein said regulatory sequence is a constitutive promoter or a phloem specific promoter and wherein said plant does not overexpress a nucleic acid sequence which may comprise SEQ ID No. 2 (OsNRT2.3a).

The invention has a further aspect. As mentioned above, rice differs from all other major crop in its nitrogen metabolism. Surprisingly, the inventors have shown that expression of OsNRT2.3b from rice, a plant that is, in contrast to all other major crop plants, capable of growing vigorously on $NH_4$, is active when expressed in other plant species that use $NO_3^-$ as their nitrogen source. Moreover, expression of OsNRT2.3b in other plants leads to a beneficial phenotype that shows improved growth, yield and nitrogen use efficiency, not only in rice, but also other plants. Thus, OsNRT2.3b from rice can be used in methods for improving growth, yield, pathogen resistance and nitrogen use efficiency in plants according to the invention. For example, overexpression of OsNRT2.3b in tobacco or in wheat increases biomass as shown in the examples.

Thus, the invention also relates to a method for increasing growth, yield, NUE, nitrogen acquisition, nitrogen stress tolerance, pathogen resistance and/or nitrogen transport of a plant which may comprise introducing and expressing a nucleic acid sequence which may comprise a nucleic acid as defined as defined in SEQ ID No. 1, a functional variant, part or homolog thereof operably linked to a regulatory sequence in a plant wherein if the nucleic acid sequence is as defined in SEQ ID No. 1 or a functional variant, part thereof said plant is not rice. In a preferred embodiment, the invention relates to a method for increasing growth, yield, NUE, nitrogen acquisition, nitrogen stress tolerance, pathogen resistance and/or nitrogen transport of a plant that is not rice which may comprise introducing and expressing a nucleic acid sequence which may comprise a nucleic acid as defined as defined in SEQ ID No. 1, a functional variant or part thereof operably linked to a regulatory sequence in said plant.

In another aspect, the invention relates to a method for increasing growth, yield, NUE, nitrogen acquisition, pathogen resistance, nitrogen stress tolerance and/or nitrogen transport of a plant which may comprise introducing and expressing a nucleic acid sequence which may comprise or as defined in SEQ ID No. 1, a functional variant, part or homolog thereof operably linked to a regulatory sequence in a plant wherein said plant is not rice.

Thus, in one aspect, the invention relates to a method for increasing growth of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice.

In yet another aspect, the invention relates to a method for increasing yield of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice.

The term "yield" includes one or more of the following non-limitative list of features: early flowering time, biomass (vegetative biomass (root and/or shoot biomass) or seed/grain biomass), seed/grain yield, seed/grain viability and germination efficiency, seed/grain size, starch content of grain, early vigour, greenness index, increased growth rate, delayed senescence of green tissue. The term "yield" in general means a measurable produce of economic value, typically related to a specified crop, to an area, and to a period of time. Individual plant parts directly contribute to yield based on their number, size and/or weight. The actual yield is the yield per square meter for a crop and year, which is determined by dividing total production (includes both harvested and appraised production) by planted square meters.

Thus, according to the invention, yield may comprise one or more of and can be measured by assessing one or more of: increased seed yield per plant, increased seed filling rate, increased number of filled seeds, increased harvest index, increased viability/germination efficiency, increased number or size of seeds/capsules/pods/grain, increased growth or increased branching, for example inflorescences with more branches, increased biomass or grain fill. Preferably, increased yield may comprise an increased number of grain/seed/capsules/pods, increased biomass, increased growth, increased number of floral organs and/or floral increased branching. Yield is increased relative to a control plant.

For example, the yield is increased by 2%, 3%, 4%, 5%-50% or more compared to a control plant, for example by at least 10%, 15%, 20%, 25%, 30%, 35%, 40%, 45% or 50%.

In another aspect, the invention relates to a method for increasing NUE of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice. In another aspect, the invention relates to a method for increasing NUE of a plant which may comprise introducing and expressing a nucleic acid sequence which may comprise SEQ ID No. 1, a functional variant, part or homolog thereof operably linked to a regulatory sequence in a plant wherein said plant is not rice.

In one embodiment, the method improves NUE under high N input. In another embodiment, the method improves NUE under low N input.

NUE can be defined as being the yield of grain per unit of available N in the soil (including the residual N present in the soil and the fertilizer). The overall N use efficiency of plants may comprise both uptake and utilization efficiencies and can be calculated as UpE.

For example, the NUE is increased by 5%-50% or more compared to a control plant, for example by at least 10%, 15%, 20%, 25%, 30%, 35%, 40%, 45% or 50%.

In another aspect, the invention relates to a method for increasing nitrogen acquisition of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice. In another aspect, the invention relates to a method for increasing nitrogen acquisition of a plant which may comprise introducing and expressing a nucleic acid sequence which may comprise SEQ ID No. 1, a functional variant, part or homolog thereof operably linked to a regulatory sequence in a plant wherein said plant is not rice.

For example, the nitrogen acquisition is increased by 10%-50% or more compared to a control plant, for example by at least 10%, 15%, 20%, 25%, 30%, 35%, 40%, 45% or 50%.

In one embodiment of the various methods described herein for increasing NUE, growth, yield, nitrogen acquisition and/or nitrate transport, said traits are increased under stress conditions, for example nitrogen stress.

In another aspect, the invention relates to a method for increasing nitrogen stress tolerance of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice. In another aspect, the invention relates to a method for increasing nitrogen stress tolerance of a plant which may comprise introducing and expressing a nucleic acid sequence which may comprise SEQ ID No. 1, a functional variant, part or homolog thereof operably linked to a regulatory sequence in a plant wherein said plant is not rice.

In another aspect, the invention relates to a method for increasing nitrogen transport of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice. In another aspect, the invention relates to a method for increasing nitrogen transport of a plant which may comprise introducing and expressing a nucleic acid sequence which may comprise SEQ ID No. 1, a functional variant, part or homolog thereof operably linked to a regulatory sequence in a plant wherein said plant is not rice.

In another aspect, the invention relates to a method for increasing pathogen resistance and/or survival of a plant which may comprise introducing and expressing a nucleic acid sequence which may comprise SEQ ID No. 1, a functional variant, part or homolog thereof operably linked to a regulatory sequence in a plant wherein if the nucleic acid sequence is as defined in SEQ ID No. 1 said plant is not rice. In another aspect, the invention relates to a method for increasing pathogen resistance and/or survival of a plant which may comprise introducing and expressing a nucleic acid sequence which may comprise SEQ ID No. 1, a functional variant, part or homolog thereof operably linked to a regulatory sequence in a plant wherein said plant is not rice.

The pathogen can for example be *Fusarium* wilt. Other pathogens known to the skilled persons are also within the scope of the invention.

The terms "regulatory element", "regulatory sequence", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. Furthermore, the term "regulatory element" includes downstream transcription terminator sequences. A transcription terminator is a section of nucleic acid sequence that marks the end of a gene or operon in genomic DNA during transcription. Transcription terminator used in construct to express plant genes are well known in the art.

In one embodiment, the constructs described herein have a promoter and a terminator sequence.

A "plant promoter" may comprise regulatory elements, which mediate the expression of a coding sequence segment in plant cells. Accordingly, a plant promoter need not be of plant origin, but may originate from viruses or microorganisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or may comprise a suitable promoter which expresses the gene at the right point in time and with the required spatial expression pattern. The term "operably linked" as used herein refers to a functional linkage between the promoter sequence and the gene of interest, such that the promoter sequence is able to initiate transcription of the gene of interest.

The following promoters may be selected according to the aspects of the invention. This list is not limiting.

A "constitutive promoter" refers to a promoter that is transcriptionally active during most, but not necessarily all, phases of growth and development and under most environmental conditions, in at least one cell, tissue or organ. Examples of constitutive promoters include but are not limited to actin, HMGP, CaMV19S, GOS2, rice cyclophilin, maize H3 histone, alfalfa H3 histone, 34S FMV, rubisco small subunit, OCS, SAD1, SAD2, nos, V-ATPase, super promoter, G-box proteins and synthetic promoters.

A "strong promoter" refers to a promoter that leads to increased or overexpression of the gene. Examples of strong promoters include, but are not limited to, CaMV-35S, CaMV-35Somega, *Arabidopsis* ubiquitin UBQ1, rice ubiquitin, actin, or Maize alcohol dehydrogenase 1 promoter (Adh-1).

In a preferred embodiment, the promoter is a constitutive promoters that is a strong promoter and directs overexpression of the gene of interest to which it is operably linked. Preferred promoters are CaMV-35S, CaMV-35Somega and *Arabidopsis* ubiquitin UBQ1.

The term "increased expression" or "overexpression" as used herein means any form of expression that is additional to the control, for example wild-type, expression level.

In one embodiment, the promoter is a phloem-specific promoter. Phloem-specific expression may be important for the function of the OsNRT2.3b, as the vascular tissue is important for pH regulation and it has recently been shown that nitrate transport in the phloem occurs in plants and may be a significant route for nitrogen delivery to the shoot.

A phloem specific promoter is, for example, from RSS1P, derived from the rice sucrose synthase gene (corresponding to SEQ ID No. 5 or a functional variant or part thereof, see Saha et al). Other phloem-specific promoters are known in the art.

According to the various aspects of the invention, growth, yield, nitrogen transport, nitrogen acquisition, nitrogen stress tolerance, pathogen resistance and/or nitrogen use efficiency is increased compared to a control plant. A control plant is a plant which has not been transformed with a nucleic acid construct which may comprise SEQ ID No. 1, a functional variant, part or homolog thereof, preferably a wild type plant. The control plant is preferably of the same species as the transgenic plant. Furthermore, the control plant may comprise genetic modifications, including expression of other transgenes.

The terms "increase", "improve" or "enhance" as used according to the various aspects of the invention are interchangeable. Growth, yield, nitrogen transport, nitrogen acquisition, nitrogen stress tolerance and/or nitrogen use efficiency is increased by about 5-50%, for example at least 5%, 6%, 7%, 8%, 9% or 10%, preferably at least 15% or 20%, more preferably 25%, 30%, 35%, 40%, 45% or 50% or more in comparison to a control plant. Preferably, growth is measured by measuring hypocotyl or stem length. In one embodiment, yield is increased by at least 40%.

The nucleic acid construct which may comprise SEQ ID No. 1, a functional variant, part or homolog thereof may also comprise a selectable marker which facilitates the selection of transformants, such as a marker that confers resistance to antibiotics, for example kanamycin.

In another aspect, the invention relates to a method for making a transgenic plant having increased yield, growth, nitrogen transport, nitrogen acquisition, nitrogen stress tolerance, pathogen resistance and/or nitrogen use efficiency which may comprise introducing and expressing in a plant or plant cell a nucleic acid sequence which may comprise SEQ ID No. 1, a functional variant, part or homolog thereof operably linked to a regulatory sequence wherein if the nucleic acid sequence is as defined in SEQ ID No. 1 said plant is not rice. In another aspect, the invention relates to a method for making a transgenic plant having increased yield, growth, nitrogen transport, nitrogen acquisition, nitrogen stress tolerance and/or nitrogen use efficiency which may comprise introducing and expressing in a plant or plant cell a nucleic acid sequence which may comprise SEQ ID No. 1, a functional variant, part or homolog thereof operably linked to a regulatory sequence wherein said plant is not rice.

The method further may comprise regenerating a transgenic plant from the plant or plant cell after step a) wherein the transgenic plant may comprise in its genome SEQ ID No. 1, a functional variant, part or homolog thereof operably linked to a regulatory sequence and obtaining a progeny plant derived from the transgenic plant wherein said progeny plant exhibits increased yield, growth, nitrogen transport, nitrogen acquisition, nitrogen stress tolerance and/or nitrogen use efficiency.

In one embodiment of these methods described above which explicitly exclude rice, the nucleic acid sequence may comprise or consists of SEQ ID No. 1 or a functional variant or part thereof.

Thus, according to the various aspects of the invention, SEQ ID No. 1, a functional variant, part or homolog thereof is introduced into a plant and expressed as a transgene. The nucleic acid sequence is introduced into said plant through a process called transformation. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The various aspects of the invention described herein clearly extend to any plant cell or any plant produced, obtained or obtainable by any of the methods described herein, and to all plant parts and propagules thereof unless otherwise specified. For example, in certain aspects described above, rice is specifically excluded. Thus, the methods exclude embodiments where a nucleic acid which may comprise or consist of SEQ ID No. 1 or a functional part of variant thereof are is expressed in rice. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The plant of the various aspects of the invention is characterised in that it shows increased growth, yield, nitrogen transport, nitrogen acquisition, nitrogen stress tolerance and/or nitrogen use efficiency.

The invention also extends to harvestable parts of a plant of the invention as described above such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins.

The invention also relates to the use of a sequence which may comprise SEQ ID No. 1, a functional variant, part or homolog thereof in increasing growth, yield, NUE, nitrogen acquisition, nitrogen stress tolerance, pathogen resistance and/or nitrogen transport of a plant wherein if the SEQ may comprise SEQ ID No. 1, said plant is not rice. Further, the invention also relates to the use of a sequence which may comprise SEQ ID No. 1, a functional variant, part or homolog thereof in increasing growth, yield, NUE, nitrogen acquisition, nitrogen stress tolerance and/or nitrogen transport of a plant wherein said plant is not rice.

The invention also relates to a nucleic acid construct which may comprise nucleic acid sequence SEQ ID No. 1, a functional variant, part or homolog operably linked to a phloem specific promoter, for example a nucleic acid which may comprise SEQ ID No. 5. Further provided is the use of the construct in the methods described herein.

Also provided is an isolated cell, preferably a plant cell or an *Agrobacterium tumefaciens* cell, expressing a nucleic acid construct which may comprise nucleic acid sequence SEQ ID No. 1, a functional variant, part or homolog operably linked to a phloem specific promoter. In another aspect, the invention relates to an isolated cell, preferably a plant cell or an *Agrobacterium tumefaciens* cell expressing a nucleic acid construct which may comprise nucleic acid sequence SEQ ID No. 1, a functional variant, part or homolog operably linked to a constitutive promoter. Furthermore, the invention also relates to a culture medium which may comprise an isolated plant cell or an *Agrobacterium tumefaciens* cell expressing a nucleic acid construct of the invention.

Unless rice is specifically disclaimed, the transgenic plant according to the various aspects of the invention described herein may be any monocot or a dicot plant provided for the embodiments described herein.

A dicot plant may be selected from the families including, but not limited to Asteraceae, Brassicaceae (eg *Brassica napus*), *Chenopodiaceae, Cucurbitaceae*, Leguminosae (Caesalpiniaceae, Aesalpiniaceae *Mimosaceae*, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, yam, *capsicum*, tobacco, cotton, okra, apple, rose, strawberry, alfalfa, bean, soybean, field (fava) bean, pea, lentil, peanut, chickpea, apricots, pears, peach, grape vine or citrus species. In one embodiment, the plant is oilseed rape.

Also included are biofuel and bioenergy crops such as rape/canola, sugar cane, sweet sorghum, *Panicum virgatum* (switchgrass), linseed, lupin and willow, poplar, poplar hybrids, *Miscanthus* or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, *petunia*, roses, geranium, *Nicotiana* sp.) and plants and cut flowers for the home (African violets, Begonias, chrysanthemums, geraniums, *Coleus* spider plants, Dracaena, rubber plant).

A monocot plant may, for example, be selected from the families Arecaceae, Amaryllidaceae or Poaceae. For example, the plant may be a cereal crop, such as wheat, barley, maize, oat, sorghum, rye, millet, buckwheat, turf grass, Italian rye grass, sugarcane or *Festuca* species, or a crop such as onion, leek, yam or banana. In one embodiment of the methods and plants described above, the plant is not rice.

Preferably, the plant is a crop plant. By crop plant is meant any plant which is grown on a commercial scale for human or animal consumption or use.

Most preferred plants are maize, wheat, oilseed rape, sorghum, soybean, potato, tobacco tomato, tobacco, grape, barley, pea, bean, field bean, lettuce, cotton, sugar cane, sugar beet, broccoli or other vegetable brassicas or poplar.

In one embodiment, the plant is wheat. In one embodiment, the plant is tobacco. Preferably, the promoter is a phloem specific promoter as described herein.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned may comprise the gene/nucleic acid of interest. The term "plant" also encompasses plant cells, suspension cultures, callus tissue, embryos, meristematic regions, gametophytes, sporophytes, pollen and microspores, again wherein each of the aforementioned may comprise the gene/nucleic acid of interest.

Plants or parts thereof obtained or obtainable by the method for making a transgenic plant as described above are also within the scope of the invention.

In another aspect, the invention relates to a transgenic plant expressing a nucleic acid sequence which may comprise SEQ ID No. 1, a functional variant, part or homolog thereof operably linked to a regulatory sequence into a plant wherein if the nucleic acid sequence is as defined in SEQ ID No. 1 said plant is not rice. Thus, this aspect of the invention excludes transgenic rice expressing a nucleic acid which may comprise or consist of SEQ ID No. 1. In one embodiment, other plants that are capable of growing on $NH_4$ as the sole nitrogen source are also excluded.

In another aspect, the invention relates to a transgenic plant expressing a nucleic acid sequence which may comprise SEQ ID No. 1, a functional variant, part or homolog thereof operably linked to a phloem specific promoter in a plant. The plant may be any monocot or dicot plant, including rice. In one embodiment, said plant is not rice In another aspect, the invention relates to a transgenic plant expressing a nucleic acid sequence which may comprise SEQ ID No. 1, a functional variant, part or homolog thereof operably linked to a regulatory sequence into a plant wherein said plant is not rice. In one embodiment, the transgenic plant expresses a nucleic acid sequence which may comprise or consist of SEQ ID No. 1.

The plant is characterised in that it shows increased yield, growth, nitrogen transport, nitrogen acquisition, nitrogen stress tolerance, pathogen resistance and/or nitrogen use efficiency.

The term "functional variant of a nucleic acid sequence" as used herein with reference to SEQ ID No. 1 or another sequence refers to a variant gene sequence or part of the gene sequence which retains the biological function of the full non-variant sequence, for example confers increased growth or yield when expressed in a transgenic plant. A functional variant also may comprise a variant of the gene of interest which has sequence alterations that do not affect function, for example in non-conserved residues. Also encompassed is a variant that is substantially identical, i.e. has only some sequence variations, for example in non-conserved residues, compared to the wild type sequences as shown herein and is biologically active.

Thus, specifically included in the scope is a functional part of a nucleic acid sequence as used herein with reference to SEQ ID No. 1 or another sequence which retains the biological function of the full non-variant sequence, for example confers increased growth or yield when expressed in a transgenic plant.

Thus, it is understood, as those skilled in the art will appreciate, that the aspects of the invention, including the methods and uses, encompasses not only a nucleic acid sequence which may comprise or consisting or SEQ ID No. 1, but also functional variants or parts of SEQ ID No. 1 that do not affect the biological activity and function of the resulting protein. Alterations in a nucleic acid sequence which result in the production of a different amino acid at a given site that do however not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

A functional variant of SEQ ID No. 1 has at least 90%, 91%, 92%, 93%, 94%, 95%, 96%, 97%, 98%, or 99% overall sequence identity to the amino acid represented by SEQ ID NO: 1. A functional variant of SEQ ID NO. 3 has at least 90%, 91%, 92%, 93%, 94%, 95%, 96%, 97%, 98%, or 99% overall sequence identity to the amino acid represented by SEQ ID No: 3. A functional variant retains the pH sensing motif.

A functional homolog of SEQ ID No. 1 is a nucleic acid encoding a NRT2.3b peptide which is biologically active in the same way as SEQ ID No. 1, in other words, for example it confers increased yield or growth. The term functional homolog includes OsNRT2.3b orthologs in other plant species.

The homolog of a OsNRT2.3b polypeptide has, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID No: 3. Preferably, overall sequence identity is 90%, 91%, 92%, 93%, 94%, 95%, 96%, 97%, 98%, or 99%. In another embodiment, the OsNRT2.3b nucleic acid sequence has, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the nucleic acid represented by SEQ ID No: 1. Preferably, overall sequence identity is 90%, 91%, 92%, 93%, 94%, 95%, 96%, 97%, 98%, or 99%. The overall sequence identity is determined using a global alignment algorithm known in the art, such as the Needleman Wunsch algorithm in the program GAP (GCG Wisconsin Package, Accelrys).

Preferably, the OsNRT2.3b homolog/ortholog has the pH sensing motif VYEAIHKI on the cytoplasmic side. In one embodiment, the homolog of a OsNRT2.3b polypeptide has 90%, 91%, 92%, 93%, 94%, 95%, 96%, 97%, 98%, or 99% overall sequence identity to the amino acid represented by SEQ ID No: 3 and may comprise the pH sensing motif VYEAIHKI (SEQ ID No. 16). Functional variants or parts of the homologs, for examples as shown in SEQ ID No. 6-15, are also included in the scope of the invention.

FIG. 24 shows examples of homologs/orthologs which have the pH sensing motif identified in OsNRT2.3b. Thus, preferred orthologous genes or peptides used according to the various aspects of the invention are selected from the orthologous listed in FIG. 24, including barley, maize, soybean, Brachypodium (SEQ ID Nos. 6-15) and wheat. Variants of these sequences that have at least 90%, 91%, 92%, 93%, 94%, 95%, 96%, 97%, 98%, or 99% to the sequences listed in SEQ ID NO. 6-15 are also within the scope of the invention.

Suitable homologs or orthologs can be identified by sequence comparisons and identifications of conserved domains. The function of the homolog or ortholog can be identified as described herein and a skilled person would thus be able to confirm the function when expressed in a plant.

For example, according to the various aspects of the invention, a nucleic acid encoding an endogenous NRT2.3 peptide may be expressed in any plant as defined herein unless otherwise specified by recombinant methods. As described above, in certain aspects of the invention, in particular when the nucleic acid construct may comprise or consists of SEQ ID No. 1, the plant is not rice. For example, rice OsNRT2.3b may be expressed in rice and a wheat NRT2.3b may be expressed in wheat.

In another embodiment, a nucleic acid encoding a plant NRT2.3b that is endogenous to a first plant species may be expressed in a second plant using recombinant methods. For example, a OsNRT2.3b homolog from another plant may be expressed in rice.

In one preferred embodiment of the various aspects of the invention, OsNRT2.3b which may comprise SEQ ID No. 1 or a functional variant thereof is expressed in another plant that is not rice. As the inventors have surprisingly shown, expression of OsNRT2.3b does lead to beneficial phenotypes in other plants that use a different N source. For example, expression may be in a monocot or dicot plant as described herein. In one embodiment, the plant is wheat or tobacco.

Thus, the invention specifically relates to a method for increasing one or more of growth, yield, nitrogen transport, NUE, nitrogen acquisition, decreasing photorespiration, increasing intercellular $CO_2$ levels, increasing photosynthetic efficiency, pathogen resistance and maintaining/improving pH homeostasis which may comprise introducing and expressing a nucleic acid sequence which may comprise SEQ ID No. 1, or a functional variant thereof in another plant that is not rice. Transgenic non-rice plants expressing a nucleic acid sequence which may comprise SEQ ID No. 1, or a functional variant, part thereof are also encompassed in the scope of the invention, for example wheat or tobacco.

Plants and their endogenous NRT2.3b may be selected from any plant, such as from one of the families or species listed herein.

*Arabidopsis* does not have a close relative to OsNRT2.3, the closest is AtNRT2.5, but this does not have a similar pH-sensing motif. A key aspect of the improved NUE associated with OsNRT2.3b is pH sensitivity of the nitrate transport function. The cytoplasmic pH sensing motif in OsNRT2.3b, that is absent from OsNRT2.3a, provides a link between nitrogen nutrition and pH regulation. The presence of a pH sensing motif is therefore important for homologs/orthologs in other species.

Homologs/orthologs of OsNRT2.3b can therefore be identified by the presence of a cytoplasmic pH sensing motif. In one aspect, the invention relates to a method for identifying OsNRT2.3b homologs/orthologs in other species which may comprise identifying peptides which may comprise the cytoplasmic pH sensing motif.

Figure 18C:
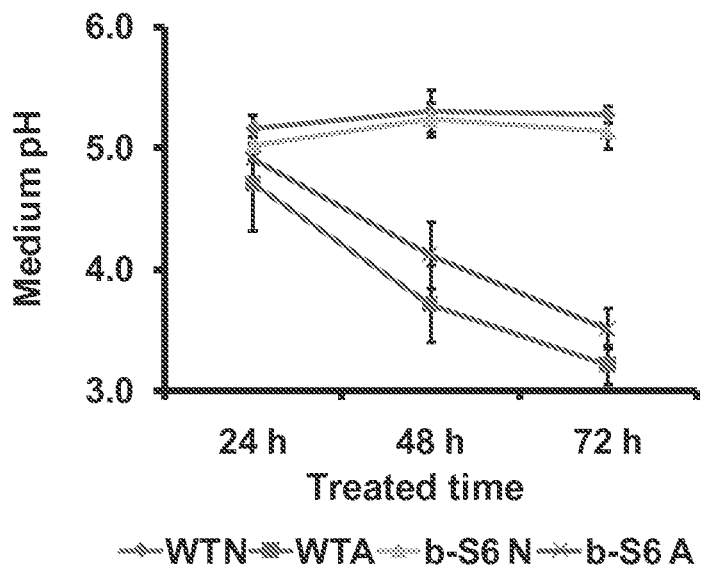

As explained in the examples, when over-expressing OsNRT2.3b in rice, xylem pH was 7 and 7.3 in WT treated respectively with nitrate and ammonium, while it was 7.5 and 7.6-7.8 in the OsNRT2.3b over-expressing lines, significantly higher than WT. After 24 h N treatments, phloem sap was collected. The phloem sap pH was measured and less acidification was found in OsNRT2.3b over-expression lines. The difference between WT and over-expression lines was about 0.2 pH units in nitrate and about 0.1 pH units in ammonium. WT phloem pH decreased from 7.8 to 6.1 and b-S6 from 6.7 to 6.0 in nitrate supply from 24 to 48 h treatments; while in ammonium treatment WT phloem pH decreased from 7.4 to 6.3 and b-S6 from 6.6 to 5.9 from 24 to 48 h. The difference between WT and b-S6 under nitrate supply was remarkably high at 24 h, however no significant difference was found by 48 h. In ammonium supply, although the pH in WT sap was higher than in b-S6 the difference was not significant. The acidification of WT phloem pH in nitrate was about 1.7 pH units however it was only 0.7 of a pH unit in the b-S6 plants. By 48 h the collected phloem pH sap had adjusted to give more similar values for WT and b-S6 plants (FIG. 17b). Furthermore the root apoplastic pH in WT and b-S6 roots was tested with bromocresol purple indicator[17] after 72 h of differing N treatments. Overexpressing line b-S6 showed alkalinization in nitrate and acidification in ammonium relative to WT, while the pH in hydroponic medium did not show a significant difference between WT and b-S6 over the same time scale (FIG. 18c) as the bulk solution was large enough to buffer any pH changes occurring at the root surface.

Figure 19:
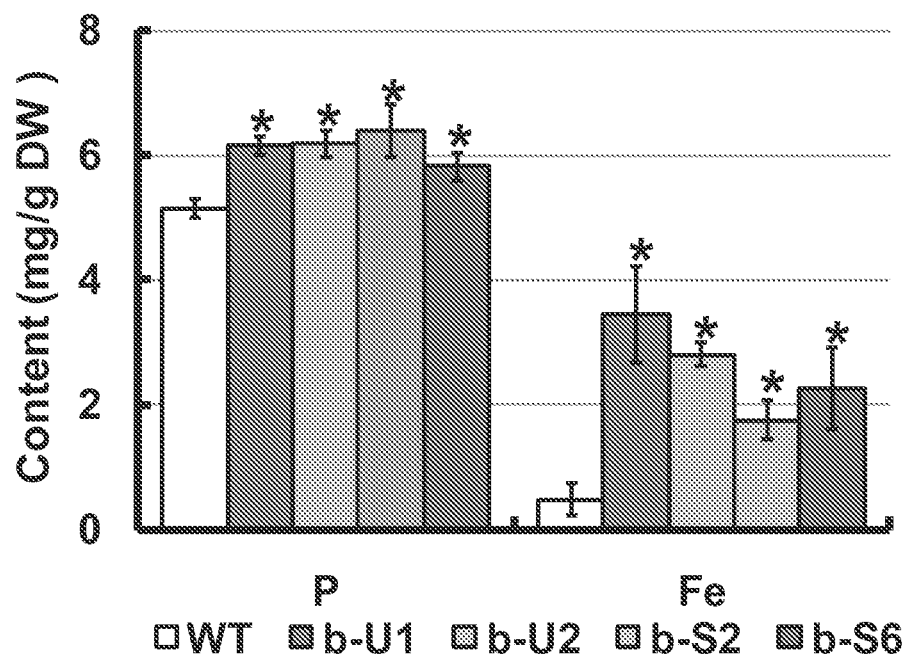
FIG. 19. The total leaf P and Fe in T2 Nipponbare rice over-expressing OsNRT2.3b growing in 1.25 mM $NH_4NO_3$ hydroponic culture. The total P and Fe was measured by ICP analysis. The 0.05 g dried crushed plant material powder was digested with 5 ml of 98% $H_2SO_4$ and 3 ml of 30% hydrogen peroxide. After cooling, the digested sample was diluted to 100 ml with distilled water. The ion concentrations in the solution were measured using the ICP-OES (Perkin Elmer Optima 2000 DV). Values are mean±S.E (n=4), * indicates significance of difference between WT and over-expression plants at 5% levels with One-way ANOVA analysis. Bars from left to right: WT, b-U1, b-U2, b-S2, b-S6.

The N supply form for plants is well known for influencing plant pH balance[24]. The assimilation of ammonium produces at least one $H^+$ per $NH_4^+$; while $NO_3^-$ assimilation produces almost one $OH^-$ per $NO_3^{-4}$. Either $H^+$ or $OH^-$ produced in excess of that required to maintain cytoplasmic pH are exported from the cell in an energy requiring step (e.g. plasma membrane $H^+$ pumping ATPase)[4,10]. Applicants compared the pH of phloem sap from N-starved rice plants resupplied with nitrate or ammonium. Nitrate and ammonium supply acidified the phloem pH of WT and transgenic plants (FIG. 3d, e). Interestingly, the phloem acidification was significantly lower in the four transgenic lines when compared with WT (FIG. 3d, e) although no significant difference in nitrate concentration could be detected in phloem (data not shown). These data show that transgenic plants are better able to regulate phloem pH. Furthermore the phloem pH difference between WT and transgenics (FIG. 17a, b) could explain the enhanced P and Fe accumulation in leaves of the OsNRT2.3b over-expressing plants (FIG. 19). The more acidic phloem sap (FIG. 17) will benefit P and Fe translocation to the leaf[25]. Together with enhanced N acquisition this was also an important factor for the plant growth and yield increase.

It has been reported that cytosolic pH acidification inactivated transport of aquaporin in oocytes[26]. Furthermore as nitrate assimilation depends on photorespiration[27], the relationship[4,28] between the assimilation of nitrate, ammonium and photorespiration is closely coupled to the shuttling of malate between the cytoplasm and chloroplast to balance pH[29].

In plants, the regulation of pH is a requirement that arises for a variety of reasons. The most basic reason is that water spontaneously ionizes with the consequence that protons cannot be removed entirely from a given solution. Unlike other ions, protons can be consumed or are produced in certain chemical reactions, with the result that the kind of nutrition determines to what extent protons may become a problem, or even a hazard, to the organism. The exact regulatory determinants and causalities are difficult to analyse (at a given moment) for any situation because pH influences a great variety of processes in a plant tissues and cells and intracellular compartments, and at the same time H+ activity may be changed by the same processes. The ability to reverse a pH perturbation, as well as the extent and the velocity at which this is accomplished, defines the quality of pH regulation.

The homeostatic maintenance of cytoplasmic pH is important for energizing the cellular uptake and storage of nutrients and secondary metabolites because proton-coupled transport systems mediate these cellular processes. The pH gradients between cellular compartments and the external environment provide an energy source for these important processes. Many key cellular processes are therefore enhanced by the improved pH homeostasis associated with a mixed nitrate and ammonium nitrogen supply.

Applicants have shown that the OsNRT2.3b may comprise a pH sensing motif on the cytosolic side of the plasma membrane which is not present in OsNRT2.3a on the cytosolic side. The pH-sensing motif VYEAIHKI (SEQ ID No. 16) around histidine residue 167 of OsNRT2.3b which faces the cytosolic side of the plasma membrane is a characteristic of the anion exchanger family, which is found in many different organisms including mammals and may therefore be of more general biological significance. As demonstrated in the examples, Applicants have shown that after a single amino acid mutation (H167R), OsNRT2.3b lost this function of cytosolic pH regulation, even after repeated cycles of nitrate treatment (FIG. 5b).

The OsNRT2.3b sensing motif regulates the cytosolic pH in the plant.

Applicants have also shown that the pH sensing motif of OsNRT2.3b is important for these effects in rice by linking the plant's pH status to nitrate supply.

In yet another aspect, the invention therefore relates to a method for regulating pH homeostasis which may comprise introducing and expressing a nucleic acid construct which may comprise a nucleic acid sequence which may comprise SEQ ID No. 1 operably linked to a regulatory sequence in a plant. In one aspect, the plant is not rice.

In a further aspect, the invention relates to a method for reducing acidification in a plant which may comprise introducing and expressing a nucleic acid construct which may comprise a nucleic acid sequence which may comprise SEQ ID No. 1 operably linked to a regulatory sequence in a plant. In one aspect, the plant is not rice.

Acidification may be reduced by at least about 0.1 pH units, for example 0.1, 0.2. 0.3, 0.4, 0.5, 0.6, 0.7, 0.8 or more.

In a further aspect, the invention relates to a method for altering nitrate transport and pH homeostasis in a plant which may comprise introducing and expressing a nucleic acid construct which may comprise a nucleic acid sequence which may comprise SEQ ID No. 1 operably linked to a regulatory sequence in a plant wherein said nucleic acid may comprise a mutation in the pH sensing motif VYEAIHKI (SEQ ID No. 16). The mutation renders the pH sensing motif non-functional.

As set out elsewhere herein, the regulatory sequence may be a constitutive promoter as described herein or a tissue specific promoter. In one embodiment, the promoter is a phloem specific promoter as described herein.

The term plant is also defined elsewhere herein. Preferably, the plant is a crop plant. Most preferred plants are maize, rice, wheat, oilseed rape, sorghum, soybean, potato, tomato, grape, barley, pea, bean, field bean, lettuce, cotton, sugar cane, sugar beet, tobacco, broccoli or other vegetable brassicas or poplar. In one embodiment, the plant is not rice.

The invention also relates to the use of a nucleic acid which may comprise SEQ ID No. 1, a functional variant, part or homolog thereof encoding SEQ ID No 3, a functional variant, part or homolog thereof which may comprise the pH sensing motif VYEAIHKI (SEQ ID No. 16) in regulating pH in a transgenic plant.

In another aspect, the invention relates to a method for increasing growth of a plant which may comprise introducing and expressing a nucleic acid construct which may comprise a nucleic acid sequence as defined in SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

In another aspect, the invention relates to a method for increasing nitrogen use efficiency of a plant which may comprise introducing and expressing a nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

In another aspect, the invention relates to a method for improving yield of a plant which may comprise introducing and expressing a nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

In another aspect, the invention relates to a method for increasing nitrate transport in a plant which may comprise introducing and expressing a nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

In another aspect, the invention relates to a method for increasing nitrogen acquisition of a plant which may comprise introducing and expressing a nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

In one embodiment of the various methods described herein for increasing NUE, growth, yield, nitrogen acquisition and/or nitrate transport, said traits are increased under stress conditions, for example nitrogen stress.

Thus, in another aspect, the invention relates to a method for conferring tolerance to nitrogen stress to a plant which may comprise introducing and expressing nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2.

Thus, in another aspect, the invention relates to a method for conferring pathogen resistance to a plant which may comprise introducing and expressing nucleic acid construct which may comprise a nucleic acid sequence which may comprise SEQ ID No. 1 operably linked to a regulatory sequence into a plant wherein said regulatory sequence is a constitutive promoter or a phloem specific promoter and wherein said plant does not overexpress a nucleic acid sequence which may comprise SEQ ID No. 2. If the plant is rice, then the pathogen may be *Fusarium* wilt, Leaf blight and Stripe rust.

According to the methods above, the regulatory sequence according to the method and plants above is as described herein and may therefore be a constitutive promoter as described herein, an inducible promoter or a tissue specific promoter. In one embodiment, the promoter is a phloem specific promoter as described herein. Phloem-specific expression may be important for the function of the OsNRT2.3b, as the vascular tissue is important for pH regulation and it has recently been shown that nitrate transport in the phloem occurs in plants and may be a significant route for nitrogen delivery to the shoot.

The term plant is also defined elsewhere herein. Preferably, the plant is a crop plant. Most preferred plants are maize, rice, wheat, oilseed rape, sorghum, soybean, potato, tomato, grape, barley, pea, bean, field bean, lettuce, cotton, sugar cane, sugar beet, broccoli or other vegetable brassicas or poplar. In one embodiment, the plant is not rice.

In another aspect, the invention relates to a method for increasing nitrogen use, yield, NUE, nitrogen efficiency, tolerance to nitrogen stress, pathogen resistance, nitrogen acquisition and/or nitrate transport of a plant which may comprise introducing and expressing nucleic acid construct which may comprise a nucleic acid sequence which may comprise SEQ ID No. 1 operably linked to a phloem specific promoter in a plant. The term plant is also defined elsewhere herein. Preferably, the plant is a crop plant. Most preferred plants are maize, rice, wheat, oilseed rape, sorghum, soybean, potato, tomato, grape, barley, pea, bean, field bean, lettuce, cotton, sugar cane, sugar beet, broccoli or other vegetable brassicas or poplar. In one embodiment, the plant is not rice.

In another aspect, the invention relates to a method for making a transgenic plant having increased yield, growth and/or nitrogen use efficiency which may comprise introducing and expressing in a plant or plant cell a nucleic acid construct which may comprise a nucleic acid sequence as defined in SEQ ID No. 1 operably linked to a regulatory sequence wherein said regulatory sequence is a constitutive promoter or a phloem specific promoter and wherein said plant does not overexpress a nucleic acid sequence which may comprise SEQ ID No. 2.

The method further may comprise regenerating a transgenic plant from the plant or plant cell after step a) wherein the transgenic plant may comprise in its genome SEQ ID No. 1 operably linked to a regulatory sequence and obtaining a progeny plant derived from the transgenic plant wherein said progeny plant exhibits increased yield, growth and/or nitrogen use efficiency. These methods are carried out as described elsewhere herein.

Plants or parts thereof obtained or obtainable by the method for making a transgenic plant as described above are also within the scope of the invention.

In another aspect, the invention relates to a transgenic plant expressing a nucleic acid construct which may comprise a nucleic acid sequence as defined in SEQ ID No. 1 operably linked to a regulatory sequence into a plant wherein said regulatory sequence is a constitutive promoter or a phloem specific promoter and wherein said plant does not overexpress a nucleic acid sequence SEQ ID No. 2.

Plants that can be used according to these methods of the invention are specifically listed elsewhere herein but also include rice. Preferably, the plant is a crop plant or biofuel plant as defined elsewhere herein.

Most preferred plants are rice, maize, wheat, oilseed rape, sorghum, soybean, potato, tomato, tobacco, grape, barley, pea, bean, field bean, lettuce, cotton, sugar cane, sugar beet, broccoli or other vegetable brassicas or poplar.

In one embodiment, the plant is wheat and the promoter is a phloem specific promoter as described herein. In one embodiment, the plant is tobacco and the promoter is a phloem specific promoter as described herein.

The plant is characterised in that it shows having increased yield, growth, nitrogen transport, nitrogen acquisition, nitrogen stress tolerance and/or nitrogen use efficiency.

Other objects and advantages of this invention will be appreciated from a review of the complete disclosure provided herein and the appended claims.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure. The specifics of these examples should not be treated as limiting.

All documents mentioned in this specification, including references to databases for gene or protein sequences, are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The invention is further described in the following non-limiting examples
1. Expression of OsNRT2.3a and OsNRT2.3b in Rice
Materials and Methods
Over-expression Vector Construction and Transgenic Plants The open reading frames of OsNRT2.3a and OsNRT2.3b were amplified by gene specific primers. The fragment was treated with restriction enzymes and inserted in vectors and sequenced before transformation. Rice (*Oryza sativa*) embryonic calli were transformed using *Agrobacterium*-mediated methods[33]. One copy insertion T0 plants were harvested and grown to generate T1 plants. Homozygous T1 plants were taken for T2 generation. Two lines of T2 OsNRT2.3a over-expression plants, a-U1 and a-U2 and four lines of T2 OsNRT2.3b over-expression plants, b-U1, b-U2, b-S2 and b-S6 were used for further experiments. T2 field experiments were conducted in Changxing experiment station of Zhejiang University (May-October 2010) in four N application N as urea levels as 0, 75, 150 and 300 kg N/ha. Seeds were germinated on 5th May and seedlings of each type were planted at 3 rows and 33 plants with 25 cm (row space)×20 cm (plant space) on 5th June. Plants were grown in blocks (FIG. 23*a,b*) with a random order for each N application. For the large scale experiments at 75 kg N/ha, the plants were transplanted as 10 rows×128 plants (FIG. 23*d*). Three replications were used for all field experiments and the plots were finally harvested on the 10th October. The soil nutrient status in this experiment station was total nitrogen (N): 1.00±0.18 mg/g, total phosphorus (P) 0.38±0.08 mg/g, total potassium (K) 39±2.3 mg/g, Olsen P (0.5 mM NaHCO$_3$-extractable P) 23±4.1 mg/kg and soil pH was 6.3±0.47 (n=6). 60 kg P (as Ca(H$_2$PO$_4$)$_2$)/ha and 110 kg K (as K$_2$SO$_4$)/ha fertilizer was applied to the paddy before transferring the rice seedlings. The first N application was carried out before transferring on 3th June and 20% total N fertilizer was mixed into soil. Second application was 40% on 12 June when the rice was at the beginning of tilling stage. The final application was 40% on 20 June. The rice growth period at Changxing was 120 ±3 days for WT, a-U1 and a-U2 lines, and 130±2 days at 0-75 kg N/ha level, 135±2 days at 150 kg N/ha level and 140±2 days at 300 kg N/ha level for b-U1, b-U2, b-S2 and b-S6 lines. The grain yield was measured at harvest and NUE was defined as grain yield per fertilizer N applied. For the $^{15}$N uptake, xylem and phloem sap collection experiments, hydroponic growth conditions were used as described previously[34] in IRRI culture medium at pH 5.5 with 1.25 mM NH$_4$NO$_3$ as the N supply unless stated otherwise. Roots RNA was abstracted for RT-PCR analysis.

Antibody Production and Western Blot

The full cDNA sequences of OsNRT2.3a/b genes were amplified from plasmids of OsNRT2.3a (AK109776) and OsNRT2.3b (AK072215) by primers, F: GGAATTCTCA-CACCCCGGCCGG (SEQ ID No. 17), R: CGGGATCC-ATGTGGGGCGGCATGCTC (SEQ ID No. 18). The plasmids were kindly provided by Dr. Kikuchi (KOME). The PCR fragment was sub-cloned into the bacterial expression vector pGSX (Amersham) at BamH I and EcoR I sites. The amino acid products were purified and their monoclonal-antibodies were synthesized[35]. The monoclonal-antibody was selected from 192 individual cell specific reactions to OsNRT2.3a (516 aa) or OsNRT2.3b (486 aa) protein. Plasma membrane protein abstraction from roots and western blot was done as previously described[10,14] and repeated twice.

RNA In Situ Hybridization

RNA in situ hybridization was performed as previously described[36]. For OsNRT2.3b probe, the binding site is in OsNRT2.3b specific 5' UTR with its sequence CGATGGT-TGGGTGCGGCGAGA (SEQ ID No. 19). The nonsense sequence is GCTACCAACCCACGCCGCTCT (SEQ ID No. 20). All probes were labeled at 5' end with DIG.

Determination of Root $^{15}$N Accumulation

Rice seedlings of WT and over-expression plants were grown in IRRI nutrient solution containing 1.25 mM NH$_4$NO$_3$ for two months in greenhouse and then deprived of N for 3 days. The plants were rinsed in 0.1 mM CaSO$_4$ for 1 min, then transferred to the solution containing either 1.25 mM Ca($^{15}$NO$_3$)$_2$ (atom % $^{15}$N: 99.27%) or ($^{15}$NH$_4$)$_2$SO$_4$ (atom % $^{15}$N: 95.7%) or $^{15}$NH$_4$NO$_3$ (atom % $^{15}$N: 45%) or NH$_4$$^{15}$NO$_3$ (atom % $^{15}$N: 45.25%) or $^{15}$NH$_4$$^{15}$NO$_3$ (atom % $^{15}$N: 95.5%) for 5 min and finally rinsed again in 0.1 mM CaSO$_4$ for 1 min. Roots were separated from the shoots immediately after the final transfer to CaSO$_4$, and frozen in liquid N. After grounding, an aliquot of the powder was dried to a constant weight at 70° C. 10 mg powder of each sample was analyzed using the MAT253-Flash EA1112-MS system (Thermo Fisher Scientific, Inc., USA). The whole experiment was repeated twice and each time with five replicates.

Xylem and Phloem Sap Collection

Rice seedlings were grown in 1.25 mM NH$_4$NO$_3$ for 8 weeks and then transferred to N treatments (nitrate: 1.25 mM Ca(NO$_3$)$_2$; ammonium: 1.25 mM (NH$_4$)$_2$SO$_4$) for 24 h and then cut at 4 cm above root. The below in N solutions was for xylem sap collection[34] and the top was for phloem sap collection[16].

For phloem sap collection, briefly each shoot was put into a 50 ml glass tubes with 15 ml 25 mM EDTA-Na$_2$ covered with Parafilm. The shoot was inserted through the Parafilm and phloem sap was collected for 24 h. Phloem pH changes were measured using a pH meter (model 868, Thermo Orion, USA) and by calculation of the pH difference in samples at the start and end of the phloem sap collection period. The experiment was conducted with 5 replicate samples and was repeated twice.

Phloem sap was also collected using an insect feeding method with the same plants as above. Each plant was set in a 250 ml bottle of IRRI nutrient solution with six plants kept in the insect cage at 26 C and a 16 h light period. Seven to ten adult brown plant hopper adults were transferred on to each plant at the beginning of the N treatments. Rice phloem honey dew secreted by the insects was collected at 24 h, 48 h duration of N treatments (FIG. 17).

Oocyte Preparation, mRNA Injection, $^{15}$N Uptake and Electrophysiology

Oocytes preparation, mRNA injection, $^{15}$N-nitrate uptake and electrophysiology have been described previously[37-39]. 0.5 mM Na$^{15}$N—NO$_3$ or $^{15}$N—NH$_4$Cl in ND96 was used for $^{15}$N selective uptake experiment for 16 h[38]. The pH selective microelectrode method was used to measure cytosolic pH[18].

Single Site Mutation of OsNRT2.3b and mRNA Synthesis

A point mutation (H167R) of OsNRT2.3b was generated using a PCR method. The point mutant was processed by PCR two fragments of OsNRT2.3b with the mutant site and new restriction site in the primers. OsNRT2.3b cDNA in pT7Ts was used as a DNA template and the first PCR fragment (H167RB) was sub-cloned into HindIII and XbaI of pT7Ts. New plasmid and second PCR fragment (H167R) were digested by Csp45 I and Xba I and ligated into the final plasmid with H167R site mutated OsNRT2.3b cDNA (pH167R). The mRNA synthesis of pH167R was described as above.

RNA Preparation and DNA Microarray Hybridization

Three replicates each of WT (Nipponbare), a-U1 and b-S6 shoots were harvested from 150 Kg N/ha treatment in field of Changxing experiment station at 10:00 am of the 1th August i.e. the maximum tillering stage for all plants. Shoot tissues samples taken for RNA extraction were flash frozen at −80° C. in liquid nitrogen immediately on harvesting. RNA extraction, hybridization with Affymetrix rice GeneChip arrays (Santa Clara, Calif., USA), data analyses and annotation were as described in previous reports[40].

Quantitative Real-time RT-PCR

Total RNA from three biological representatives, specifically from the roots and shoots of WT and transgenic plants, was isolated using the TRIzol reagent according to the manufacturer's instructions (Invitrogen Life Technologies, Carlsbad, Calif., USA)[13].

Gas Exchange and Postillumination CO$_2$ Burst Measurements

The rate of light-saturated photosynthesis of flag leaves was measured from 9:00 h to 15:00 h using a Li-Cor 6400 portable photosynthesis open system at the plants in 150 Kg N/ha treatment in field of Changxing experiment on the same day as microarray sampling. Leaf temperature during measurements was maintained at 27.0±0.1° C. with a photosynthetic photon flux intensity (PPFD) of 1500 μmol photons m$^{-2}$·s$^{-1}$ as described before[41]. The ambient CO$_2$ concentration in the cuvette (Ca-c) was adjusted as atmospheric CO$_2$ concentration (Ca) (417±1.0 μmol CO$_2$ mol$^{-1}$), and the relative humidity was maintained at 20%. Data were recorded after equilibration to a steady state (10 min). The measured leaves were labelled, and leaf areas were calculated based on the labelled area. The postillumination CO$_2$ burst (PIB) was measured at the same labelled leaf under photorespiratory conditions (saturating PPFD of 1,500 μmol photons m$^{-2}$·s$^{-1}$, Ca-c CO$_2$ concentration of 100 μmol CO$_2$ mol$^{-1}$, relative humidity of 60%-70%) as described before[22].

Results

Over-expression of OsNRT2.3b Increased Rice Growth

Figure 1D:
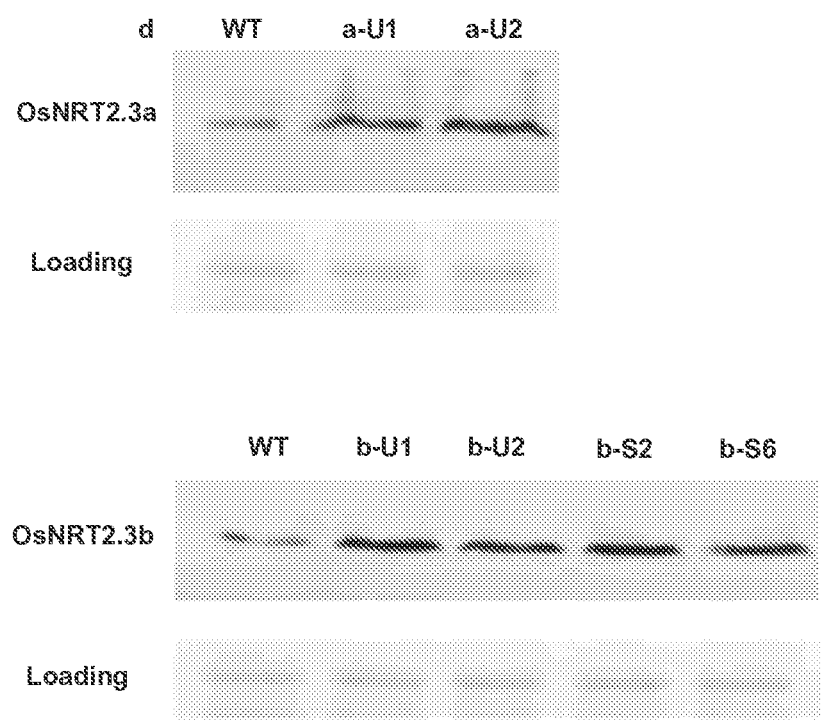
Figure 1E:
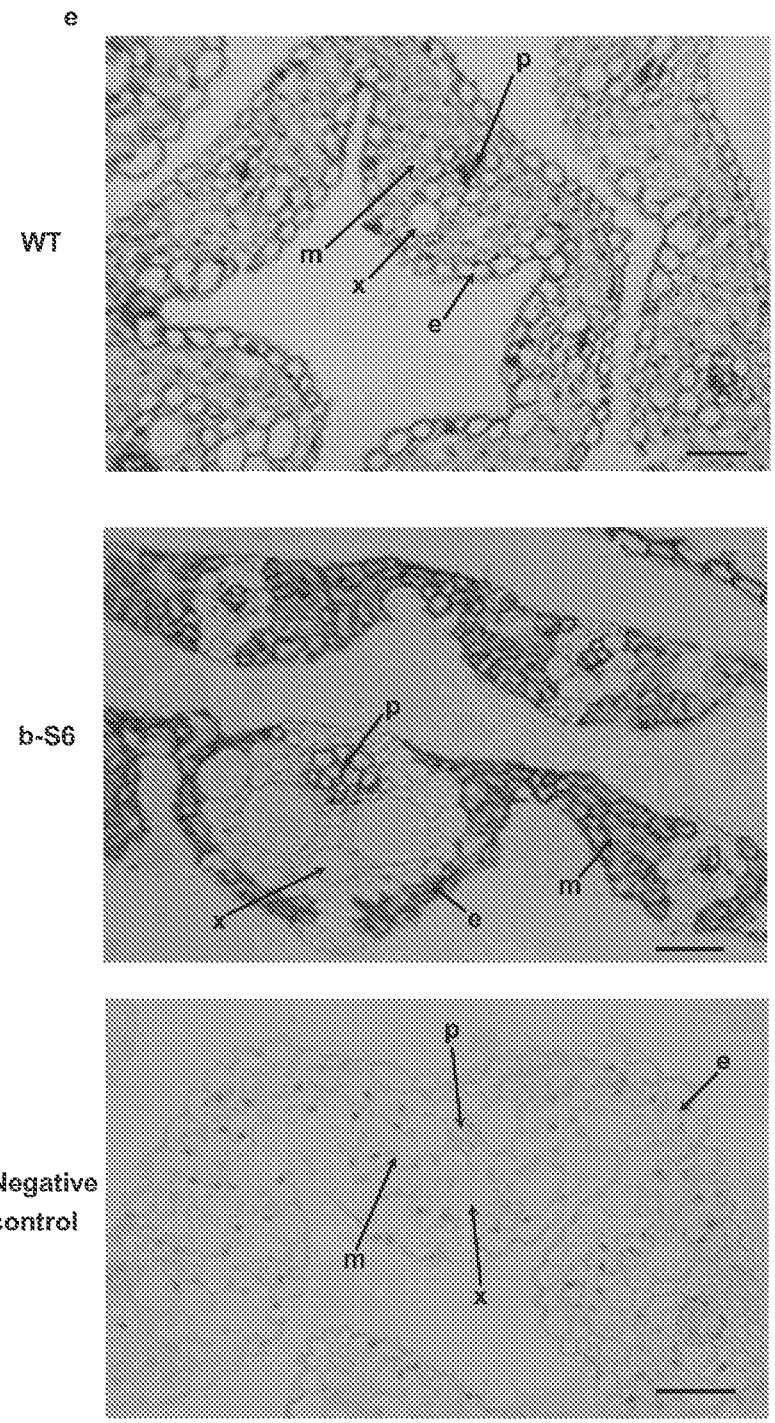

Applicants generated rice (*Oryza sativa* L ssp. *Japonica*, cv. Nipponbare) plants that over-express OsNRT2.3a and OsNRT2.3b by *Agrobacterium*-mediated transformation, using either ubiquitin or 35S promoters (FIG. 1a, b). The over-expression lines were named a-U1 and a-U2 for OsNRT2.3a, b-U1, b-U2, b-S2 and b-S6 for OsNRT2.3b, respectively with one copy insertion. Interestingly, the OsNRT2.3b over-expression lines, which were confirmed at both transcript and protein levels (FIG. 1cd), showed more growth compared with wild type (WT) (FIG. 1a, b). The biomass and panicle size of over-expression lines was greater than WT (FIG. 11; Table 2-3). The primary and second rachis size was increased therefore the total number of seeds per panicle was greater than WT (FIG. 11, Table 2). By contrast, the OsNRT2.3a over-expression plants did not show visible difference from WT even though OsNRT2.3a mRNA and protein was increased in the transformed lines (FIG. 1c, d, FIG. 11). The in situ hybridization results showed that OsNRT2.3b mRNA in b-S6 leaf was over-expressed in the epidermal, phloem and mesophyll cells when compared with wild type (FIG. 1e). Furthermore, when OsNRT2.3b was over-expressed in other high yielding and high NUE rice cultivars, WYJ7 from southern China and YF47 from northern China, their grain yield and NUE (grain yield divided by the N fertilizer applied) were also significantly increased (FIGS. 12, 13).

Field Trials of Over-expression Lines Show Increased Grain Yield and NUE in both Subtropical and Tropical Climates at a Range of N Fertilization Rates Encouraged by the strong phenotypes of the OsNRT2.3b over-expressing plants in hydroponics and soil pots, Applicants grew selected Nipponbare, WYJ7 and YF47 transgenic lines and their wild types in 4 field trials to evaluate their performance under different fertilizer N rates.

Figure 2A:
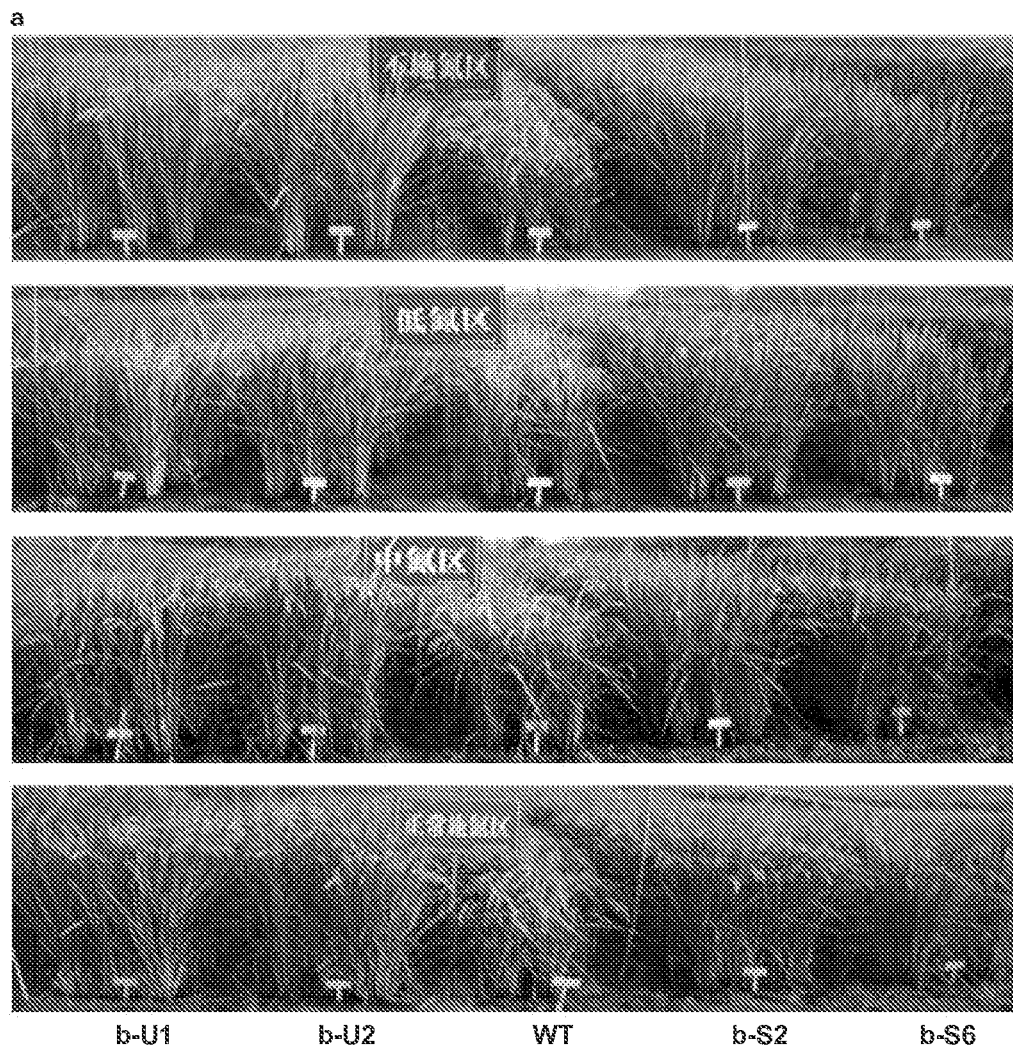

Four Nipponbare T2 transgenic lines and WT were grown with four levels of N fertilizer application in a paddy field (soil pH 6.3) located at Changxing in the subtropical climate region (FIG. 2). Compared with WT, biomass, seed numbers per panicle, ripening rate, grain yield and NUE of the transgenic lines were significantly increased at all levels of N application (FIG. 2a-c, Table 5). The average increase in grain yield ranged from 33% at 75 kg N/ha to 25% at 300 kg N/ha. The grain yield of the over-expression lines supplied with 150 kg N/ha was 6% to 13% higher than that of WT yield fertilized with 300 kg N/ha (FIG. 2b). Remarkably the best performing transgenic line, b-S6 produced similar grain yield at 75 kg N/ha to WT at 300 kg N/ha (FIG. 2b, Table 5). The NUE of the OsNRT2.3b over-expressing lines reached 68-79 g/g N at the 75 kg N/ha application level, compared with 55 g/g N in WT (FIG. 2c). In a large scale field experiment supplied with 75 kg N/ha, the yield and NUE of the line b-U2 were 30.5% more than WT; while for line b-S6 the values were even greater at 40.5% (FIGS. 2d,e,f).

Figure 14B:
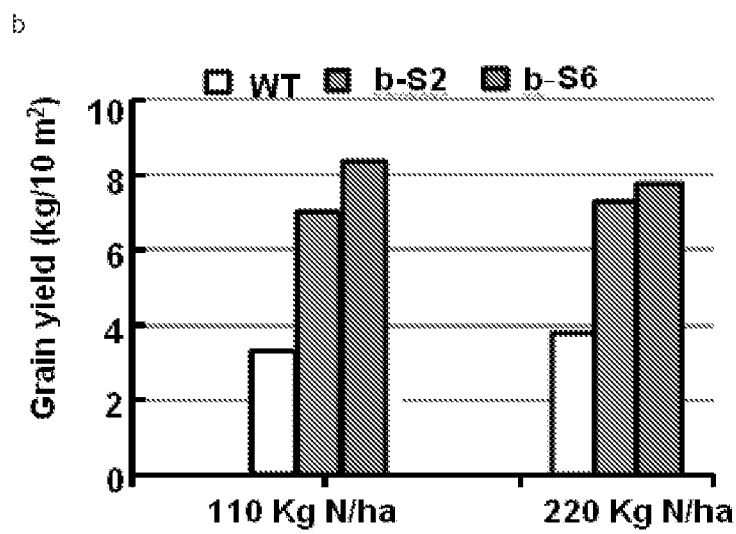

In a second field trial, the T5 generations of b-S2 and b-S6 were grown in tropical Hainan (FIG. 14a). Significant increases in grain yield and NUE were again obtained. The largest difference between the transgenic lines and Nipponbare WT was found in the 110 kg N/ha supply (FIG. 14b). Furthermore, crossing b-S6 T5 plants with WT confirmed that the b-S6 phenotype was completely contributed by OsNRT2.3b over-expression as in F2 generation plants the aa genotype returned to WT and AA genotype was like b-S6 (FIG. 15).

The third field trial tested the OsNRT2.3b over-expressing lines in the WYJ7 background with three N supplies (110 and 220 kg N/ha) in Changxing. Among the four transformed lines (T2 generation), grain yield was 35-51% larger than WT at 110 kg N/ha and 38-42% larger at 220 kg N/ha. On average, the NUE was 43% higher than WT (FIG. 12f).

Figure 15:
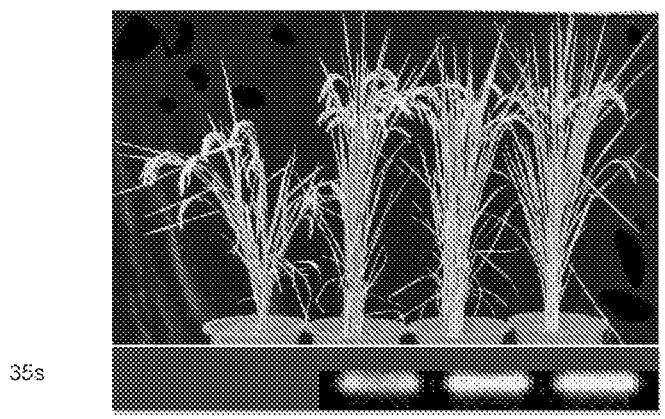
FIG. 15. The F2 generation phenotype of Nipponbare (♀)×b-S6 T5(♂).

The fourth field trial tested the OsNRT2.3b over-expressing lines in the YF47 cultivar background in Hainan (FIG. 15). Similar to the results obtained with the other two backgrounds, OsNRT2.3b over-expression in YF47 generated more biomass and 39% more grain yield than WT at a usual N fertilizer supply (150 kg/ha) (FIG. 13a, d). Taken together, OsNRT2.3b over-expression produced consistent effects on grain yield and NUE across different cultivar backgrounds, climates, and N application rates.

In the Nipponbare background, OsNRT2.3b over-expression resulted in a delay in flowering compared with WT, by 15±2 days at 150 kg/ha and 20±2 days at 300 kg/ha (FIGS. 2a,d, FIG. 16, Table 1). In pot experiments with these plants, at 120 days after germination the grain yield of b-S2 and b-S6 was 37% and 40% higher than WT (FIG. 16g). At 140 days the grain yield of b-S2 and b-S6 was 55% and 49% higher than WT (FIG. 16g). The extra 20 days increased their yield by only 18% and 9% compared with the data at the first 120 days. It was clear that the greatest contribution of OsNRT2.3b over-expression to grain yield occurred at 120 days. Furthermore the 20 days growth delay did not significantly increase the total N uptake for OsNRT2.3b over-expression plants (FIG. 16h). However 20 days delay increased the ratio of biomass and N transfer to the grain (Tables 3-4) and the N utilization (assimilation) efficiency (NUtE) from 33 g-grains/g-N at 120 days (no significant difference from WT) to 39.1-40.2 g-grains/g-N at 140 days (a significant increase relative to WT for b-S2 and b-S6 (FIG. 16i). In fact relative to WT there was no flowering delay of OsNRT2.3b over-expressers in WYJ7 and YF47 background.

OsNRT2.3b Over-expression Increased Nitrate Influx, Transport to Shoot, Xylem pH, Phloem pH Homeostasis, P and Fe Accumulation in Leaves.

Applicants measured the effect of OsNRT2.3b over-expression on $^{15}$N-nitrate influx in four Nipponbare transformed lines hydroponically grown at pH 6 (FIG. 3a). The nitrate influx rate was increased significantly in all the transgenic lines compared with WT (FIG. 3a), demonstrating increased activities of OsNRT2.3b in these plants. By contrast, OsNRT2.3b over-expression had no significant effect on the short-term $^{15}$N-ammonium uptake (FIG. 3a).

More nitrate and less ammonium were detected in the xylem of b-U1, b-U2, b-S2 and b-S6 in compared with WT under nitrate supply (FIG. 3b). Xylem pH was 7 and 7.3 in WT treated respectively with nitrate and ammonium, while it was 7.5 and 7.6-7.8 in the OsNRT2.3b over-expressing lines, significantly higher than WT. After 24 h N treatments, phloem sap was collected. The phloem sap pH was measured using the EDTA-Na$_2$ collection method[16] and less acidification was found in OsNRT2.3b over-expression lines. The difference between WT and over-expression lines was about 0.2 pH units in nitrate and about 0.1 pH units in ammonium. To check the phloem pH using a different method, the sap was collected from phloem-feeding insects (described in FIG. 9). WT phloem pH decreased from 7.8 to 6.1 and b-S6 from 6.7 to 6.0 in nitrate supply from 24 to 48 h treatments (FIG. 9a); while in ammonium treatment WT phloem pH decreased from 7.4 to 6.3 and b-S6 from 6.6 to 5.9 from 24 to 48 h (FIG. 9b). The difference between WT and b-S6 under nitrate supply was remarkably high at 24 h, however no significant difference was found by 48 h. In ammonium supply, although the pH in WT sap was higher than in b-S6 the difference was not significant (FIG. 9b). The acidification of WT phloem pH in nitrate was about 1.7 pH units however it was only 0.7 of a pH unit in the b-S6 plants (FIG. 3e). By 48 h the collected phloem pH sap had adjusted to give more similar values for WT and b-S6 plants (FIG. 9b). Furthermore the root apoplastic pH in WT and b-S6 roots was tested with bromocresol purple indicator[17] after 72 h of differing N treatments. Overexpressing line b-S6 showed alkalinization in nitrate and acidification in ammonium relative to WT (FIG. 18a, b), while the pH in hydroponic medium did not show a significant difference between WT and b-S6 over the same time scale (FIG. 18c) as the bulk solution was large enough to buffer any pH changes occurring at the root surface.

Under ammonium nitrate supply the total P and Fe in the plants were also measured. Both total P and Fe were increased in the leaves of the over-expressing lines compared with WT (FIG. 19), especially for total Fe, it was 3-6 times more than WT.

OsNRT2.3b Over-expression Increased Total N Uptake in Mixture Supply of Ammonium and Nitrate at pH 4 and 6.

N-starved plants were resupplied with NH$_4$$^{15}$NO$_3$ or $^{15}$NH$_4$NO$_3$ or $^{15}$NH$_4$$^{15}$NO$_3$ in pH 4, and 6 for 5 min to measure N uptake by root (FIG. 4). These results clearly showed as the pH increased, the $^{15}$NO$_3$$^-$ influx was decreased, $^{15}$NH$_4$$^+$ and total $^{15}$N was increased dramatically for both WT and all the OsNRT2.3b transgenic lines (comparing FIGS. 4a, b, c). The OsNRT2.3b over-expression lines showed more $^{15}$NH$_4$NO$_3$ and total N uptake at pH 4 and 6. In the field experiments, soil pH ranged from 4.4 to 6.4 (FIGS. 1, 2, 13-14), the phenotype of the field grown transgenic lines can be explained by the enhanced total N acquisition (nitrate and ammonium) of these plants.

Transport Function of OsNRT2.3b Regulated by Cytosolic pH

As over-expression of OsNRT2.3b has such a major impact on NUE and growth of rice and this effect was related to plant pH homeostasis, Applicants investigated the transporter function in more detail at the molecular level. In heterologous expression experiments the nitrate-elicited changes in membrane potential of *Xenopus* oocytes expressing OsNRT2.3b could not respond to sequential nitrate treatments (FIG. 5a). It was necessary for an oocyte to rest for at least 30 min between nitrate treatments to recover the electrical response or it could respond to nitrate immediately after washing with pH 8.0 saline (FIG. 5a). Double-barrelled pH electrode measurements showed that a 0.2 pH acidification of cytosolic pH prevented the second nitrate response of OsNRT2.3b injected oocytes (FIG. 5a). A slight delay of cytosolic pH response was observed compared with membrane potential shift to external nitrate treatment (FIG. 5a). This cytosolic pH delay from membrane potential response was presented by other authors[18,19].

The consensus transmembrane (TM) secondary structure of OsNRT2.3b was predicted using software packages. 14 software packages predicted that OsNRT2.3 has 11 TM with the N terminus on the cytosolic side and the first 5 TM are presented in table below. H 167 amino acid was predicted in the cytosolic side in both table and figure, which was shown with the single site mutagenesis target ringed in prediction secondary structure below, predicted by http://bioinfo.si.hirosaki-u.ac.jp/~ConPred2/.). The pH-sensing motif VYEAIHKI is around residue 167 on the cytosolic side.

Interestingly, bioinformatics analysis of the predicted OsNRT2.3b protein structure revealed a pH-sensing motif VYEAIHKI[20] around a histidine (H) residue of OsNRT2.3b which faces the cytosolic side of the plasma membrane After a single site mutation (H167R), OsNRT2.3b lost this function of cytosolic pH regulation, even after repeated cycles of nitrate treatment (FIG. 5b). The results show that endogenous oocyte cellular pH homeostatic mechanisms were able to restore cytosolic pH above the threshold for OsNRT2.3b transport activity. When oocytes were incubated in $^{15}$N-nitrate for only 4 hours, the regulatory effect of cytosolic pH on nitrate transport was clear, as the comparison of H167R and wild type forms of OsNRT2.3b showed that the mutation resulted in a much larger nitrate accumulation (FIG. 5c). However, after an 8 h incubation the differences in activity of the two forms of the transporter had disappeared; suggesting that after the longer incubation the accumulation of nitrate had reached a maximum in the oocytes.

Decreased Photorespiratory Gene Expression and Photorespiration

Some genes are known to be specifically associated with plant photorespiratory activity[21]. Microarray and confirmatory qPCRs showed a gene expression pattern that indicates that photorespiration was altered in rice over-expressing OsNRT2.3b, when compared with WT and lines with increased OsNRT2.3a transcripts.

The total photosynthesis in b-S2 and b-S6 increased compared with WT, but b-U1 and b-U2 did not significantly increase. However intercellular $CO_2$ concentration was increased and the photorespiratory rate was decreased in all over-expression lines compared with WT (FIG. 20). The reduced photorespiration and enhanced photosynthesis in transgenic plants could contribute more biomass[22]. These data suggested that increased photosynthetic efficiency in plants overexpressing OsNRT2.3b contributes to the strong phenotype.

Discussion

The pH sensing activity switch of OsNRT2.3b is one of the key factors providing an explanation for the phenotype of the transgenic plants, since transforming OsNRT2.3b H167R mutant gene into Nipponbare plants did not increase height, yield and did not delay reproductive stage (FIG. 21). The pH-sensing motif VYEAIHKI (SEQ ID No. 16) around residue 167 is a characteristic of the anion exchanger family, which is found in many different organisms including mammals and may therefore be of more general biological significance[20]. Increasing the external pH decreased nitrate accumulation in the OsNRT2.3b expressing oocytes (FIG. 5d), supporting the idea that OsNRT2.3b is a proton-nitrate co-transporter[14]. Increasing the external pH decreases the proton gradient driving nitrate transport, but on the other hand it restores the nitrate transport function of OsNRT2.3b by making the cytosol more alkaline. Both effects occur via pH changes, but each happens on different sides of the plasma membrane. In planta the simultaneous influx of nitrate and ammonium counters the cytosolic pH regulatory effect of the OsNRT2.3b sensing motif. The proton-cotransport mechanism for the entry of nitrate into cells provides a cytosolic acidification, while ammonium transport can cause an alkalinization[23] that may enhances proton-coupled nitrate transport. This short-term synergism between ammonium and nitrate transport to maintain cytosolic pH can explain the measured increase in $^{15}$N-ammonium uptake when the plant was supplied with a mixed N source (FIG. 4), with the exclusion of the possibility that OsNRT2.3b protein itself might uptake ammonium in oocytes (FIG. 22). In WT plants, OsNRT2.3b expression was low[13] and mainly localized in the phloem of leaves but not roots (FIG. 1d). The transgenic plants with OsNRT2.3b over-expression driven by strong promoters had more general tissue expression (FIG. 1d). The synergism between ammonium and nitrate transport was enhanced by over-expression of the pH sensing transporter OsNRT2.3b more generally in root cells.

The N supply form for plants is well known for influencing plant pH balance[24]. The assimilation of ammonium produces at least one $H^+$ per $NH_4^+$; while $NO_3^-$ assimilation produces almost one $OH^-$ per $NO_3^{-4}$. Either $H^+$ or $OH^-$ produced in excess of that required to maintain cytoplasmic pH are exported from the cell in an energy requiring step (e.g. plasma membrane $H^+$ pumping ATPase)[4,10]. The vascular specific expression of OsNRT2.3b in WT plants suggests a possible specific role in long distance transport within plants. To test this idea Applicants compared the pH of phloem sap from N-starved rice plants resupplied with nitrate or ammonium. Nitrate and ammonium supply acidified the phloem pH of WT and transgenic plants (FIG. 3d, e). Interestingly, the phloem acidification was significantly lower in the four transgenic lines when compared with WT (FIG. 3d, e) although no significant difference in nitrate concentration could be detected in phloem (data not shown). These data show that transgenic plants are better able to regulate phloem pH, indicating that this is an important factor for the improved NUE. Furthermore the phloem pH difference between WT and transgenics (FIG. 17a, b) could explain the enhanced P and Fe accumulation in leaves of the OsNRT2.3b over-expressing plants (FIG. 19). The more acidic phloem sap (FIG. 17) will benefit P and Fe translocation to the leaf[25]. Together with enhanced N acquisition this was also an important factor for the plant growth and yield increase.

It has been reported that cytosolic pH acidification inactivated transport of aquaporin in oocytes[26]. As discussed by these and other authors[26], it suggested cytosolic pH could be a key regulation for both aquaporin and nitrate transporter in plants. Furthermore as nitrate assimilation depends on photorespiration[27], the relationship[4,28] between the assimilation of nitrate, ammonium and photorespiration is closely coupled to the shuttling of malate between the cytoplasm and chloroplast to balance pH[29].

Many important crop traits like NUE are well known to be complex multi-gene traits[4]. However, a few reports show that changing expression of a single trans-gene can significantly improve crop NUE[30-32]. The dramatic enhanced performance of the OsNRT2.3b transformed plants under different field conditions shows the prospects for improving rice NUE through single trans-gene approaches. The coupling of pH balance and NUE is likely to have more general relevance to crops and offers a promising way of improving NUE.

2. Expression of OsNRT2.3b in *Arabidopsis*

Figure 6C:
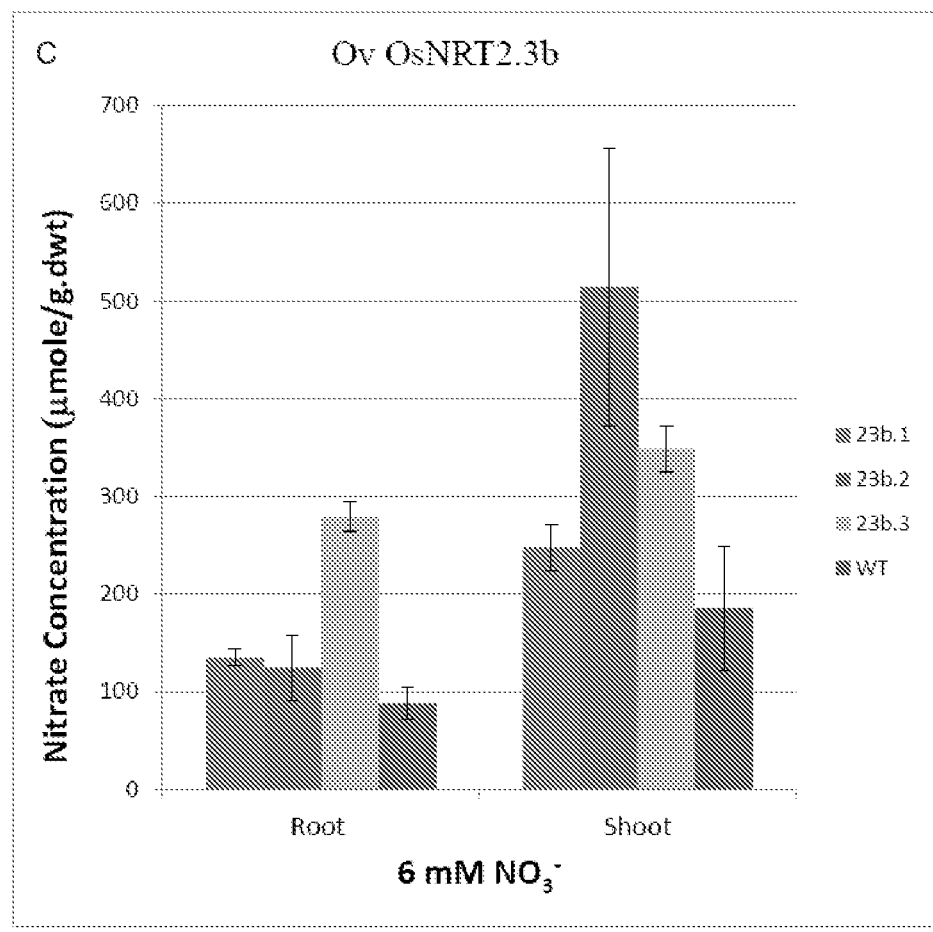

Applicants have obtained data with 35S-driven expression of OsNRT2.3b in *Arabidopsis*. The *Arabidopsis* plants were transformed using standard floral-dipping *Agrobacterium*-mediated transformation techniques (Clough & Bent 1998). In Petri dish growth experiments *Arabidopsis* plants were supplied with either 0.2 or 6 mM nitrate supplies. Three independent lines of *Arabidopsis* plants overexpressing the OsNRT2.3b (checked at the mRNA level, using RT-PCR) were tested and compared with wild type control plants (see FIG. 6). The data in FIG. 6 show that three independent *Arabidopsis* lines overexpressing the rice transporter growing on 6 mM nitrate had significantly more shoot biomass (Fig A) and had shorter roots on 0.2 mM supply (Fig B) relative to wild type plants. Furthermore, two of these lines accumulated more tissue nitrate.

These plants were grown a very simple culture system on agar Petri dishes with plant nutrients added to the agar (see Orsel et al. 2006 for details). Applicants will repeat these experiments in hydroponic culture and soil pots to determine and compare NUE between wild types and lines overexpressing OsNRT2.3b. $^{15}$N-enriched nitrate will be used in Petri dish and hydroponic experiments to measure and compare nitrate influx rates between wild types and overexpressing lines (see Orsel et al. 2006 for methods). Plants will be grown and compared in mixed nitrogen supplies, that include ammonium nitrate or nitrate as the only nitrogen source.

3. Expression of OsNRT2.3b in Tobacco

Method and Materials:

Over-expression Vector Construction and Transgenic Plants

The open reading frames of OsNRT2.3b were amplified by gene specific primers (Table 1). The fragment was treated with restriction enzymes, inserted into vectors and sequenced before transformation. *Nicotiana tabacum* cultivar 89 embryonic calli were transformed using *Agrobacterium*-mediated methods (Ai et al. 2009. One copy insertion T0 plants were harvested and grown to generate T1 plants (FIG. 1). Homozygous T1 plants were taken for T2 production.

Southern-Blot

The independent transgenic lines with gene knockdown of OsNRT2.3a, namely r1 and r2, were determined by Southern-blot analysis following the procedures described previously (Jia et al., 2011).

Semi-quantitative RT-PCR

Total RNA was isolated from 100 mg of plant material with Trizol reagent (Invitrogen, Carlsbad, Calif., USA). Total RNA concentrations were determined by UV spectrophotometry (Eppendorf, Biophotometer, Germany) 2 µg of total RNA from each sample was used as template for the first-strand cDNA synthesis, which was performed using M-MLV reverse transcriptase (Fermentas, Foster City, Calif., USA) according to the manufacturer's manual. The PCR amplification was performed using Taq DNA polymerase (Fermentas, Foster City, Calif., USA) for target genes with specific primers shown below.

4. Expression of OsNRT2.3b in Wheat

The phloem localised expression of NRT2.3b, and recent findings that significant amounts of nitrate are transported in the phloem e.g. Fan et al. 2009 (previously it was generally assumed that nitrate is transported from the root to the shoot in the xylem), together with the important role of the phloem in pH homeostasis suggest that phloem specific expression of OsNRT2.3b may be important for the results reported (e.g. improved NUE). For these reasons, Applicants used both ubiquitin and a phloem-specific promoters to drive expression of OsNRT2.3b in wheat. The ubiquitin promoter was used for the transformation as shown in FIGS. 27 and 28. The construction of 35S-OsNRT2.3b vector was described in rice transformation and wheat were produced by particle bombardment of calli cultured from immature embryos of susceptible variety Yangmai 158 as described (by Cao et al). The transgenic plant showed increased yield compared to wt plants, see FIGS. 27 and 28.

5. Pathogen Resistance of Transgenic Rice

Transgenic rice plants expressing OsNRT2.3b generated as described above were analysed in field trails in Hainan for pathogen resistance. The main rice diseases in Hainan, *Fusarium* wilt, Leaf blight and Stripe rust. For each plot, the survival rates were counted by the rice plants number at harvest/rice plants transferred at the beginning of January. Transgenic plants showed better survival rates compared to wt plants (FIG. 26).

The Primers Used for RT-PCR of OsNRT2.3b Gene

Genes Primers

```
OsNRT2.3b (AK072215)
F:
                                          (SEQ ID No. 21)
  5'-CGTTCGCCGTGTT-3'

R:
                                          (SEQ ID No. 22)
  5'-TCGAAGCGGTCGTAGAAG-3'

Actin
F:
                                          (SEQ ID No. 23)
  5'-TTATGGTTGGGATGGGACA-3'

R:
                                          (SEQ ID No. 24)
  5'-AGCACGGCTTGAATAGCG-3'
```

The Primers Used for Over-expression Constructs

| PROMOTER | VECTOR | PRIMERS | | ENZYMES |
|---|---|---|---|---|
| CaMV-35S | pCAMBIA1302 | F | atCCATGGAGATCTCAGGGCACAGCGGATG (SEQ ID No. 25) | Bgl II |
| | | R | atCCATGGAGATCT ACACCCCGGCCGG (SEQ ID No. 26) | Bgl II |
| Ubiquitin | pTCK303 | F | caACTAGTGCTACCACGTGTTGGAGATG (SEQ ID No. 27) | SpeI |
| | | R | GaACTAGTGAGCAAACCACCAACAAGC (SEQ ID No. 28) | SpeI |

The Primers Used for Subcloning of OsNRT2 Genes and OsNAR2 Genes into pT7Ts

| Gene | Clone vector | Subcloning primers | Plasmid linearization sites | Promoter for RNA synthesis |
|---|---|---|---|---|
| OsNRT2.3b (AK072215) | pLambda-FLC I | F: AATCAGATCTTTGGAGCTCCACC GC (SEQ ID No. 29) R: CAGAACTAGTCCCCCCCTCGAA GG (SEQ ID No. 30) | Xba I | T7 |

The Primers Used for H167R Site Mutant of OsNRT2.3b

| Mutation | Mutagenic primer | Codon change | New restriction site |
|---|---|---|---|
| H167R-F | GCCATT CGA AAGATCGGTAGCACGC (SEQ ID No. 31) (original sequence: GCCATC CAC AAGATC GGTAGCACGC)[a] (SEQ ID No. 32) | CAC(H)-CGA(R) | Csp45 I (TTCGAA) |
| H167R-R | GCAT<u>TCTAGA</u>TTCGAATGGCCTCGTACACG (SEQ ID No. 33) | | Xba I (TCTAGA) |
| H167RB-F67RB-R | T7 GCAT<u>TCTAGA</u>TT CGA ATGGCCTCGTACACG (SEQ ED No. 34) | XbaI (TCTAGA) | Csp45I (TTCGAA) |

[a] The product of ATT and ATC is the same amino acid, isoleucine.

The Primers Used for RT-PCR of OsNRT2.3 Gene

| Genes | Primers |
|---|---|
| OsNRT2.3a (AK072215) | F: 5'-GCTCATCCGCGACACCCT-3' (SEQ ID No. 35) R: 5'-GTCGAAGCGGTCGTAGAA-3' (SEQ ID No. 36) |
| OsNRT2.3b (AK072215) | F: 5'-CGTTCGCCGTGTT-3' (SEQ ID No. 37) R: 5'-TCGAAGCGGTCGTAGAAG-3' (SEQ ID No. 38) |
| OsActin (NM_197297) | F: 5'-TTATGGTTGGGATGGGACA-3' (SEQ ID No. 39) R: 5'-AGCACGGCTTGAATAGCG-3' (SEQ ID No. 40) |

TABLE 1

The growth period differences between OsNRT2.3b over-expression plants and Nipponbare wild type in FIG. 16 pot experiments.

| | Date (y/m/d) | | | | |
|---|---|---|---|---|---|
| | sowing | transplanting | 50% heading | flowering | maturity |
| WT | 2011 May 10 | 2011 Jun. 10 | 2011 Aug. 16 | 2011 Aug. 21 | 2011 Oct. 8 |
| b-S2 | 2011 May 10 | 2011 Jun. 10 | 2011 Sep. 1 | 2011 Sep. 6 | 2011 Oct. 28 |
| b-S6 | 2011 May 10 | 2011 Jun. 10 | 2011 Sep. 2 | 2011 Sep. 8 | 2011 Oct. 28 |

Note:
The soil pot experiment was performed with ten replications in an experimental farm of Nanjing Agricultural University (data shown in FIG. SF9). The acid soil (pH 6.0, soil: water = 1:1) collected from the farm. One wild type, b-S2 and b-S6 plants which belong to two independent lines were grown in each pot containing 15 kg of air-dried soil with 2.25 g N added (n = 10). The soil in the pot was flooded for 1 day before transplanting and the water maintained between 5 and 10 cm deep until 15 days before harvest. Maturity was recorded when most of the panicles in plot showed complete loss of green color. Five replicate pots of plant samples were harvested when WT plants were at maturity, and other five replication pots of plant samples were harvested when b-S2 and b-S6 plants were at maturity. The plants were dug out and separated into vegetative biomass and grains. All plant samples were oven-dried at 70° C., weighed and ground into powder, and were then subsampled for N determinations. N concentration in plant tissue and seed was determined by the standard macro-Kjeldahl procedure.

TABLE 2

The Agronomic traits of OsNRT2.3b over expression plants and WT in FIG. 16 pot experiments.

| | Panicle length (cm) | Panicle weight (g) | Number of primary rachis | Number of secondary rachis | Seed number/ Panicle | Weight/ 1000 seeds (g) | Ripening Rate (%) |
|---|---|---|---|---|---|---|---|
| WT   | 21.4 ± 0.4b | 3.2 ± 0.2b | 10.0 ± 0.5b | 20.4 ± 1.6a | 125.0 ± 7.9b | 24.1 ± 0.4a | 83.9 ± 3.3a |
| b-S2 | 26.2 ± 0.7a | 4.5 ± 0.3a | 14.2 ± 0.4a | 29.8 ± 2.6a | 225.3 ± 9.4a | 24.6 ± 0.4a | 87.0 ± 2.5a |
| b-S6 | 26.1 ± 0.4a | 4.4 ± 0.1a | 13.9 ± 0.4a | 27.9 ± 3.0a | 218.0 ± 11.8a | 24.3 ± 0.4a | 87.0 ± 2.6a |

Note:
Values are mean ±S.E (n = 10), small letters indicate significance of difference at 5% levels with One-way ANOVA analysis

TABLE 3

The effect of OsNRT2.3b over-expression on plant biomass transfer and accumulation in FIG. 16 pot experiments.

| Line | $f_D$ (g/plant) | $e_D - (f_D - f_{GD})$ (g/plant) | $(e_D - (f_D - f_{GD}))/ e_D$ (%) | $(e_D - (f_D - f_{GD}))/ f_{GD}$ (%) |
|---|---|---|---|---|
| WT   | 47.7 ± 1.0b | 2.1 ± 0.4b  | 5.9 ± 1.3b  | 14.3 ± 2.8b |
| b-S2 | 61.0 ± 0.7a | 11.0 ± 0.9a | 21.9 ± 1.7a | 50.2 ± 3.9a |
| b-S6 | 61.7 ± 0.6a | 11.9 ± 0.8a | 23.4 ± 1.6a | 52.8 ± 3.1a |

Note:
1) Values are mean ± S.E (n = 10). Small letters (a, b) indicate significance of difference at 5% levels compared with WT; 2) The pot experiments were conducted as described in Table 1; Dry matter translocation was calculated as $e_D - (f_D - f_{GD})$; Dry matter translocation efficiency was calculated as $(e_D - (f_D - f_{GD}))/e_D$; The contribution of dry matter translocation was calculated as $(e_D - (f_D - f_{GD}))/f_{GD}$.

TABLE 4

The effect of OsNRT2.3b over-expression on plant nitrogen transfer and accumulation in FIG. 18 pot experiments.

| Line | $f_N$ (mg/plant) | $e_N - (f_N - f_{GN})$ (mg/plant) | $e_N - (f_N - f_{GN})/ e_N$ (%) | $e_N - (f_N - f_{GN})/ f_{GN}$ (%) |
|---|---|---|---|---|
| WT   | 424.6 ± 6.4b | 109.4 ± 2.7b | 29.5 ± 0.9b | 67.2 ± 2.9b |
| b-S2 | 557.7 ± 2.9a | 199.0 ± 4.4a | 37.7 ± 0.6a | 87.0 ± 0.8a |
| b-S6 | 556.1 ± 9.3a | 209.7 ± 3.2a | 39.6 ± 0.4a | 88.6 ± 1.2a |

Note:
1) Values are mean ± S.E (n = 10). Small letters (a, b) indicate significance of difference at 5% levels compared with WT; 2) The pot experiments were conducted as described in Table 1; 3). Nitrogen translocation was calculated as $e_N - (f_N - f_{GN})$; nitrogen translocation efficiency was calculated as $e_N - (f_N - f_{GN})/e_N$; the nitrogen translocation contribution was calculated as $e_N - (f_N - f_{GN})/f_{GN}$;

TABLE 5

The Agronomic traits of OsNRT2.3b over expression plants and WT in FIG. 2a field experiments.

| | 0 kg N | 75 kg N | 150 Kg N | 300 kg N |
|---|---|---|---|---|
| | Dry weight (g/plant) | | | |
| WT   | 21.2 ± 0.6b | 21.9 ± 1.1b | 30.2 ± 1.0b | 28.2 ± 4.0b |
| b-U1 | 35.0 ± 2.2a | 40.5 ± 2.3a | 57.1 ± 2.3a | 60.8 ± 5.4a |
| b-U2 | 37.5 ± 1.7a | 40.5 ± 3.1a | 59.4 ± 3.4a | 64.3 ± 3.5a |
| b-S2 | 37.1 ± 1.9a | 40.1 ± 3.6a | 57.9 ± 4.1a | 63.4 ± 5.7a |
| b-S6 | 38.4 ± 3.1a | 40.6 ± 2.8a | 60.6 ± 4.8a | 65.5 ± 5.2a |
| | Effective tillering No. | | | |
| WT   | 9.3 ± 0.9a | 9.3 ± 0.8a | 11.0 ± 1.5a | 11.3 ± 1.1a |
| b-U1 | 8.1 ± 0.9a | 8.5 ± 0.9a | 10.2 ± 1.5a | 9.3 ± 1.3a |
| b-U2 | 8.1 ± 1.1a | 8.6 ± 1.0a | 9.2 ± 1.8a | 9.2 ± 1.2a |
| b-S2 | 8.2 ± 1.2a | 8.4 ± 13a | 9.3 ± 1.9a | 9.5 ± 1.2a |
| b-S6 | 8.3 ± 1.1a | 8.6 ± 1.1a | 9.4 ± 1.7a | 9.2 ± 1.1a |
| | Seed No./panicle | | | |
| WT   | 116 ± 4.4b | 119 ± 7.1b | 117 ± 6.4b | 120 ± 6.4b |
| b-U1 | 140 ± 8.0a | 159 ± 9.5a | 142 ± 8.0a | 154 ± 7.0a |
| b-U2 | 148 ± 9.1a | 164 ± 10.1a | 165 ± 9.1a | 167 ± 11.1a |
| b-S2 | 148 ± 8.6a | 160 ± 9.1a | 165 ± 9.6a | 163 ± 12.6a |
| b-S6 | 152 ± 8.9a | 174 ± 11.4a | 170 ± 8.9a | 180 ± 13.9a |
| | Weight/1000 seeds | | | |
| WT   | 23.2 ± 0.2a | 24.4 ± 0.2a | 24.6 ± 0.2a | 25.0 ± 0.6a |
| b-U1 | 23.2 ± 0.2a | 24.2 ± 0.4a | 24.2 ± 0.3a | 25.0 ± 0.3a |
| b-U2 | 23.0 ± 0.3a | 24.3 ± 0.2a | 24.1 ± 0.4a | 25.2 ± 0.6a |
| b-S2 | 22.9 ± 0.3a | 24.2 ± 0.3a | 24.1 ± 0.5a | 25.0 ± 0.8a |
| b-S6 | 23.0 ± 0.3a | 24.3 ± 0.4a | 24.1 ± 0.4a | 25.0 ± 0.8a |
| | Ripening rate (%) | | | |
| WT   | 64.9 ± 2.4b | 68.1 ± 2.2b | 78.9 ± 2.8b | 83.3 ± 2.2b |
| b-U1 | 72.0 ± 2.0a | 78.0 ± 1.5a | 88.0 ± 2.9a | 95.1 ± 3.0a |
| b-U2 | 73.0 ± 1.9a | 78.8 ± 2.9a | 88.3 ± 2.4a | 94.5 ± 2.9a |
| b-S2 | 72.0 ± 2.6a | 78.8 ± 2.3a | 89.0 ± 2.2a | 93.5 ± 1.6a |
| b-S6 | 74.0 ± 2.8a | 79.5 ± 2.4a | 88.0 ± 2.6a | 92.9 ± 3.1a |
| | Grain weight (g/plant) | | | |
| WT   | 16.2 ± 0.4b | 18.6 ± 0.9b | 24.7 ± 0.8b | 28.2 ± 1.0b |
| b-U1 | 18.9 ± 1.4a | 25.5 ± 1.5a | 31.8 ± 1.3a | 34.0 ± 2.0a |
| b-U2 | 20.1 ± 0.9a | 27.1 ± 2.1a | 32.5 ± 1.8a | 36.7 ± 2.0a |
| b-S2 | 20.0 ± 1.0a | 25.6 ± 2.0a | 33.0 ± 2.3a | 36.1 ± 2.3a |
| b-S6 | 21.5 ± 1.7a | 28.8 ± 2.0a | 33.9 ± 2.7a | 38.2 ± 2.4a |

Note:
Ten plants from each replication of each treatment were sampled for this agronomic analysis and three replication. Values are mean ± S.E. (n = 30). Small letters (a, b) indicate significance of difference at 5% levels compared with WT.

SEQUENCE LISTING

OsNRT23.b nucleic acid sequence, Accession No: AK072215 longest ORF,
see http://cdna01.dna.affrc.go.jp/cDNA/report/KOME_AK072215.html
SEQ ID No. 1
ATGGAGGCTAAGCCGGT
GGCGATGGAGGTGGAGGGGGTCGAGGCGGCGGGGGGCAAGCCGCGGTTCAGGATGCCGGT
GGACTCCGACCTCAAGGCGACGGAGTTCTGGCTCTTCTCCTTCGCGAGGCCACACATGGC
CTCCTTCCACATGGCGTGTTCTCCTTCTTCTGCTGCTTCGTGTCCACGTTCGCCGTGTT
CGCGCGTCTGGCCATGGGCACGGCGTGCGACCTGGTCGGGCCCAGGCTGGCCTCCGCGTC

```
TCTGATCCTCCTCACCACACCGGCGGTGTACTGCTCCTCCATCATCCAGTCCCCGTCGGG
GTACCTCCTCGTGCGCTTCTTCACGGGCATCTCGCTGGCGTCGTTCGTGTCGGCGCAGTT
CTGGATGAGCTCCATGTTCTCGGCCCCCAAAGTGGGGCTGGCCAACGGCGTGGCCGGCGG
CTGGGGCAACCTCGGCGGCGGCGCCGTCCAGCTGCTCATGCCGCTCGTGTACGAGGCCAT
CCACAAGATCGGTAGCACGCCGTTCACGGCGTGGCGCATCGCCTTCTTCATCCCGGGCCT
GATGCAGACGTTCTCGGCCATCGCCGTGCTGGCGTTCGGGCAGGACATGCCCGGCGGCAA
CTACGGGAAGCTCCACAAGACTGGCGACATGCACAAGGACAGCTTCGGCAACGTGCTGCG
CCACGCCCTCACCAACTACCGCGGCTGGATCCTGGCGCTCACCTACGGCTACAGCTTCGG
CGTCGAGCTCACCATCGACAACGTCGTGCACCAGTACTTCTACGACCGCTTCGACGTCAA
CCTCCAGACCGCCGGGCTCATCGCCGCCAGCTTCGGGATGGCCAACATCATCTCCCGCCC
CGGCGGCGGGCTACTCTCCGACTGGCTCTCCAGCCGGTACGGCATGCGCGGCAGGCTGTG
GGGGCTGTGGACTGTGCAGACCATCGGCGGCGTCCTCTGCGTGGTGCTCGGAATCGTCGA
CTTCTCCTTCGCCGCGTCCGTCGCCGTGATGGTGCTCTTCTCCTTCTTCGTCCAGGCCGC
GTGCGGGCTCACCTTCGGCATCGTGCCGTTCGTGTCGCGGAGGTCGCTGGGGCTCATCTC
CGGGATGACCGGCGGCGGGGGCAACGTGGGCGCCGTGCTGACGCAGTACATCTTCTTCCA
CGGCACAAAGTACAAGACGGAGACCGGGATCAAGTACATGGGGCTCATGATCATCGCGTG
CACGCTGCCCGTCATGCTCATCTACTTCCCGCAGTGGGGCGGCATGCTCGTAGGCCCGAG
GAAGGGGGCCACGGCGGAGGAGTACTACAGCCGGGAGTGGTCGGATCACGAGCGCGAGAA
GGGTTTCAACGCGGCCAGCGTGCGCGTTCGCGGAGAACAGCGTGCGCGAGGGCGGGAGGTC
GTCGGCGAATGGCGGACAGCCCAGGCACACCGTCCCCGTCGACGCGTCGCCGGCCGGGGT
GTGA

OsNRT2.3a nucleic acid sequence, Accession No: AK109776 longest ORF
SEQ ID No. 2
ATGGAGGCTAAGCCGGTG
GCGATGGAGGTGGAGGGGGTCGAGGCGGCGGGGGGCAAGCCGCGGTTCAGGATGCCGGTG
GACTCCGACCTCAAGGCGACGGAGTTCTGGCTCTTCTCCTTCGCGAGGCCACACATGGCC
TCCTTCCACATGGCGTGGTTCTCCTTCTTCTGCTGCTTCGTCACGTTCGCCGCGCCG
CCGCTGCTGCCGCTCATCCGCGACACCCTCGGGCTCACGGCCACGGACATCGGCAACGCC
GGGATCGCGTCCGTGTCGGCGCCGTGTTCGCGCGTCTGGCCATGGGCACGGCGTGCGAC
CTGGTCGGGCCCAGGCTGGCCTCCGCGTCTCTGATCCTCCTCACCACACCGGCGGTGTAC
TGCTCCTCCATCATCCAGTCCCCGTCGGGGTACCTCCTCGTGCGCTTCTTCACGGGCATC
TCGCTGGCGTCGTTCGTGTCGGCGCAGTTCTGGATGAGCTCCATGTTCTCGGCCCCCAAA
GTGGGGCTGGCCAACGGCGTGGCCGGCGGCTGGGGCAACCTCGGCGGCGGCGCCGTCCAG
CTGCTCATGCCGCTCGTGTACGAGGCCATCCACAAGATCGGTAGCACGCCGTTCACGGCG
TGGCGCATCGCCTTCTTCATCCCGGGCCTGATGCAGACGTTCTCGGCCATCGCCGTGCTG
GCGTTCGGGCAGGACATGCCCGGCGGCAACTACGGGAAGCTCCACAAGACTGGCGACATG
CACAAGGACAGCTTCGGCAACGTGCTGCGCCACGCCCTCACCAACTACCGCGGCTGGATC
CTGGCGCTCACCTACGGCTACAGCTTCGGCGTCGAGCTCACCATCGACAACGTCGTGCAC
CAGTACTTCTACGACCGCTTCGACGTCAACCTCCAGACCGCCGGGCTCATCGCCGCCAGC
TTCGGGATGGCCAACATCATCTCCCGCCCCGGCGGCGGGCTACTCTCCGACTGGCTCTCC
AGCCGGTACGGCATGCGCGGGAGGCTGTGGGGGCTGTGGACTGTGCAGACCATCGGCGGC
GTCCTCTGCGTGGTGCTCGGAATCGTCGACTTCTCCTTCGCCGCGTCCGTCGCCGTGATG
GTGCTCTTCTCCTTCTTCGTCCAGGCCGCGTGCGGGCTCACCTTCGGCATCGTGCCGTTC
GTGTCGCGGAGGTCGCTGGGGCTCATCTCCGGGATGACCGGCGGCGGGGGCAACGTGGGC
GCCGTGCTGACGCAGTACATCTTCTTCCACGGCACAAAGTACAAGACGGAGACCGGGATC
AAGTACATGGGGCTCATGATCATCGCGTGCACGCTGCCCGTCATGCTCATCTACTTCCCG
CAGtGGGGCGGCATGCTCGTAGGCCCGAGGAAGGGGGCCACGGCGGAGGAGTACTACAGC
CGGGAGTGGTCGGATCACGAGCGCGAGAAGGGTTTCAACGCGGCCAGCGTGCGCGTTCGCG
GAGAACAGCGTGCGCGAGGGCGGGAGGTCGTCGGCGAATGGCGGACAGCCCAGGCACACC
GTCCCCGTCGACGCGTCGCCGGCCGGGGTGTGA OsNRT2.3b amino acid sequence (Longest ORF)
SEQ ID No. 3
MEAKPVAMEVEGVEAAGGKPRFRMPVDSDLKATEFWLFSFARPHMASFHMAWFSFFCCFV
STFAVFARLAMGTACDLVGPRLASASLILLTTPAVYCSSIIQSPSGYLLVRFFTGISLAS
FVSAQFWMSSMFSAPKVGLANGVAGGWGNLGGGAVQLLMPLVYEAIHKIGSTPFTAWRIA
FFIPGLMQTFSAIAVLAFGQDMPGGNYGKLHKIGDMHKDSFGNVLRHALTNYRGWILALT
YGYSFGVELTIDNVVHQYFYDRFDVNLQTAGLIAASFGMANIISRPGGLLSDWLSSRYG
MRGRLWGLWTVQTIFFVLCVVLGIVDFSFAASVAVMVLFSFFVQAACGLTFGIVPFVSRR
SLGLISGMTGGGNVGAVLTQYIFFHGTKYKTETGIKYMGLMIIACTLPVMLIYFPQWGG
MLVGPRKGATAEEYYSREWSDHEREKGFNAASVRFAENSVREGGRSSANGGQPRHTVPVD
ASPAGV OsNRT2.3a amino acid sequence
SEQ ID No. 4
MEAKPVAMEVEGVEAAGGKPRFRMPVDSDLKATEFWLFSFARPHMASFHMAWFSFFCCFV
STFAAPPLLPLIRDTLGLTATDIGNAGIASVSGAVFARLAMGTACDLVGPRLASASLILL
TTPAVYCSSIIQSPSGYLLVRFFTGISLASFVSAQFWMSSMFSAPKVGLANGVAGGWGNL
GGGAVQLLMPLVYEAIHKIGSTPFTAWRIAFFIPGLMQTFSAIAVLAFGQDMPGGNYGKL
HKTGDMHKDSFGNVLRHALTNYRGWILALTYGYSFGVELTIDNVVGQYFYDRFDVNLQTA
GLIAASFGMANIISRPGGGLLSDWLSSRYGMRGRLWGLWTVQTIGGVLCVVLGIVDFSFA
ASVAVMVLFSFFVQAACGLTFGIVPFVSRRSLGLISGMTGGGNVGAVLTQYIFFHGTKY
KTETGIKYMGLMIIACTLPVMLIYFPQWGGMLVGPRKGATAEEYYSREWSDHEREKGFNA
ASVRFAENSVREGGRSSANGGQPRHTVPVDASPAGV
```

SEQUENCE LISTING

Phloem promoter sequence
SEQ ID No. 5
61 CAAATGTGCA ATGCTGATTA GAGTTTGCAG ATGCTGTTTG GTTTAGTTTA
GATGTGGCATTTTGTTAGTG GTTTCTTTGA TGAAAAATTC TTGGCTATGA TAAAGTTTGC
TTTCTGAATATATGAATAGT GGCCATGGTT CAAGAAACTC CAGTTAGGTG GGATAATTTA
TGGTGATTCTGGGCGCAATT CGGGGAAATT TTTTTTGGCG AGAATCTTAT CATTGAGATA
AAGAGGGCAAGAATATCAAC AGACTTTTAA TCTTAATAAA AAGCACTCTT AGCGTAAGAG
CAAAGCATTGCAATCTCGTG TGACAAGAAC GTTTCTTTTT CTCCATCTTT TTCTTTTTTA
CCAAAAAATGAGTGTTGCCA ACTGCTGCAC CTTCTTAGGC CGGTTTGTTC TTGTTTGGAA
CGCACGGAATGCCCGATGCA AAAAAAAAAA AGAAATGCTG TTAACAAATC ACTGTCCTGA
CACGGCTAATTAGGTGGTAA TTTGGTGCAT CTGCAAAGAA GCAACAGATG CTTTCTTTCA
CTGAAAGCATATTTGCATGA TTTCTTGTTT CTGCTTGTCC TCTCTCTGAT GCTGACTGTA
TTCCACTCTGCGCTGTAATG CCATGTTAGT GATTAATATG TTCAAAAGAG CATAAAAGAA
TTGCCAATTGGATGTTAGAG ATTACTGTGT TGTTCAAAAG AGCATAAAAG AATTACCAAT
TTGATGGTAGATGTTACTAG CACCACCTTG GTGTTTGCCC ATGGTTTTCT GCAATTCTGC
CCATGATCTTTCTGCTTTTC TGAAAGACCT ATGTTTCAGA GGTCAAGCTT CTGGAAGGTT
ATTAGGAGGGATGAGTCGTC ATTTTGTCTG TGGGCCCCAC TAGTCAGTGT CAATAGTTGT
AAAGGGTAGAAATTTTCTTG CTGTTTTTCT TGGAAACAAT TTCATTGCGC CTGATCTGAT
GGTCGGTCTGGTAATCAAAT CACCAGATCC TGAAATCCAC CAAATCAAAC CGTGAGATTT
TTGCAGAGGCAAAACAAGAA AAGCATCTGC TTTATTTCTC TCTTGCTTTC TTTTCATCCC
CAACCAGTCCTTTTTTCTTC TGTTTATTTG TAGAAGTCTA CCACCTGCAG TCTATTATTC
TACAGAGAAAAAGATTGAAG CTTTTTTTCT CCAAAGCTGA CAATGGTGCC GGCATATGCT
AATAGGATACTCCCTTCGTC TAGGAAAAAA CCAACCCACT ACAATTTTGA ATATATATTT
ATTCAGATTTGTTATGCTTC CTACTCCTTC TCAGGTATGG TGAGATATTT CATAGTATAA
TGAATTTGGACATATATTTG TCCAAATTCA TCGCATTATG AAATGTCTCG TTCGATCTAT
GTTGTTATATTATAGACGGA GATAGTAGAT TCGGTTATTT TTGGACAGAG AAAGTACTCG
CCTGTGCTAGTGACATGATT AGTGACACCA TCAGATTAAA AAAACATATG TTTTGATTAA
AAAAATGGGGAATTTGGGGG GAGCAATAAT TTGGGGTTAT CCATTGCTGT TTCATCATGT
CAGCTGAAAGGCCCTACCAC TAAACCAATA TCTGTACTAT TCTACCACCT ATCAGAATTC
AGAGCACTGGGGTTTTGCAA CTATTTATTG GTCCTTCTGG ATCTCGGAGA AACCCTCCAT
TCGTTTGCTCTTAATTAAAA GGGCAATTCT GCAGATATCC ATCACACTGG CGGCCGCTCG
AGCATGCATCTAGAGGCCCA ATTCGCCCA Zea mays Id No. GRMZM2G455124* nucleic acid sequence
SEQ ID No. 6
ATGGCGGAGGGGGAGTTCAAGCCCGCGGCGATGCAGGTGGAGGCTCCTGCCGAGGCGGCG
GCGGCGCCGTCCAAGCCGCGGTTCAGGATGCCCGTCGACTCCGACAACAAGGCCACCGAG
TTCTGGCTCTTCTCCTTCGCGAGGCCGCACATGAGCGCCTTCCACATGTCGTGGTTCTCC
TTCTTCTGCTGCTTCCTCTCCACCTTCGCGGCGCCGCCGCTGCTCCCGCTCATCCGGGAC
ACGCTGGGGCTCACGGCCACGGACATCGGCAACGCCGGGATCGCCTCCGTGTCCGGCGCG
GTCTTCGCGCGCGTGGCCATGGGCACGGCGTGCGACCTGGTGGGCCCGCGCCTGGCGTCC
GCGGCCATCATACTCCTCACCACGCCCGCCGTCTACTACTCCGCCGTCATCGACTCCGCC
TCGTCCTACCTGCTCGTGCGCTTCTTCACGGGCTTCTCGCTCGCGTCCrTCGTGTCCACG
CAGTTCTGGATGAGCTCCATGTTCTCGCCGCCCAAGGTGGGGCTGGCCAACGGCGTCGCC
GGGGGGTGGGGCAACCTCGGCGGCGGCGCCGTGCAGCTCATCATGCCGCTCGTGTTCGAG
GCCATCCGCAAGGCCGGGGCCACGCCGTTCACGGCGTGGCGCGTCGCCTTCTTCGTCCCG
GGCCTGCTGCAGACGCTGTCGGCCGTCGCCGTGCTGGCGTTCGGCCAGGACATGCCCGAC
GGCAACTACCGCAAGCTGCACAGGTCCGGCGACATGCACAAGGACAGCTTCGGCAACGTG
CTCCGCCACGCCGTCACCAACTACCGCGCCTGGATCCTGGCGCTCACCTACGGATACTGC
TTCGGCGTGGAGCTCGCCGTGGACAACATCGTCGCGCAGTACTTCTACGACCGCTTCGGC
GTCAAGCTCAGCACCGGCTTCATCGCCGCCAGCTTCGGGATGGCCAACATCGTCTCC
CGCCCCGGCGGCGGCCTCCTGTCGGACTGGCTCTCCAGCCGCTTCGGCATGCGCGGCAGG
CTGTGGGGCCIGTGGGTGGTGCAGACCATCGGGGCGTCCTCTGCGTCGTGCTCGGCGCC
GTCGACTACTCCTTCGCCGCGTCCGTGGCCGTCATGATACTCTTCTCCATGTTCGTGCAG
GGGGCCTGCGGGCTCACCTTTGGCATCGTCCCGTTCGTCTCCCGAAGGTCGCTGGGGCTC
ATCTCCGGCATGACCGGCGGCGGCGGCAACGTGGGCGCCGTGCTCACGCAGCTCATCTTC
TTCCACGGATCCAAGTACAAGACGGAGACGGGGATCAAGTACATGGGGTTCATGATCATC
GCCTGCACGTTGCCCATCACGCTCATCTACTTCCCGCAGTGGGGCGGCATGTTCCTGGGG
CCGCGGCCCGGGCGACGGCGGAGGACTACTACAACCGGGAGTGGACAGCGCACGAGTGC
GACAAGGGTTTCAACACCGCGAGCGTACGCTTTGCGGAGAACAGCGTGCGGGAAGGGGGA
CGCTCGGGCAGCCAGTCCAAGCACACTACTGTGCCCGTCGAGTCCTCGCCGGCCGACGTG
TGA Zea mays Id No. GRMZM2G455124* amino acid sequence
SEQ ID No. 7
MAEGEFKPAAMQVEAPAEAAAAPSKPRFRMPVDSDNKATEFWLFSFARPHMSAFHMSWFSFFCCFLSTFA
APPLLPLIRDTLGLTATDIGNAGIASVSGAVFARVAMGTACDLVGPRLASAAIILLTTPAVYYSAVIDSA
SSYLLVRFFTGFSLASFVSTQFWMSSMFSPPKVGLANGVAGGWGNLGGGAVQLIMPLVFEAIRKAGATPF
TAWRVAFFVPGLLQTLSAVAVLAFGQDMPDGNYRKLHRSGDMHKDSFGNVLRHAVTNYRAWILALTYGYC
FGVELAVDNIVAQYFYDRFGVKLSTAGFIAASFGMANIVSRPGGGLLSDWLSSRFGMRGRLWGLWVVQTG
GVLCVVLGAVDYSFAASVAVMILFSMFVQAACGLTFGIVPFVSRRSLGLISGMTGGGGNVGAVLTQLIFF
HGSKYKTETGIKYMGFMIIACILPITLIYFPQWGGMFLGPRPGATAEDYYNREWTAHECDKGFNTASVRF
AENSVREGGRSGSQSKHTTVPVESSPADV

SEQUENCE LISTING

Glycine max Id No. Glyma13g39850 nucleic acid sequence
SEQ ID No. 8

```
TCACACTTTCTTCCTTAATTTTCTAGCTCTTGCTACGTACTTGAATTCAATTAGTTATTA
ATGGCTGAGATTGAGGGTTCTCCCGGAAGCTCCATGCATGGAGTAACAGGAAGAGAACAA
ACATTTGTAGCCTCAGTTGCTTCTCCAATTGTCCCTACAGACACCACAGCCAAATTTGCT
CTCCCAGTGGATTCAGAACACAAGGCCAAGGTTTTCAAACTCTTCTCCCTGGCCAATCCC
CACATGAGAACCTTCCACCTTTCTTGGATCTCCTTCTTCACCTGCTTCGTCTCGACATTC
GCAGCAGCACCTCTTGTGCCCATCATCCGCGACAACCTTAACCTCACCAAAAGCGACATT
GGAAACGCCGGGGTTGCTTCTGTCTCCGGAAGCATCTTCTCAAGGCTCGCAATGGGTGCA
GTCTGTGACATGTTGGGTCCACGCTATGGCTGCGCCTTCCTCATCATGCTTTCGGCCCCT
ACGGTGTTCTGCATGTCCTTTGTGAAAGATGCTGCGGGGTACATAGCGGTTCGGTTCTTG
ATTGGGTTCTCGTTGGCGACGTTTGTGTCGTGCCAGTACTGGATGAGCACGATGTTCAAC
AGTAAGATTATAGGGCTTGCGAATGGGACTGCTGCGGGGTGGGGGAACATGGGTGGTGGA
GCCACTCAGCTCATAATGCCTTTGGTGTATGAGCTTATCAGAAGAGCTGGGGCTACTCCC
TTCACTGCTTGGAGGATTGCCTTCTTTGTTCCGGGTTTCATGCATGTCATCATGGGGATT
CTTGTCCTCACTCTAGGCCAGGACTTGCCTGATGGAAACCTCGGGGCCTTGCGGAAGAAG
GGTGATGTAGCTAAAGACAAGTTTTCCAAGGTGCTATGGTATGCCATAACAAATTACAGG
ACATGGATTTTTGCTCTCCTCTATGGGTACTCCATGGGAGTTGAATTAACAACTGACAAT
GTCATTGCTGAGTATTTCTATGACAGATTTAATCTCAAGCTACACACTGCTGGAATCATT
GCTGCTTCATTTGGAATGGCAAACTTAGTTGCTCGACCTTTTGGTGGATATGCTTCAGAT
GTTGCAGCCAGGCTGTTTGGCATGAGGGGAAGACTCTGGACCCTTTGGATCCTCCAAACC
TTAGGAGGGTTTTCTGTATrTGGCTTGGCCGTGCCAATTCTCTTCCTATTGCTGTATTG
GCCATGATCCTGTTCTCTATAGGAGCTCAAGCTGCATGTGGTGCAACTTTTGGCATCATT
CCTTTCATCTCAAGAAGGTCTTTGGGGATCATATCAGGTCTAACTGGTGCAGGTGGAAAC
TTTGGGTCTGGCCTCACCCAATTGGTCTTCTTTTCAACCTCCAAATTCTCTACTGCCACA
GGTCTCTCCTTGATGGGTGTAATGATAGTGGCTTGCACTCTACCAGTGAGTGTTGTTCAC
TTCCCACAGTGGGGTAGCATGTTTCTACCACCCTCAAAAGATGTCAGCAAATCCACTGAA
GAATTCTATTACACCTCTGAATGGAATGAGGAAGAGAAGCAGAAGGGTTTGCACCAGCAA
AGTCTCAAATTTGCTGAGAATAGCCGATCTGAGAGAGGAAAGCGAGTGGCTTCAGCACCA
ACACCTCCAAATGCAACTCCCACTCATGTCTAGCCATAGCACTTCAATCAAAGAAGATCA
TGAAACATAATTACTGAGCAGTATTGGGAATGAAGAACCATGAGTTGAAGAATTTTCTAA
TAAGAAATCTTGTAACATGTAGACATAGAATGTTCTGGTTCTGGTTTGCGTGTGGTGTAA
GAGTTGTCTACTTGTGGTAAGTCATAAGTATCATAATCAGTATGTCAATGCAGATCTTGA
TGCTGAGTATCAATAGTATCAAAAAAAAAA
```

Glycine max Id No. Glyma13g39850 amino acid sequence
SEQ ID No. 9

```
MAEIEGSPGSSMHGVTGREQTFVASVASPIVPTDTTAKFALPVDSEHKAKVFKLFSLANPHMRTFHLSWI
SFFTCFVSTFAAAPLVPIIRDNLNLTKSDIGNAGVASVSGSIFSRLMAGAVCDMLGPRYGCAFLIMLSAP
TVFCMSFVKDAAGYIAVRFLIGFSLATFVSCQYWMSTMFNSKIIGLANGTAAGWGNMGGGATQLIMPLVY
ELIRRAGATPFTAWRIAFFVPGFMHVIMGILVLTLGQDLPDGNLGALRKKGDVAKDKFSKVLWYAITNYR
TWIFALLYGYSMGVELTTDNVIAEYFYDRFNLKLHTAGIIAASFGMANLVARPFGGYASDVAARLFGMRG
RLWTLWILQTLGGVFCIWLGRANSLPIAVLAMILFSIGAQAACGATFGIIPPISRRSLGIISGLTGAGGN
FGSGLTQLVFFSTSFFSTATGLSLMGVMIVACTLPVSVVHFPQWGSMFLPPSKDVSKSTEEFYYTSEWNE
EEKQKGLHQQSLKFAENSRSERGKRVASAPTPPNATPTHV
```

Glycine max Id No. Glyma12g30050 nucleic acid sequence
SEQ ID No. 10

```
atggctgaga ttgagggttc tcctggaagc tccatgcatg gagtaacagg aagagaacaa
acattcgtag cctcaattgc ttctccaatt gtcccacag acaccacagc caaatttgct
ctcccagtag actcagagca aaggccaag attttcaaac tcttctccat ggccaatccc
cacatgagaa ccttccacct ttcttggatc tccttcttca cctgcttcgt ctcgaccttc
gcagcagccc ctcttgtccc catcatccgc gacaacctta acctccacaa aagcgacatt
ggaaacgccg gggttgcttc tgtctccgga agcatcttct ctaggcttgc aatgggtgcg
gtctgtgacc tattaggtcc acgttatggc tgtgccttcc tcatcatgct ctcggcccca
accgtgttct gcatgtcctt tgtgaaagat gctgcgggt acataatggt tcggttattg
ataggggttct ccttggcaac gttcgtgtca tgccagtact ggatgagcac gatgttcaac
agtaagatta tagggcttgc gaatggaact gctgcgggt ggggaacat gggtggtgga
gccactcagc tcataatgcc tttggtgtat gagcttatca gaagagctgg ggctactccc
ttcactgctt ggaggatagc cttctttgta ccgggtttca tgcatgtcat catggggatc
cttgtcctaa ctctaggcca ggacttgcct gatggaaacc ttgcggcctt gcagaagaag
ggtgatgtag caaaagacaa gttttccaag gtgctatggt atgccataac aaattacagg
acatggattt tgccctcct ctatgggtac tcaatgggag ttgaattgac aactgacaat
gtcattgctg agtatttcta tgacaggttt aatctgaagc tgcacactgc tggaatcatt
gctgcttcat ttggaatggc aaacttagtt gctcgacctt tggtggata tgcttctgat
gttgcagcca gattgtttgg catgagggga agactctgga cccttggat cctccaaaca
ttaggagggg ttttctgtat ttggcttggc cgagccaatt ctcttcctat tgctatttg
gctatgatcc tgttctcttt aggagctcaa gctgcatgtg gtgcaacttt tggcatcatt
cccttcatct caagaaggtc attggggatc atatcaggtc tcactggtgc aggtgggaac
tttgggtctg gcctcaccca attggtcttc ttttcaacat ccaaattctc cactgccaca
ggtctctcct tgatgggtgt gatgatagtg gcttgcactc ttcctgtgag tgttgttcat
tttccacagt ggggtagcat gttcctacca ccatcaaaag atgtcaacaa atccactgaa
gaattctatt acacctctga atggaatgag aagagaggc agaaaggctt gcatcagcaa
agtctcaagt ttgctgagaa tagccgatcc gagagaggaa agcgagtggc ttcagcacca acacctccga
atgcaactcc cactcatgtc
```

SEQUENCE LISTING

Glycine max Id No. Glyma12g300500 amino acid sequence
SEQ ID No. 11
```
MAEIEGSPGS SMHGVTGREQ TFVASIASPI VPTDTTAKFA LPVDSEHKAK IFKLFSMANP
HMRTFHLSWI SFFTCFVSTF AAAPLVPIIR DNLNLTKSDI GNASVASVSG SIFSRLAMGA
VCDLLGPRYG CAFLIMLSAP TVFCMSFVKD AAGYIMVRFL IGFSLATFVS CQYWMSTMFN
SKIIGLANGT AAGWGNMGGG ATQLIMPLVY ELIRRAGATP FTAWRIAFFV PGFMHVIMGI
LVLTLGQDLP DGNLAALQKK GDVAKDKFSK VLWYAIINYR TWIGALLYGY SMGVELIIDN
VIAEYFYDRF NLKLHIAGII AASFGMANLV ARPFGGYASD VAARLFGMRG RLWTLWILQT
LGGVFCIWLG RANSLPIAIL AMILFSLGAQ AACGATFGII PFISRRSLGI ISGLTGAGGN
FGSGLTQLVF FSTSKFSTAT GLSLMGVMIV ACTLPVSVVH PPQWGSMFLP PSKDVNKSTE
EFYYTSEWNE EERQKGLHQQ SLKFAFNSRS ERGKRVASAP TPPNATPTHV
```

Hordeum vulgare Id No. MLOC_75087.1 nucleic acid sequence
SEQ ID No. 12
```
CCACGCGTCCGCTCATIGCATACGAGGTTGCCAACACTAraCAGGTGTAGCAGCAGCCAA
GGCAGCTGGTGAGATGGAGGGGGAGTCCAAGCCGGCGGCGATGGGGGTGCAGGCGGCGCC
CAAGGGCAAGTTCAGGATACCGGTGGACTCGGACAACAAGGCCACCGAGTTCTGGCTTTT
CTCGTTCGTGAGGCCGCACATGAGCGCCTTCCACCTCTCGTGGTTCTCCTTCTTCTGCTG
CTTCGTCTCCACCTTCGCCGCGCCGCCCCTCCTGCCGCTCATCCGGGACAACCTCGGCCT
CACGGGCAAGGACATCGGCAACGCCGGCATCGCGTCCGTGTCGGGCGCCGTGTTCGCGCG
TCTCGCCATGGGCACGGCCTGCGACCTGGTCGGGCCCCGCCTGGCGTCCGCGGCCATCAT
ACTGCTCACCACCCCCGCGGTGTACTGCTCCGCCATCATCGAGTCCGCCTCGTCGTTCCT
GCTCGTGCGCTTCTTCACGGGCITCTCGCTCGCCTCCrTCGTGTCGACGCAGTTCTGGAT
GAGCTCCATGTTCTCTTCGCCCAAGGTGGGGCTGGCCAATGGCGTCGCCGGCGGCTGGGG
CAACCTGGGCGGGGGCGCCGTGCAGCTCCTCATGCCGCTCGTGTTCGAGGCCGTCCGCAA
GATCGGCAGCACGGATTTCATCGCGTGGCGCGTCGCCTTCTTCATCCCGGGCGTCATGCA
GACGTTCTCGGCCATCGCCGTGCTGGCGTTCGGGCAGGACATGCCGGACGGCAACTACCG
TAAGCTGCACAAGAGCGGGGAGATGCACAAGGACAGCTTCGGCAACGTGCTGCGCCACGC
GGTCACGAACTACCGCGCCTGGATCCTGGCGCTCACCTACGGCTACTCCTTCGGCGTGGA
GCTCGCCGTGGACAACATCGTCGCGCAGTACTTCTACGACCGCTTCGACGTCAACCTCCA
CACGGCCGGGCTCATCGCCGCCAGCTTCGGGATGGCCAACATCATCTCCCGCCCGGGCGG
CGGGCTCATGTCCGACTGGCTCTCCGACCGGTTCGGCATGCGCGGCAGGCTGTGGGGGCT
GTGGGTCGTGCAGACCATCGGCGGCATCCTCTGCATCGTGCTCGGCATCGTCGACTACTC
GTTCGGCGCGTCGGTGGCCGTCATGATCCTCTTCTCCTTCTTCGTGCAGGCGGCGTGCGG
GCTCACGTTCGGCATCGTGCCGTTCGTGTCGCGGAGGTCGCTGGGGCTCATCTCCGGAAT
GACCGGCGGCGGCGGCAACGTGGGGGCCGTGCTGACGCAGGTCATCTTCTTCCGCGGCAC
CAAGTACAAGACGGAGACGGGGATCATGTACATGGGGCTGATGATCCTGGCATGCACGCT
GCCCATCACGCTCATCTACTTCCCGCAGTGGGGCGGCATGTTCGTCGGGCCGCGGAAAGG
GGCGACGGCGGAGGAGTACTACAGCAAGGAGTGGACCGAGGAGGAGCGTGCCAAGGGGTA
CAGCGCCGCGACCGAGCGTTTCGCGGAGAACAGCGTGCGCGAGGGCGGGCGGAGGGCGGC
GTCGGGCAGCCAGTCAAGGCACACCGTCCCCGTCGACGGCTCGCCGGCCGACGTGTGAGG
TCCGAAGAGCTCCCCGTACTACGTGGTCCACGGGTGCAATGGGGGAATACGATCGCGTCG
CACGGCCGCCCGGGTTTGGGCCGTCTTCCGTGCACATACGTAGTACTACGAACGCACGCA
CGCACGCCGGCTTTGTGCTGCTTCTAGTACTGTACGTACGTTTGGGTTTGGTGTGCTCGC
TTACCTTAATACTGCTCCGCATGTTGATGTTTATATGCTCCCTTGTGAAATACAGTTTTA
AAAAAAAAAAAAAAA
```

Hordeum vulgare Id No. MLOC_75087.1 nucleic acid sequence
SEQ ID No. 13
```
MEGESKPAAMGVQAAPKGKFRIPVDSDNKATEFWLFSFVRPHMSAFHLSWFSFFCCFVSTFAAPPLLPLI
RDNLGLTGKDIGNAGIASVSGAVFARLAMGTACDLVGPRLASAAIILLTTPAVYCSAIIESASSFLLVRF
FTGFSLASFVSTQFWMSSMFSSPKVGLANGVAGGWGNLGGGAVQLLMPLVFEAVRKIGSTDFIAWRVAFF
IPGVMQTFSAIAVLAFGQDMPDGNYRKLHKSGEMHKDSFGNVLRHAVTNYRAWILALTYGYSFGVELAVD
NIVAQYFYDRFDNVLHTAGLIAASFGMANIISRPGGGLMSDWLSDRFGMRGRLWGLWVVQTIGGILCIVL
GIVDYSFGASVAVMILFSFFVQAACGLTFGIVPFVSRRSLGLISGMTGGGGNVGAVLTQVIFFRGTKYKT
ETGIMYMGLMILACTLPITLIYFPQWGGMFVGPRKGATAEEYYSKEWTEEERAKGYSAATERFAENSVRE
GGRRAASGSQSRHTVPVDGSPADV
```

Brachypodium distachyon Id No. Bradi2g47640 nucleic acid sequence
SEQ ID No. 14
```
ATGGQGQGGAGTCGAAGCCGGCGGCGATGGATGTGGAGGCGCCGTCCAAGGCCA
AGTTCAGGATCCCCGTGGACTCCGACAACAAGGCGACGGAGTTCTGGCTCTTCTCC
TTCGCGCGGCCGCACATGAGCGCGTTCCACCTGTCGTGGCTCCTTCTTCTGCTGC
TTCGTGTCCACCTTCGCGGCGCCGCCGCTGCTGCCGCTCATCCGGGACAATCTGGGG
CTCACGGCCAAGGACATCGGCAACGCCGGGATCGCGTCGGTGTCGGGCGCCGTGTT
CGCGCGTCTCGCCATGGGCACGGCCTGCGACCTGGTCGGCCCCCGCCTGGCGTCCG
CGGCCATCATACTGCTCACCACCCCGGCGGTGTACTGCTCGGCCATCATCGACTCG
GCGTCGTCGTTCCTGCTCGTGCGCTTCTTCACGGGCTTCTCCCTGGCCTCCTTCGTGT
CCACGCAGTTCTGGATGAGCTCCATGTTCTCCTCGCCCAAGGTGGGTCTGGCCAAC
GGCGTGGCCGGGGGCTGGGGCAACCTCGGCGGCGGCGCCGTGCAGCTGATCATGC
CGCTGGTGTTCGAGGTCGTGCGCAGATCGGGAGCACGCGGTTCACGGCGTGGCGC
GTGGCCTTCTTCATCCCGGGCGTCATGCAGACGTTCTCGGCCATCGCCGTGCTGGCG
TTCGGGCAGGACATGCCGGACGGCAACTAGCACAAGCTGCACAAGACCGGGGAGA
TGCACAGGGACAGCTTCCGCAACGTGCTGCGCCACGCGGTCACCAACTACCGCGCC
TGGATCCTGGCGCTCACCTACGGCTACTGCTTCGGCGTGGAGCTCGCCGTGGACAA
CATCGTGGCGCAGTACTTCTACGACCGCTTCGGCGTCAACCTCCACACGGCGGGGC
TCATCGCCGCCAGCTTCGGGATGGCCAACATCGTCTCGCGCCCCGGGCGGCGGGCTC
```

SEQUENCE LISTING

```
ATGTCCGACTGGCTCTCGGCCCGGTTCGGCATGCGCGGCAGGCTGTGGGGCCTGTG
GGTCGTGCAGACCATCGGCGGCGTCCTCTGCGTGGTGCTCGGCGTGGTGGACTACT
CCTTCGGCGCGTCCGTGQCAGTCATGATACTCTTCTCCCTGTTCGTGCAGGCCGCGT
GCGGGCTCACCTTCGGCATCGTGCCGTTCGTGTCGCGGAGGTCGCTGGGGCTCATCT
CTGGCATGACCGGCGGCGGGGGAAATGTGGGCGCCGTGCTGACGCAGGTCATCTTC
TTCCACGGGTCCAGGTACAAGACGGAGACGGGGATCATGTACATGGGGGTCATGAT
CATCGCGTGCACGCTGCCCATCACGCTCATCTACTTCCCGCAGTGGGGCGGCATGTT
CACCGGGCCGCGGCCGGGGGCCACGGCGGAGGAGTATTACAGCTCGGAGTGGACC
GAGGAGGAGCGGAAGAAAGGGTACAACGCCGCGACAGAGCGTTTCGCGGAGAAC
AGCCTGCGCGAGGGAGGGCGGAGGGCCGCGTCGGGCAGCCAGTCCAAGCATACCG
TCCCCGTGGACGGATCACCGCCGGCCGACGTGTGAAGAAAATCCCATAGACCATAG
TGTACGTTTCGTATGTCTCGCGTCTATAACGAGTCATACGGTCGCCACGGTCGCCGG
TCTGGTTACGTGCGTTGGCTTTTTrATGTGTTGTACCTTTTGGCTTTTGGTGCTCCTTT
GTCTTGTTGCTGTAAAAGGTTGTCAAATACTCCACTTTTCTTTTCCGCAGACGTGAA
ATACTTCTGTAGGTGTACGTCACTGAAAGGAAACTGTTCATATGGCATCCACATAC
AAAACCATGTTTTCTTATATTGCTAGTATATTCGTTTTTCTTATTTCGACGAAACTAG
CATTCCGCGTCTATTATTATTCGTAAGATACTTCCGATCGAAAA

Brachypodium distachyon Id No. Bradi2g47640 nucleic acid sequence
SEQ ID No. 15
MGGESKPAAMDVEAPSKAKFRIPVDSDNKATEFWLFSFARPHMSAFHLSWFSFFCCFV
STFAAPPLLPLIRDNLGLTAKDIGNAGIASVSGAVFARLAMGTACDLVGPRLASAAHLL
TTPAVYCSAIIDSASSFLLVRFTGFSLASFVSTQFWMSSMFSSPKVGLANGVAGGWGN
LGGGAVQLIMPLVFEVVRKIGSTRFTAWRVAFFIPGVMQTFSAIAVLAFGQDMPDGNY
HKLHKTGEMHRDSFRNVLRHAVTNYRAWILALTYGYCFGVELAVDNIVAQYFYDRFG
VNLHTAGLIAASFGMANILVSRPGGGLMSDWLSARFGMRGRLWGLWVVQTIGGVLCV
TQVIFFHGSRYKTETGIMYMGVMILACTLPITLIYFPQWGGMFTGPRPGATAEEYYSSE
WTEEERKKGYNAATERFAENSLREGGRRAASGSQSKHTVPVDGSPPADV OsNRT2.3b nucleic acid sequence, Accession No: AK072215 underlined
character is longest ORF
SEQ ID No. 67
GAGCGCCGGCCTCCCACCGGTCGCGTAAGATCACGCCCGAAATCTTTATTCATTTTCTCT
CCACCGGTTGCCCTCTCGCCGCACCCAACCATCGCGCCACGCCGCGCCGCGCTGCCGGAG
CCGCGCTTTCCGCTATGCTATAAGAGCTGACGCGCAGGGCACAGCGGATGTACGTACACA
CAGTCACTAGCTAAGCTGCTAGCCTTGCTACCACGTGTTGGAGATGGAGGCTAAGCCGGT
GGCGATGGAGGTGGAGGGGGTCGAGGCGGCGGGGGGCAAGCCGCGGTTCAGGATGCCGGT
GGACTCCGACCTCAAGGCGACGGAGTTCTGGCTCTTCTCCTTCGCGAGGCCACACATGGC
CTCCTTCCACATGGCGTGGTTCTCCTTCTTCTGCTGCTTCGTGTCCACGTTCGCCGTGTT
CGCGCGTCTGGCCATGGGCACGGCGTGCGACCTGGTCGGGCCCAGGCTGGCCTCCGCGTC
TCTGATCCTCCTCACCACACCGGCGGTGTACTGCTCCTCCATCATCCAGTCCCCGTCGGG
GTACCTCCTCGTGCGCTTCTTCACGGGCATCTCGCTGGCGTCGTTCGTGTCGGCGCAGTT
CTGGATGAGCTCCATGTTCTCGGCCCCCAAAGTGGGGCTGGCCAACGGCGTGGCCGGCGG
CTGGGGCAACCTCGGCGGCGGCGCCGTCCAGCTGCTCATGCCGCTCGTGTACGAGGCCAT
CCACAAGATCGGTAGCACGCCGTTCACGGCGTGGCGCATCGCCTTCTTCATCCCGGGCCT
GATGCAGACGTTCTCGGCCATCGCCGTGCTGGCGTTCGGGCAGGACATGCCCGGCGGCAA
CTACGGGAAGCTCCACAAGACTGGCGACATGCACAAGGACAGCTTCGGCAACGTGCTGCG
CCACGCCCTCACCAACTACCGCGGCTGGATCCTGGCGCTCACCTACGGCTACAGCTTCGG
CGTCGAGCTCACCATCGACAACGTCGTGCACCAGTACTTCTACGACCGCTTCGACGTCAA
CCTCCAGACCGCCGGGCTCATCGCCGCCAGCTTCGGGATGGCCAACATCATCTCCCGCCC
CGGCGGCGGGCTACTCTCCGACTGGCTCTCCAGCCGGTACGGCATGCGCGGCAGGCTGTG
GGGGCTGTGGACTGTGCAGACCATCGGCGGCGTCCTCTGCGTGGTGCTCGGAATCGTCGA
CTTCTCCTTCGCCGCGTCCGTCGCCGTGATGGTGCTTCTTCGTCCAGGCCGC
GTGCGGGCTCACCTTCGGCATCGTGCCGTTCGTGTCGCGGAGGTCGCTGGGGCTCATCTC
CGGGATGACCGGCGGCGGGGGCAACGTGGGCGCCGTGCTGACGCAGTACATCTTCTTCCA
CGGCACAAAGTACAAGACGGAGACCGGGATCAAGTACATGGGGCTCATGATCATCGCGTG
CACGCTGCCCGTCATGCTCATCTACTTCCCGCAGTGGGGCGGCATGCTCGTAGGCCCGAG
GAAGGGGGCCACGGCGGAGGAGTACTACAGCCGGGAGTGGTCGGATCACGAGCGCGAGAA
GGGTTTCAACGCGGCCAGCGTGCGCGTTCGCGGAGAACAGCGTGCGCGAGGGCGGGAGGTC
GTCGGCGAATGGCGGACAGCCCAGGCACACCGTCCCCGTCGACGCGTCGCCGGCCGGGGT
GTGAAGAATGCCACGGACAATAAGGTCGCGGTTGTAGTACAACTGTACAAATTGATGGTA
CGTGTCGTTTGACCGCGCGCGCGCACAGTGTGGGTCGTGGCCTCGTGGGCTTAGTGGAGT
ACAGTGAGGGGTGTACGTGTGTCGTGGCGCGCGGTCACCTCGGTGGCCTTGGGATTGG
GGGGGCACTATACGCTAGTACTCCAGATATATACGGGTTTGATTTACTTCTGTGGATCGG
CGCTTGTTGGTGGTTTGCTCCCTGTGGTTTTTGTGATGGTAATCATACTCATACTCAAAC
AGTCAAAACTTTTTGATGCG OsNRT2.3a nucleic acid sequence, Accession No: AK109776 underlined
character is longest ORF
SEQ ID No. 68
AGTCACTAGCTAAGCTGCTAGCCTTGCTACCACGTGTTGGAGATGGAGGCTAAGCCGGTG
GCGATGGAGGTGGAGGGGGTCGAGGCGGCGGGGGGCAAGCCGCGGTTCAGGATGCCGGTG
GACTCCGACCTCAAGGCGACGGAGTTCTGGCTCTTCTCCTTCGCGAGGCCACACATGGCC
TCCTTCCACATGGCGTGGTTCTCCTTCTTCTGCTGCTTCGTGTCCACGTTCGCCGCGCCG
CCGCTGCTGCCGCTCATCCGCGACACCCTCGGGCTCACGGCCACGGACATCGGCAACGCC
GGGATCGCGTCCGTGTCGGGCGCCGTGTTCGCGCGTCTGGCCATGGGCACGGCGTGCGAC
CTGGTCGGGCCCAGGCTGGCCTCCGCGTCTCTGATCCTCCTCACCACACCGGCGGTGTAC
```

-continued

SEQUENCE LISTING

```
TGCTCCTCCATCATCCAGTCCCCGTCGGGGTACCTCCTCGTGCGCTTCTTCACGGGCATC
TCGCTGGCGTCGTTCGTGTCGGCGCAGTTCTGGATGAGCTCCATGTTCTCGGCCCCCAAA
GTGGGGCTGGCCAACGGCGTGGCCGGCGGCTGGGGCAACCTCGGCGGCGGCGCCGTCCAG
CTGCTCATGCCGCTCGTGTACGAGGCCATCCACAAGATCGGTAGCACGCCGTTCACGGCG
TGGCGCATCGCCTTCTTCATCCCGGGCCTGATGCAGACGTTCTCGGCCATCGCCGTGCTG
GCGTTCGGGCAGGACATGCCCGGCGGCAACTACGGGAAGCTCCACAAGACTGGCGACATG
CACAAGGACAGCTTCGGCAACGTGCTGCGCCACGCCCTCACCAACTACCGCGGCTGGATC
CTGGCGCTCACCTACGGCTACAGCTTCGGCGTCGAGCTCACCATCGACAACGTCGTGCAC
CAGTACTTCTACGACCGCTTCGACGTCAACCTCCAGACCGCCGGGCTCATCGCCGCCAGC
TTCGGGATGGCCAACATCATCTCCCGCCCCGGCGGCGGGCTACTCTCCGACTGGCTCTCC
AGCCGGTACGGCATGCGCGGCAGGCTGTGGGGGCTGTGGACTGTGCAGACCATCGGCGGC
GTCCTCTGCGTGGTGCTCGGAATCGTCGACTTCTCCTTCGCCGCGTCCGTCGCCGTGATG
GTGCTCTTCTCCTTCTTCGTCCAGGCCGCGTGCGGGCTCACCTTCGGCATCGTGCCGTTC
GTGTCGCGGAGGTCGCTGGGGCTCATCTCCGGGATGACCGGCGGCGGGGCAACGTGGGC
GCCGTGCTGACGCAGTACATCTTCTTCCACGGCACAAAGTACAAGACGGAGACCGGGATC
AAGTACATGGGGCTCATGATCATCGCGTGCACGCTGCCCGTCATGCTCATCTACTTCCCG
CAGTGGGGCGGCATGCTCGTAGGCCCGAGGAAGGGGGCCACGGCGGAGGAGTACTACAGC
CGGGAGTGGTCGGATCACGAGCGCGAGAAGGGTTTCAACGCGGCCAGCGTGCGGTTCGCG
GAGAACAGCGTGCGCGAGGGCGGGAGGTCGTCGGCGAATGGCGGACAGCCCAGGCACACC
GTCCCCGTCGACGCGTCGCCGGCCGGGGTGTGAAGAATGCCAGCGACAATAAGGTCGCGG
TTGTAGTACAACTGTACAAATTGATGGTACGTGTCGTTTGACCGCGCGCGCGCACAGTGT
GGGTCGTGGCCTCGTGGGCTTAGTGGAGTACAGTGAGGGGTGTACGTGTGTCGTGGCGCG
CGCGGTCACCTCGGTGGCCTTGGGATTGGGGGGGCACTATACGCTAGTACTCCAGATATA
TACGGGTTTGATTTACTTCTGTGGATCGGCGCTTGTTGGTGGTTTGCTCCCTGTGGTTTT
TGTGATGGTAATCATACTCATACTCAAACAGTC
```

REFERENCES

1. Edgerton, M. D. Increasing crop productivity to meet global needs for feed, food, and fuel. *Plant Physiol.* 149, 7-13 (2009).
2. Ju, X. T. et al. Reducing environmental risk by improving N management in intensive Chinese agricultural systems. *Proc Natl Acad Sci USA.* 106, 3041-3046 (2009).
3. Guo, J. H. et al. Significant acidification in major Chinese croplands. *Science* 327, 1008-1010 (2010).
4. Xu, G. H., Fan, X. R., Miller, A. J. Plant nitrogen assimilation and use efficiency. *Ann Rev Biol.* 63, 153-182 (2012).
5. Robertson, G. P. & Vitousek, P. M. Nitrogen in agriculture: balancing the cost of an essential resource. *Ann Rev Environ and Res.* 34, 97-125 (2009).
6. Tilman, D., Balzer, C., Hill, J., Befort, B. L. Global food demand and the sustainable intensification of agriculture. *Proc Nat Acad Sci USA.* 108, 20260-20264 (2011).
7. Sutton, M. A., Erisman, W., Leip, A., van Grinsven, H., Winiwarter, W. Too much of a good thing. *Nature* 472, 159-61 (2011).
8. Li, Y. L., Fan, X. R., Shen, Q. R. The relationship between rhizosphere nitrification and nitrogen use efficiency in rice plants. *Plant Cell Environ.* 31, 73-85 (2008).
9. Kirk, G. J. D. & Kronzucker, H. J. The potential for nitrification and nitrate uptake in the rhizosphere of wetland plants: a modeling study. *Ann Bot.* 96, 639-646 (2005).
10. Zhu, Y. et al. Adaptation of plasma membrane H(+)-ATPase of rice roots to low pH as related to ammonium nutrition. *Plant Cell Environ.* 32, 1428-1440 (2009).
11. Araki, R., Hasegawa, H. Expression of rice (*Oryza sativa* L.) genes involved in high-affinity nitrate transport during the period of nitrate induction. *Breeding Sci.* 56, 295-302 (2006).
12. Cai, C. et al. Gene structure and expression of the high-affinity nitrate transport system in rice roots. *J Integ Plant Biol.* 50, 443-451 (2008).
13. Feng, H. M. et al. Spatial expression and regulation of rice high-affinity nitrate transporters by nitrogen and carbon status. *J Exp Bot.* 62, 2319-2332 (2011).
14. Yan, M. et al. Rice OsNAR2.1 interacts with OsNRT2.1, OsNRT2.2 and OsNRT2.3a nitrate transporters to provide uptake over high and low concentration ranges. *Plant Cell Environ.* 34, 1360-1372 (2011).
15. Katayama, H. et al. Production and characterization of transgenic rice plants carrying a high-affinity nitrate transporter gene (OsNRT2.1). *Breeding Sci.* 59, 237-243 (2009).
16. Suzui, N., Nakamura, S., Fujiwara, T., Hayashi, H., Yoneyama, T. A putative acyl-CoA-binding protein is a major phloem sap protein in rice (*Oryza sativa* L.). *J Exp Bot.* 57, 2571-2576 (2006).
17. Rao, T. P., Yano, K., Iijima, M., Yamauchi, A., Tatsumi, J. Regulation of rhizosphere acidification by photosynthetic activity in cowpea (*Vigna unguiculata* L. walp.) seedlings. *Ann Bot.* 89, 213-220 (2002).
18. Miller, A. J., Smith, S. J., Theodoulou, F. L. The heterologous expression of H⁺-coupled transporters in *Xenopus* oocytes. In *Membrane Transport Plants and Fungi: Molecular Mechanisms and Control* (Blatt, M. R., Leigh, R. A. Sanders, D. eds) The Company of Biologists Ltd., Cambridge, UK, pp. 167-178 (1994).
19. Bröer, S. et al. Characterization of the monocarboxylate transporter 1 expressed in *Xenopus laevis* oocytes by changes in cytosolic pH. *Biochem* 1 333, 167-174 (1998).
20. Kurschat, C. E. et al. Alkaline-shifted pH$_0$ sensitivity of AE2c1-mediated anion exchange reveals novel regulatory determinants in the AE2 N-terminal cytoplasmic domain. *J Biol Chem.* 281, 1885-1896 (2006).
21. Foyer, C. H., Bloom, A. J., Queval, G., Noctor, G. Photorespiratory Metabolism: Genes, Mutants, Energetics, and Redox Signaling. *Annu Rev Plant Biol.* 60, 455-484 (2009).
22. Kebeish, R. et al. Chloroplastic photorespiratory bypass increases photosynthesis and biomass production in *Arabidopsis thaliana*. *Nat Biotechnol.* 25, 593-599 (2007).
23. Kosegarten, H., Grolig, F., Wieneke, J., Wilson, G. Hoffmann B. Differential ammonia-elicited changes of cytosolic pH in root hair cells of rice and maize as monitored by 2',7'-bis-(2-carboxyethyl)-5 (and -6)-carboxyfluoresce in -fluorescence ratio. *Plant Physiol.* 113, 451-461 (2007).

24. Raven, J. & Smith, F. Nitrogen assimilation and transport in vascular land plants in relation to intracellular pH regulation. *New Phytol.* 76, 415-431 (1976).
25. Curie, C. & Briat, J. F. Iron transport and signaling in plants. *Ann Rev Plant Biol.* 54, 183-206 (2003).
26. Bellati, J. et al. Intracellular pH sensing is altered by plasma membrane PIP aquaporin co-expression. *Plant Mol Biol.* 74, 105-118 (2010).
27. Rachmilevitch, S., Cousins, A. B., Bloom, A. J. Nitrate assimilation in plant shoots depends on photorespiration. *Proc Nat Acad Sci USA.* 101, 11506-11510 (2004).
28. Stitt, M. et al. Steps towards an integrated view of nitrogen metabolism. *J Exp Bot.* 53, 959-970 (2002).
29. Backhausen, J. E., Kitzmann, C., Scheibe, R. Competition between electron acceptors in photosynthesis—regulation of the malate valve during $CO_2$ fixation and nitrite reduction. *Photosynth Res.* 42, 75-86 (1994).
30. Yamaya, T. et al. Genetic manipulation and quantitative-trait loci mapping for nitrogen recycling in rice. *J. Exp Bot.* 53, 917-925 (2002).
31. Good, A. G. et al. Engineering nitrogen use efficiency with alanine aminotransferase. *Can. J. Bot.* 85, 252-262 (2007).
32. Shrawat, A. K., Carroll, R. T., DePauw, M., Taylor, G. J., Good, A. G. Genetic engineering of improved nitrogen use efficiency in rice by the tissue-specific expression of alanine aminotransferase. *Plant Biotech J.* 6, 722-732 (2008).
33. Ai, P. et al. Two rice phosphate transporters, OsPht1;2 and OsPht1;6, have different functions and kinetic properties in uptake and translocation. *Plant J.* 57, 798-809 (2009).
34. Fan, X. R. et al. Comparing nitrate storage and remobilization in two rice cultivars that differ in their nitrogen use efficiency. *J Exp Bot.* 58, 1729-1740 (2007).
35. Ye, J. et al. A monoclonal-antibody-based ELISA for the detection of human FADD (Fas-associated death domain). *Biotechnol Appl Biochem.* 50, 143-146 (2008).
36. Shanks, J. H., Lappin, T. R., Hill, C. M. In situ hybridization for erythropoietin messenger RNA using digoxigenin-labeled oligonucleotides. *Ann N Y Acad Sci.* 718, 362-365 (1994).
37. Tong, Y. P., Zhou, J. J., Li, Z., Miller, A. J. A two-component high affinity nitrate uptake system in barley. *Plant J.* 41, 442-450 (2005).
38. Orsel, M. et al. Characterization of a two component nitrate transport and signalling high affinity nitrate uptake system in *Arabidopsis*; physiology and protein—protein interaction. *Plant Physiol.* 142, 1304-1317 (2006).
39. Ho, C. H., Lin, S. H., Hu, H. C., Tsay, Y. F. CHL1 functions as a nitrate sensor in plants. *Cell* 138, 1184-94 (2009).
40. Li, C., Wong, W. H. Model based analysis of oligonucleotide arrays: Expression index computation and outlier detection. *Proc Natl Acad Sci USA.* 98, 31-36 (2001).
41. Li, Y., Gao, Y., Xu, X., Shen, Q., Guo, S. Light-saturated photosynthetic rate in high-nitrogen rice (*Oryza sativa* L.) leaves is related to chloroplastic $CO_2$ concentration. *J Exp Bot.* 60, 2351-2360 (2009).
42. Clough S, Bent A (1998) Floral dip: a simplified method for *Agrobacterium*-mediated transformation of *Arabidopsis*. Plant J. 16: 735-743
43. Orsel M, Chopin F, Leleu O, Smith S J, Krapp A, Daniel-Vedele F, Miller A J (2006) Characterization of a Two-Component High-Affinity Nitrate Uptake System in *Arabidopsis*. Physiology and Protein-Protein Interaction. PLANT PHYSIOLOGY 142: 1304-1317
44. Cao A, et al. Serine/threonine kinase gene Stpk-V, a key member of powdery mildew resistance gene Pm21, confers powdery mildew resistance in wheat. Proc Natl Acad Sci USA. 2011 10; 108(19):7727-32.
45. Hirel et al The challenge of improving nitrogen use efficiency in crop plants: towards a more central role for genetic variability and quantitative genetics within integrated approaches. Journal of Experimental Botany, Vol. 58, No. 9, pp. 2369-2387, 2007
46. Saha et al. 1994 Planta 226: 429-442. Fan S-C, Lin C-S, Hsu P-K, Lin S-H, Tsay Y-F (2009) The *Arabidopsis* Nitrate Transporter NRT1.7, Expressed in Phloem, Is Responsible for Source-to-Sink Remobilization of Nitrate. The Plant Cell 21: 2750-2761
47. Jia H, Ren H, Gu M, Zhao J, Sun S, Zhang X, Chen J, Wu P, Xu G (2011) The phosphate transporter gene OsPht1;8 is involved in phosphate homeostasis in rice. Plant Physiol 156: 1164-1175.
48. Kronzucker et al. Nitrate-Ammonium Synergism in Rice. A Subcellular Flux Analysis1. Plant Physiology, March 1999, Vol. 119, pp. 1041-1045,1999
49. Almagro A, Lin S H, Tsay Y F (2008) Characterization of the *Arabidopsis* nitrate transporter NRT1.6 reveals a role of nitrate in early embryo development. Plant Cell 20: 3289-3299
50. Chiu C C, Lin C S, Hsia A P, Su R C, Lin H L, Tsay Y F (2004) Mutation of a nitrate transporter, AtNRT1:4, results in a reduced petiole nitrate content and altered leaf development. Plant Cell Physiol 45: 1139-1148
51. Crawford N M, Glass A D M (1998) Molecular and physiological aspects of nitrate uptake in plants. Trends Plant Sci 3: 389-395
52. Fan S C, Lin C S, Hsu P K, Lin S H, Tsay Y F (2009) The *Arabidopsis* nitrate transporter NRT1.7, expressed in phloem, is responsible for source-tosink remobilization of nitrate. Plant Cell 21: 2750-2761
53. Fan X, Gordon-Weeks R, Shen Q, Miller A J (2006) Glutamine transport and feedback regulation of nitrate reductase activity in barley roots leads to changes in cytosolic nitrate pools. J Exp Bot 57: 1333-1340
54. Forde B G (2000) Nitrate transporters in plants: structure, function and regulation. Biochim Biophys Acta 1465: 219-235
55. Gojon A, Krouk G, Perrine-Walker F, Laugier E (2011) Nitrate transceptor(s) in plants. J Exp Bot 62: 2299-2308
56. Huang N C, Liu K H, Lo H J, Tsay Y F (1999) Cloning and functional characterization of an *Arabidopsis* nitrate transporter gene that encodes a constitutive component of low-affinity uptake. Plant Cell 11: 1381-1392
57. Kirk G J D (2003) Rice root properties for internal aeration and efficient nutrient acquisition in submerged soil. New Phytol 159: 185-194
58. Kronzucker H J, Glass A D M, Siddiqi M Y, Kirk G J D (2000) Comparative kinetic analysis of ammonium and nitrate acquisition by tropical lowland rice: implications for rice cultivation and yield potential. New Phytol 145: 471-476
59. Li B Z, Xin W J, Sun S B, Shen Q R, Xu G H (2006) Physiological and molecular responses of nitrogen-starved rice plants to re-supply of different nitrogen sources. Plant Soil 287: 145-159
60. Li J Y, Fu Y L, Pike S M, Bao J, Tian W, Zhang Y, Chen C Z, Zhang Y, Li H M, Huang J, et al (2010) The *Arabidopsis* nitrate transporter NRT1.8 functions in nitrate removal from the xylem sap and mediates cadmium tolerance. Plant Cell 22: 1633-1646

61. Lin C M, Koh S, Stacey G, Yu S M, Lin T Y, Tsay Y F (2000) Cloning and functional characterization of a constitutively expressed nitrate transporter gene, OsNRT1, from rice. Plant Physiol 122: 379-388
62. Lin S H, Kuo H F, Canivenc G, Lin C S, Lepetit M, Hsu P K, Tillard P, Lin H L, Wang Y Y, Tsai C B, et al (2008) Mutation of the *Arabidopsis* NRT1.5 nitrate transporter causes defective root-to-shoot nitrate transport. Plant Cell 20: 2514-2528
63. Liu K H, Tsay Y F (2003) Switching between the two action modes of the dual-affinity nitrate transporter CHL1 by phosphorylation. EMBO J 22: 1005-1013
64. Miller A J, Fan X, Orsel M, Smith S J, Wells D M (2007) Nitrate transport and signalling. J Exp Bot 58: 2297-2306
65. Miller A J, Fan X, Shen Q, Smith S J (2008) Amino acids and nitrate as signals for the regulation of nitrogen acquisition. J Exp Bot 59: 111-119
66. Okamoto M, Kumar A, Li W B, Wang Y, Siddiqi M Y, Crawford N M, Glass A D M (2006) High-affinity nitrate transport in roots of *Arabidopsis* depends on expression of the NAR2-like gene AtNRT3.1. Plant Physiol 140:1036-1046
67. Orsel M, Krapp A, Daniel-Vedele F (2002) Analysis of the NRT2 nitrate transporter family in *Arabidopsis*: structure and gene expression. Plant Physiol 129: 886-896
68. Tsay Y F, Chiu C C, Tsai C B, Ho C H, Hsu P K (2007) Nitrate transporters and peptide transporters. FEBS Lett 581: 2290-2300
69. Wang Y Y, Tsay Y F (2011) *Arabidopsis* nitrate transporter NRT1.9 is important in phloem nitrate transport. Plant Cell 23: 1945-1957
70. Xu G, Fan X, Miller A J (2012) Plant nitrogen assimilation and use efficiency. Annu Rev Plant Biol 63: 153-182
71. Yong Z, Kotur Z, Glass A D M (2010) Characterization of an intact two component high-affinity nitrate transporter from *Arabidopsis* roots. Plant J 63: 739-748
72. Zhou J J, Fernandez E, Galván A, Miller A J (2000) A high affinity nitrate transport system from *Chlamydomonas* requires two gene products. FEBS Lett 466: 225-227
73. Zhuo D G, Okamoto M, Vidmar J J, Glass A D M (1999) Regulation of a putative high-affinity nitrate transporter (Nrt2; 1At) in roots of *Arabidopsis thaliana*. Plant J 17: 563-568

The invention is further described by the following numbered paragraphs:

1. A method for increasing growth, yield, nitrogen use efficiency, nitrogen transport, nitrogen stress tolerance, pathogen resistance, survival and/or nitrogen acquisition of a plant comprising introducing and expressing a nucleic acid construct comprising a nucleic acid sequence as defined in SEQ ID No. 1, a functional variant or homolog thereof operably linked to a regulatory sequence in a plant wherein if the nucleic acid sequence is as defined in SEQ ID No. 1, said plant is not rice.

2. A method according to paragraph 1 wherein said regulatory sequence is a constitutive or strong promoter directing overexpression of said nucleic acid.

3. A method according to paragraph 2 wherein said constitutive or strong promoter is selected from CaMV-35S, CaMV-35Somega, *Arabidopsis* ubiquitin UBQ1.

4. A method according to paragraph 1 wherein said regulatory sequence is a phloem specific promoter.

5. A method according to paragraph 4 wherein said phloem specific promoter comprises a nucleic acid comprising SEQ ID No. 5.

6. A method for making a transgenic plant having increased growth, yield, nitrogen transport, nitrogen acquisition, nitrogen stress tolerance and/or nitrogen use efficiency comprising
a) introducing and expressing in a plant or plant cell a nucleic acid construct comprising a nucleic acid sequence as defined in SEQ ID No. 1, a functional variant or homolog thereof operably linked to a regulatory sequence wherein if the nucleic acid sequence is as defined in SEQ ID No. 1, said plant is not rice.

7. A method according to any of paragraphs 1 to 6 wherein said plant is a crop plant or a biofuel plant.

8. A method according to paragraph 7 wherein said crop plant is selected from maize, wheat, tobacco, oilseed rape, sorghum, soybean, potato, tomato, grape, barley, pea, bean, field bean, lettuce, cotton, sugar cane, sugar beet, broccoli or other vegetable brassicas or poplar.

9. A plant obtained or obtainable from a method as defined in any of paragraphs 6 to 8.

10. A transgenic plant expressing a nucleic acid construct comprising a nucleic acid sequence as defined in SEQ ID No. 1, a functional variant or homolog thereof operably linked to a regulatory sequence if the nucleic acid sequence is as defined in SEQ ID No. 1, said plant is not rice.

11. A plant according to paragraph 9 or 10 wherein said regulatory sequence is a constitutive or strong promoter directing overexpression of said nucleic acid.

12. A plant according to paragraph 11 wherein said constitutive promoter or strong is selected from CaMV-35S, CaMV-35Somega, *Arabidopsis* ubiquitin UBQ1.

13. A plant according to any of paragraphs 9 or 10 wherein said regulatory sequence is a phloem specific promoter.

14. A plant according to paragraph 13 wherein said phloem specific promoter comprises a nucleic acid comprising SEQ ID No. 5.

15. A plant according to any of paragraphs 9 to 14 wherein said plant is a crop plant a biofuel plant.

16. A plant according to paragraph 15 wherein said crop plant is selected from maize, wheat, oilseed rape, tobacco, sorghum, soybean, potato, tomato, grape, barley, pea, bean, field bean, lettuce, cotton, sugar cane, sugar beet, broccoli or other vegetable brassicas or poplar.

17. A method for regulating pH homeostasis comprising introducing and expressing a nucleic acid construct comprising a nucleic acid sequence comprising SEQ ID No. 1, a functional variant or homolog thereof operably linked to a regulatory sequence in a plant.

18. A method for reducing acidification in a plant comprising introducing and expressing a nucleic acid construct comprising a nucleic acid sequence comprising SEQ ID No. 1, a functional variant or homolog thereof operably linked to a regulatory sequence in a plant.

19. A method for altering nitrate transport and pH homeostasis in a plant comprising introducing and expressing a nucleic acid construct comprising a nucleic acid sequence comprising SEQ ID No. 1, a functional variant or homolog thereof operably linked to a regulatory sequence in a plant wherein said nucleic acid comprises a mutation in the pH sensing motif VYEAIHKI (SEQ ID No. 16).

20. The use of a nucleic acid with homology to SEQ ID No. 1, a functional variant or homolog thereof comprising the pH sensing motif VYEAIHKI (SEQ ID No. 16) in regulating pH in altering nitrate transport and pH homeostasis in a plant.

21. A method for increasing growth, yield, nitrogen use efficiency, nitrogen transport, pathogen resistance, survival, nitrogen stress tolerance and/or nitrogen acquisition of a plant comprising introducing and expressing a nucleic acid construct comprising a nucleic acid sequence as defined in SEQ ID No. 1, a functional variant or homolog thereof operably linked to a regulatory sequence into a plant wherein said regulatory sequence is a constitutive promoter or a phloem specific promoter and wherein said plant does not overexpress a nucleic acid sequence comprising SEQ ID No. 2.

22. A method for making a transgenic plant having increased growth, yield, nitrogen transport, nitrogen acquisition, nitrogen stress tolerance and/or nitrogen use efficiency comprising a) introducing and expressing in a plant or plant cell a nucleic acid construct comprising a nucleic acid sequence as defined in SEQ ID No. 1, a functional variant or homolog thereof operably linked to a regulatory sequence wherein said regulatory sequence is a constitutive promoter or a phloem specific promoter and wherein said plant does not overexpress a nucleic acid sequence comprising SEQ ID No. 2.

23. A method according to any of paragraphs 21 to 22 wherein said regulatory sequence is a constitutive or strong promoter directing overexpression of said nucleic acid.

24. A method according to paragraph 23 wherein said constitutive or strong promoter is selected from CaMV-35S, CaMV-35Somega, *Arabidopsis* ubiquitin UBQ1.

25. A method according to any of paragraphs 21 to 22 wherein said regulatory sequence is a phloem specific promoter.

26. A method according to paragraph 25 wherein said phloem specific promoter comprises a nucleic acid comprising SEQ ID No. 5.

27. A method according to any of paragraphs 21 to 26 wherein said plant is a crop plant or a biofuel plant.

28. A method according to paragraph 27 wherein said crop plant is selected from maize, rice, wheat, oilseed rape, tobacco, sorghum, soybean, potato, tomato, grape, barley, pea, bean, field bean, lettuce, cotton, sugar cane, sugar beet, broccoli or other vegetable brassicas or poplar.

29. A method according to paragraph 28 wherein said crop plant is not rice.

30. A plant obtained or obtainable from a method as defined in any of paragraphs 21 to 29.

31. A transgenic plant expressing a nucleic acid construct comprising a nucleic acid sequence as defined in SEQ ID No. 1, a functional variant or homolog thereof operably linked to a regulatory sequence into a plant wherein said regulatory sequence is a constitutive promoter or a phloem specific promoter and wherein said plant does not overexpress a nucleic acid sequence comprising SEQ ID No. 2.

32. A plant according to paragraph 30 or 31 wherein said regulatory sequence is a constitutive or strong promoter directing overexpression of said nucleic acid.

33. A plant according to paragraph 32 wherein said constitutive promoter or strong is selected from CaMV-35S, CaMV-35Somega, *Arabidopsis* ubiquitin UBQ1.

34. A plant according to any of paragraphs 30 to 31 wherein said regulatory sequence is a phloem specific promoter.

35. A plant according to paragraph 34 wherein said phloem specific promoter comprises a nucleic acid comprising SEQ ID No. 5.

36. A plant according to any of paragraphs 31 to 35 wherein said plant is a crop plant or biofuel plant.

37. A plant according to paragraph 36 wherein said crop plant is selected from maize, rice, wheat, oilseed rape, sorghum, soybean, potato, tomato, grape, barley, pea, bean, field bean, lettuce, cotton, sugar cane, sugar beet, broccoli or other vegetable brassicas or poplar.

38. A plant according to paragraph 37 wherein said crop plant is not rice.

39. A product derived from a plant as defined in any of paragraphs 9 to 16 or 31 to 38.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method for increasing growth, yield, nitrogen use efficiency, nitrogen transport, nitrogen stress tolerance, pathogen resistance, survival and/or nitrogen acquisition of a plant comprising introducing and expressing a nucleic acid construct comprising a nucleic acid sequence encoding a nitrate transporter having pH sensing motif comprising VYEAIHKI and encoding a polypeptide comprising SEQ ID NO: 3 or homolog thereof, operably linked to a regulatory sequence in a plant wherein if the polypeptide encoded comprises SEQ ID NO: 3, said plant is not rice.

2. A method according to claim 1, wherein said regulatory sequence is a constitutive promoter directing overexpression of said nucleic acid.

3. A method according to claim 1, wherein said regulatory sequence is a phloem specific promoter.

4. A method for making a transgenic plant having increased growth, yield, nitrogen transport, nitrogen acquisition, nitrogen stress tolerance and/or nitrogen use efficiency comprising
   a) introducing and expressing in a plant or plant cell a nucleic acid construct comprising a nucleic acid sequence encoding a nitrate transporter having pH sensing motif comprising VYEAIHKI and encoding a polypeptide comprising SEQ ID NO: 3 or homolog thereof, operably linked to a regulatory sequence wherein if the polypeptide comprises SEQ ID NO: 3, said plant is not rice.

5. A method according to claim 1, wherein said plant is a crop plant or a biofuel plant or bioenergy crop, wherein the biofuel plant or bioenergy crop is selected from the group consisting of rape/canola, sugar cane, sweet sorghum, Panicum virgatum (switchgrass), linseed, lupin, willow, poplar, poplar hybrid Miscanthus or gymnosperm, loblolly pine, maize, grass.

6. The method according to claim 5, wherein said crop plant is selected from maize, wheat, tobacco, oilseed rape, sorghum, soybean, potato, tomato, grape, barley, pea, bean, field bean, lettuce, cotton, sugar cane, sugar beet, broccoli or other vegetable brassicas or poplar.

7. The method according to claim 5, wherein said plant is maize or soybean.

8. A method according to claim 1, wherein said plant is maize or soybean and said homolog is from maize or soybean.

9. A plant obtained or obtainable from a method as defined in claim 8, wherein the plant comprises said nucleic acid construct.

10. A transgenic plant expressing a nucleic acid construct comprising a nucleic acid sequence encoding a nitrate transporter having pH sensing motif comprising VYEAIHKI and encoding a polypeptide comprising SEQ ID NO: 3 or homolog thereof, operably linked to a regulatory sequence wherein if the polypeptide comprises SEQ ID NO: 3, said plant is not rice.

11. The plant according to claim 10, wherein said regulatory sequence is a constitutive promoter directing overexpression of said nucleic acid.

12. The plant according to claim 10, wherein said regulatory sequence is a phloem specific promoter.

13. The plant according to claim 10, wherein said plant is a crop plant or a biofuel plant or bioenergy crop, wherein the biofuel plant or bioenergy crop is selected from the group consisting of rape/canola, sugar cane, sweet sorghum, Panicum virgatum (switchgrass), linseed, lupin, willow, poplar, poplar hybrid Miscanthus or gymnosperm, loblolly, pine, maize, grass.

14. The plant according to claim 13, wherein said crop plant is selected from maize, wheat, oilseed rape, tobacco, sorghum, soybean, potato, tomato, grape, barley, pea, bean, field bean, lettuce, cotton, sugar cane, sugar beet, broccoli or other vegetable brassicas or poplar.

15. The plant according to claim 10, wherein said plant is maize or soybean.

16. The plant according to claim 10, wherein said plant is maize or soybean and said homolog is from maize or soybean.

17. A method for regulating pH homeostasis or reducing/altering acidification in a plant comprising introducing and expressing a nucleic acid construct comprising a nucleic acid sequence encoding a nitrate transporter having pH sensing motif comprising VYEAIHKI and encoding a polypeptide comprising SEQ ID NO: 3 or homolog thereof, operably linked to a regulatory sequence in a plant.

18. The method according to claim 17, wherein said plant is selected from maize, wheat, tobacco, oilseed rape, sorghum, soybean, potato, tomato, grape, barley, pea, bean, field bean, lettuce, cotton, sugar cane, sugar beet, broccoli or other vegetable brassicas or poplar.

19. The method according to claim 17, wherein said plant is maize or soybean.

20. The method according to claim 17, wherein said plant is maize or soybean and wherein said homolog is from maize or soybean.

21. The method according to claim 17, wherein said regulatory sequence is a constitutive directing overexpression of said nucleic acid.

22. The method according to claim 17, wherein said regulatory sequence is a phloem specific promoter.

23. The method of claim 1, wherein said homolog comprises a sequence having at least 95% identity to SEQ ID NO: 3.

24. The method of claim 4, wherein said homolog comprises a sequence having at least 95% identity to SEQ ID NO: 3.

25. The method of claim 17, said homolog comprises a sequence having at least 95% identity to SEQ ID NO: 3.

26. The plant of claim 10, said homolog comprises a sequence having at least 95% identity to SEQ ID NO: 3.

27. The method of claim 1, wherein said plant comprising said nucleic acid sequence has increased nitrogen update in the absence of a nucleic acid sequence introduced into said plant comprising OsNAR21.

28. The method of claim 1, wherein said plant comprising said nucleic acid sequence has reduced acidification compared to a plant not comprising said construct.

29. A method for increasing growth, yield, nitrogen use efficiency, nitrogen transport, nitrogen stress tolerance, pathogen resistance, survival and/or nitrogen acquisition of a plant comprising introducing and expressing a nucleic acid construct comprising a nucleic acid encoding a nitrate transporter having pH sensing motif comprising VYEAIHKI and encoding a polypeptide comprising SEQ ID NO: 3 or a sequence having at least 95% identity to SEQ ID NO: 3, operably linked to a regulatory sequence in a plant wherein if the polypeptide encoded comprises SEQ ID NO: 3, said plant is not rice.

* * * * *